(12) United States Patent
Asano et al.

(10) Patent No.: US 9,181,574 B2
(45) Date of Patent: Nov. 10, 2015

(54) L-AMINO ACID OXIDASE, METHOD FOR MEASURING L-LYSINE, KIT AND ENZYME SENSOR

(71) Applicants: Yasuhisa Asano, Toyama (JP); Daisuke Matsui, Toyama (JP)

(72) Inventors: Yasuhisa Asano, Toyama (JP); Daisuke Matsui, Toyama (JP)

(73) Assignees: AJINOMOTO CO., INC., Tokyo (JP); TOYAMA PREFECTURE, Toyama (JP)

( * ) Notice: Subject to any disclaimer, the term of this patent is extended or adjusted under 35 U.S.C. 154(b) by 0 days.

(21) Appl. No.: 14/445,597

(22) Filed: Jul. 29, 2014

(65) Prior Publication Data
US 2014/0335553 A1 Nov. 13, 2014

Related U.S. Application Data

(63) Continuation of application No. PCT/JP2013/051894, filed on Jan. 29, 2013.

(30) Foreign Application Priority Data

Jan. 30, 2012 (JP) .................. 2012-016165

(51) Int. Cl.
| | | |
|---|---|---|
| C12N 9/06 | (2006.01) | |
| C12Q 1/00 | (2006.01) | |
| C12Q 1/26 | (2006.01) | |
| C12Q 1/28 | (2006.01) | |

(52) U.S. Cl.
CPC .............. *C12Q 1/005* (2013.01); *C12N 9/0022* (2013.01); *C12Q 1/26* (2013.01); *C12Q 1/28* (2013.01); *C12Q 2533/00* (2013.01)

(58) Field of Classification Search
CPC ........ C12N 9/0022; C12Q 1/004; C12Q 1/26; C12Q 1/28; C12Y 104/03002
See application file for complete search history.

(56) References Cited

U.S. PATENT DOCUMENTS

| 4,234,691 A | 11/1980 | Kusakabe et al. |
| 7,407,784 B2 | 8/2008 | Butzke et al. |
| 2013/0052679 A1 | 2/2013 | Asano et al. |
| 2013/0344526 A1 | 12/2013 | Asano et al. |

FOREIGN PATENT DOCUMENTS

| CN | 102296104 | 12/2011 |
| EP | 0747477 | 12/1996 |

(Continued)

OTHER PUBLICATIONS

Lucas-Elio, P., et al., 2006, "The antimicrobial actifiry of marinocine, synthesized by Marinomonas med iterreanea, is due to hydrogen peroxide generated by its lysine oxidase activity", Journal of Bacteriology, vol. 188, No. 7, pp. 2493-2501.*

(Continued)

*Primary Examiner* — Manjunath Rao
*Assistant Examiner* — William W Moore
(74) *Attorney, Agent, or Firm* — Shelly Guest Cermak; Cermak Nakajima & McGowan LLP

(57) ABSTRACT

Methods are provided measuring L-lysine using a variant enzyme, an L-lysine measurement kit, and an enzyme sensor. Variant L-amino acid oxidase having a predetermined amino acid mutation, and having oxidase activity that is highly substrate-specific for L-lysine; a method for measuring L-lysine using this variant enzyme; an L-lysine measurement kit; and an enzyme sensor are also provided.

15 Claims, 9 Drawing Sheets

(56) References Cited

FOREIGN PATENT DOCUMENTS

| JP | 55-43409 | 3/1980 | | |
|---|---|---|---|---|
| JP | 2011043396 | 3/2011 | | |
| WO | WO2006/129513 | 12/2006 | | |
| WO | WO2010/039750 | 4/2010 | | |
| WO | WO 2011/021657 A1 | * | 2/2011 | ............... C12Q 1/32 |

OTHER PUBLICATIONS

Gomez, D., et al., 2006, "A novel type of lysine oxidase: L-lysine -[epsilon]-oxidase", vol. 1764, pp. 1577-1585.*

Gomez, D., et al., 2010, "Both genes in the *Marinomonas mediterranea* lodAB operon are required for the expression of the antimicrobial protein lysine oxidase", Molecuar Microbiology, vol. 75, No. 2, pp. 462-473.*

Sanchez-Amat, A., et al., 2010, "Finding new enzymes from bacterial physiology: A successful approach illustrated by the detection of novel oxidases in *Marinomonas mediterranea*", Marine Drugs, vol. 8, pp. 519-541.*

Chalcraft, K. R., et al., "Newborn Screening of Inborn Errors of Metabolism by Capillary Electrophoresis-Electrospray Ionization-Mass Spectrometry: A Second-Tier Method with Improved Specificity and Sensitivity," Anal. Chem. 2009;81:307-314.

Endo, H., et al., "Optical enzyme sensor for determining L-lysine content using L-lysine oxidase from the rockfish *Sebastes schlegeli*," Anal. Bioanal. Chem. 2008;391:1255-1261.

Flashner, M. I. S., et al., "Purification and Properties of L-Lysine Monooxygenase from *Pseudomonas fluorescens*," J. Biol. Chem. 1974;249:2579-2586.

Flashner, M. I. S., et al., "Regulatory Properties of the Flavoprotein L-Lysine Monooxygenase," J. Biol. Chem. 1974;249:2587-2592.

Guerrieri, A., et al., "The kinetic and analytical behaviours of an L-lysine amperometric biosensor based on lysine oxidase immobilised onto a platinum electrode by co-crosslinking," Sens. Actuators 2007;B 126:424-430.

Matsuda, M., et al., "Determination of plasma and serum L-lysine using L-lysine epsilon-oxidase from *Marinomonas mediterranea* NBRC 103028T," Anal. Biochem. 2010;406:19-23.

Office Action from Japanese Patent App. No. 2012-016165 (Nov. 19, 2012) with English language translation thereof, issued Nov. 27, 2012.

International Search Report and Written Opinion for PCT Patent App. No. PCT/JP2013/051894 (Mar. 12, 2013).

International Preliminary Report on Patentability for PCT Patent App. No. PCT/JP2013/051894 (Aug. 5, 2014) with English language translation thereof.

Office Action from Chinese Patent App. No. 201380007227.2 (Mar. 9, 2015).

* cited by examiner

Fig. 3

```
         10         20         30         40         50         60         70         80         90
MNNNNRHPAD GKKPITIFGP DFPFAFDDNL EHPAGLGSIP AARHGEEVAI VGAGIAGLVA AYELMKLGLK PVVYEASKNG GRLRSDAFNG
         100        110        120        130        140        150        160        170        180
TDGIIAELGG MRFPVSSTAF YHYVDKLGLE TKPFPNPLTP ASRSTVIDLE GQTYYAEKAA DLPALFQEVT DAWADALESG ARFGDIQQAI
         190        200        210        220        230        240        250        260        270
RDRQVPRLKE LWNTLVPLWD DRTFYDFVAT SKAFAKLSFQ HREVFGQVGF GTGGNDSOFP NSMLEIFRVV NTNQDHQHL VVGGVEQVPQ
         280        290        300        310        320        330        340        350        360
GINRHVPERC AHMPEGTSLS SLHGGAPRTG VKRIARASDG RLAVTDNWGD CRHYAAVLTT QQSMLLTTGI DCEESLFSGK MMMALDRTRY
         370        380        390        400        410        420        430        440        450
MQSSKTFWV DRFFWKDKDP ETGRDLMSMT LTDRLTRGTY LFDNGDDKPG VICLSYANMS DALKMLPHPV EKRVQLALDA LKKIYPKTDI
         460        470        480        490        500        510        520        530        540
AGHIIGDPIT ISMEADPHFL GASKGALPGH YRYNQRMYAH FMQAQMPVEQ RGIFIAGDDV SWTPANVEGA VQTSLNAVNG IMNHFGGKTH
         550        560
ADNPGPGDVF DEIGQIALAD *
```

Fig. 7
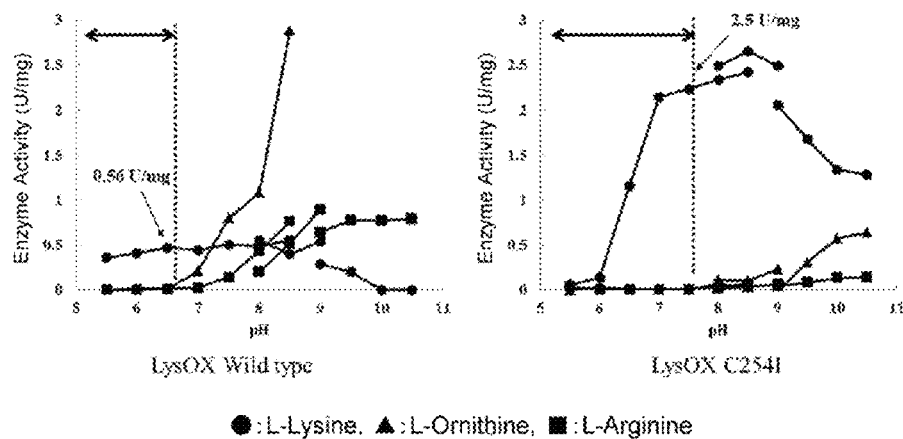
Fig. 8A-B
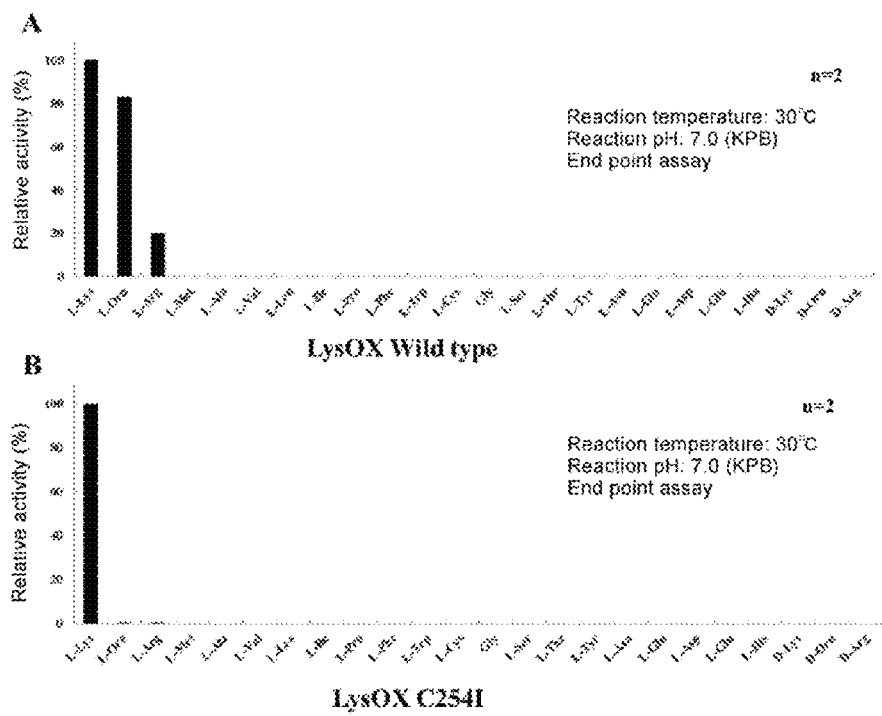

L-AMINO ACID OXIDASE, METHOD FOR MEASURING L-LYSINE, KIT AND ENZYME SENSOR

This application is a Continuation of, and claims priority under 35 U.S.C. §120 to, International Application No. PCT/JP2013/051894, filed Jan. 29, 2013, and claims priority therethrough under 35 U.S.C. §119 to Japanese Patent Application No. 2012-16165, filed on Jan. 30, 2012, the entireties of which are incorporated herein. Also, the Sequence Listing electronically filed herewith is hereby incorporated by reference (File name: 2014-07-29T_US-517_Seq_List; File size: 86 KB; Date recorded: Jul. 29, 2014.)

BACKGROUND

1. Technical Field

The present invention relates to a novel L-amino acid oxidase, a method for measuring L-lysine using this novel L-amino acid oxidase, a kit employed in this method, and an enzyme sensor. More particularly, the present invention relates to a variant L-amino acid oxidase with high substrate specificity for L-lysine, a method for measuring L-lysine employing this variant enzyme, an L-lysine measurement kit, and an enzyme sensor.

2. Brief Description of the Related Art

L-lysine, one of the constituent amino acids of proteins, is an essential amino acid that cannot be produced within the body. The concentration of amino acids including L-lysine within the body is kept at homeostasis. However, congenital metabolic anomalies and internal disorders can cause great fluctuation in blood concentrations. The concentration of not just L-lysine, but of other amino acids within the body, affords a useful means of detecting disease. Thus, by measuring the blood concentration of one or many amino acids, it is possible to detect disease (International publication No. WO2006/129513 and Anal. Chem. 81: 307-314 (2009)).

In recent years, a large number of methods employing enzymes have become known as methods of quantifying amino acid levels. These methods employing enzymes are advantageous since they are less expensive and easier to implement than instrumental analysis methods. For example, enzymes such as dehydrogenase and oxidase are often employed. An example of a quantification method employing oxidase is the use of peroxidase to detect the hydrogen peroxide that is produced by subjecting amino acids to the action of oxidase (Japanese Un-examined patent publication No. Shou55-43409). This detection and quantification can be conducted with a method such as the colorimetric method, fluorescence method, or electrode method.

Methods employing enzymes are also known as methods of quantifying L-lysine. For example, in quantification with oxidase, L-lysine α-oxidase [EC 1.4.3.14] has been employed. L-lysine α-oxidase derived from *Trichoderma viride* affords a higher substrate specificity than other L-amino acid oxidases, and is commercially available. Thus, it has come to be employed in elements such as enzymatic sensors (Guerrieri et al., *Sens. Actuators, B* 126: 424-430 (2007); Endo et al. *Anal. Bioanal. Chem.* 391: 1255-1261 (2008); Anal. Bioanal. Chem. 406: 19-23 (2010)).

There are also reports that L-lysine monooxidase derived from *Pseudomonas fluorescens* exhibits an L-lysine oxygenase activity (Flashner et al., *J. Biol. Chem.* 249: 2579-2586 (1974); Flashner et al., *J. Biol. Chem.* 249: 2587-2592 (1974)). This enzyme employs L-lysine, L-threonine, and L-arginine as substrates.

However, the *Trichoderma viride*-derived L-lysine α-oxidase also exhibits oxidase activity on amino acids other than L-lysine. Thus, when employing L-lysine α-oxidase to quantify a sample containing multiple amino acids, such as blood plasma, excess evaluation tends to be involved.

Furthermore, it has recently been reported that L-lysine α-oxidase derived from the mucus of saltwater fish has greater substrate specificity than the above L-lysine α-oxidase (Endo et al., *Anal. Bioanal. Chem.* 391: 1255-1261 (2008)). However, this L-lysine α-oxidase is derived from the mucus of saltwater fish, and there are no reports of enzyme production by culturing. Accordingly, it is difficult to produce large quantities of this enzyme for use in quantifying L-lysine.

There have been no reports of using the *Pseudomonas fluorescens*-derived L-lysine monooxygenase to quantify L-lysine. Even when this enzyme is employed to quantify L-lysine, as set forth above, because it has oxygenase activity on L-ornithine and L-arginine in addition to L-lysine, it is impossible to strictly quantify L-lysine in samples containing multiple amino acids, such as blood plasma.

Methods of quantifying L-lysine based on oxidase, if successful, would be useful from the perspective of being less expensive and more convenient than instrumental analysis methods. However, as stated above, for samples containing multiple amino acids, such as blood plasma, the substrate specificity is low or there are problems with enzyme productivity with respect to the enzymes that are currently available. From this perspective, these enzymes are not practical.

SUMMARY

Accordingly, it is an aspect of the present invention to provide an enzyme with high substrate specificity for L-lysine that enables specific quantification of L-lysine even in biological samples containing multiple amino acids, and to provide a method for enzymatically measuring L-lysine using this enzyme.

It is a further aspect of the present invention to provide a quantifying kit that can be used when implementing the above enzymatic measurement method.

It is a further aspect of the present invention to provide an enzyme sensor that can be used in the above enzymatic measurement method.

It is described that a variant L-amino acid oxidase, obtained by replacing the cysteine at position 254 in the amino acid sequence of L-amino acid oxidase derived from *Pseudomonas* sp. H-8-1-3 with a prescribed amino acid, exhibited high substrate specificity for L-Lysine.

It is a first aspect of the invention to provide a protein selected from the group consisting of:

(1) a protein comprising the amino acid sequence of SEQ ID NO: 2, but wherein the cysteine at position 254 has been replaced with an amino acid selected from the group consisting of methionine, phenylalanine, tyrosine, tryptophan, alanine, glycine, valine, isoleucine, leucine, lysine, arginine, histidine, aspartic acid, glutamic acid, serine, threonine, asparagine, glutamine, and proline;

(2) a second protein comprising the amino acid sequence of the protein specified in (1) above, wherein one or a plurality of amino acids other than the amino acid at position 254 have been deleted, substituted, and/or added, wherein said second protein has an oxidase activity with a higher substrate specificity for L-lysine than the amino acid oxidase consisting of the amino acid sequence of SEQ. ID NO: 2; and (3) a third protein comprising the amino acid sequence having at least 90% sequence identity with the amino acid sequence of the protein specified in (1) above, wherein the amino acid at position 254 of the third protein is selected from the group consisting of methionine, phenylalanine, tyrosine, tryptophan, alanine, glycine, valine, isoleucine, leucine, lysine, arginine, histidine, aspartic acid, glutamic acid, serine, threonine, asparagine, glutamine, and proline, and wherein said third protein has oxidase activity with a higher substrate specificity for L-lysine than the amino acid oxidase consisting of the amino acid sequence of SEQ. ID NO: 2.

It is a further aspect of the invention to provide the protein as described above, wherein the 254th amino acid is selected from the group consisting of methionine, phenylalanine, tyrosine, alanine, valine, isoleucine, leucine, aspartic acid, glutamic acid, and serine.

It is a further aspect of the invention to provide the protein as described above, wherein the 254th amino acid is isoleucine or tyrosine.

It is a further aspect of the invention to provide the protein as described above, wherein the amino acid at position 254 is other than tryptophan, glycine, lysine, arginine, histidine, threonine, asparagine, glutamine, or proline, and the oxidase activity of the second or third protein on L-arginine is 15% or less than the oxidase activity on L-lysine, and the oxidase activity of the second or third protein on L-ornithine is 80% or less than the oxidase activity on L-lysine.

It is a further aspect of the invention to provide a nucleic acid coding for the protein as described above.

It is a further aspect of the invention to provide a vector containing the nucleic acid as described above.

It is a further aspect of the invention to provide a transformant that has been transformed by the vector as described above.

It is a further aspect of the invention to provide a method for detecting or quantifying L-lysine, comprising:

(A) maintaining a specimen and the protein as described above in the presence of water and oxygen; and (B) detecting or quantifying at least one reaction product produced in the reaction solution by the effect of the oxidase activity of the protein on L-lysine.

It is a further aspect of the invention to provide a method as described above, wherein the reaction product that is detected or quantified in step (B) is hydrogen peroxide.

It is a further aspect of the invention to provide a method as described above, wherein the hydrogen peroxide is detected or quantified using peroxidase.

It is a further aspect of the invention to provide a method as described above, wherein the reaction product that is detected or quantified in step (B) is ammonia.

It is a further aspect of the invention to provide a method as described above, wherein the ammonia is detected or quantified using an ammonia-detecting reagent.

It is a further aspect of the invention to provide a method as described above, wherein the reaction product that is detected or quantified in step (B) is a deamination product of L-lysine.

It is a further aspect of the invention to provide a kit for detecting or quantifying L-lysine, comprising the protein as described above.

It is a further aspect of the invention to provide a kit as described above, further comprising a kit component selected from the group consisting of a reaction buffer, a hydrogen peroxide-detecting reagent, an ammonia-detecting reagent, and an L-lysine deamination product-detecting agent.

It is a further aspect of the invention to provide a L-lysine-detecting or quantifying enzyme sensor comprising an electrode for detecting hydrogen peroxide, wherein the protein as described above is disposed on the surface or in the vicinity of the electrode for detecting hydrogen peroxide.

It is a further aspect of the invention to provide a sensor as described above, wherein the electrode for detecting hydrogen peroxide is an enzymatic hydrogen peroxide electrode or a diaphragm hydrogen peroxide electrode.

The present invention provides a novel variant L-amino acid oxidase with high substrate specificity for L-lysine. Using this variant L-amino acid oxidase, it is possible to conveniently and rapidly detect and quantify L-lysine with specificity and good precision even in samples containing numerous impurities such as other amino acids. In particular, the present invention is effective for biological samples such as blood plasma, blood serum, and urine. By inducing coupling with enzymes such as peroxidase, not only is it possible to quantify L-lysine by the fluorescence method and chromogenic method, but it is also possible to provide an electrode-type enzyme sensor.

BRIEF DESCRIPTION OF THE DRAWINGS

FIG. 3 shows the amino acid sequence expected based on the base pair sequence coding for the above wild-type enzyme.

In FIG. 4-4a, the LysOX Wild-type denotes the L-amino acid oxygenase derived from *Pseudomonas* sp. H-8-1, LysOX C254I denotes the variant enzyme C254I, and the remaining known amino acid sequences denote accession numbers.

FIG. 7 shows the results of examining the enzymatic activity (pH dependence) with L-lysine, L-ornithine, and L-arginine as substrates for wild-type enzyme and the variant enzyme C254I of the present invention.

FIG. 8A-B show the results of examining the substrate specificity of wild-type enzyme and the variant enzyme C254I of the present invention.

In FIG. 9, the results of the wild-type enzyme are indicated by LysOX Wild-type, and the results of the variant enzyme C254I of the present invention are indicated by LysOX C254I.

DETAILED DESCRIPTION OF THE EXEMPLARY EMBODIMENTS

<Variant L-Amino Acid Oxidase>

Figure 1:
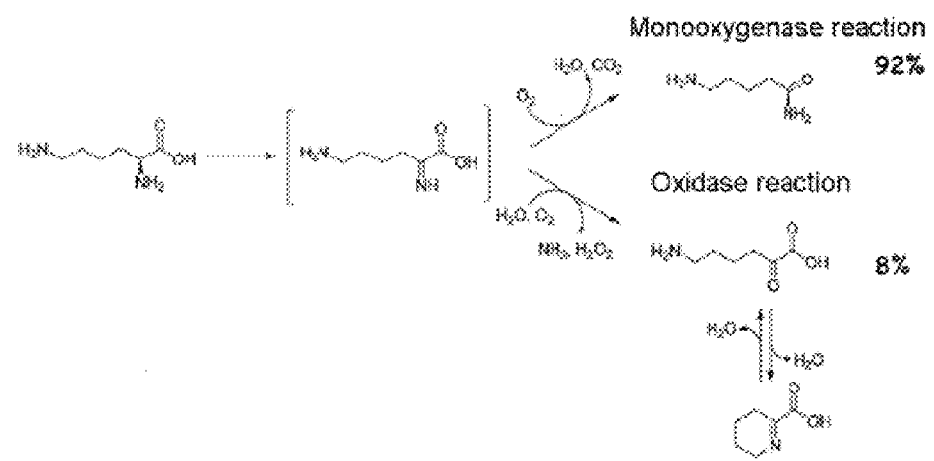
FIG. 1 shows the reaction mechanisms and proportions of the monooxygenase reaction and oxidase reaction with L-lysine as substrate that are catalyzed by L-amino acid oxidase derived from *Pseudomonas* sp. H-8-1-3 (wild-type enzyme).

The present invention relates to proteins such as those described herein, including a protein having the amino acid sequence of SEQ ID NO: 2, but wherein the cysteine at position 254 is replaced with methionine, phenylalanine, tyrosine, tryptophan, alanine, glycine, valine, isoleucine, leucine, lysine, arginine, histidine, aspartic acid, glutamic acid, serine, threonine, asparagine, glutamine, or proline, variants of such a protein, in which one or a plurality of amino acids other than the 254th amino acid, or a region containing the 254$^{th}$ amino acid, have been deleted, substituted, and/or added, wherein the variants can have at least 67% sequence identity. The variant proteins can have oxidase activity with higher substrate specificity for L-lysine than the amino acid oxidase consisting of the amino acid sequence denoted by SEQ. ID NO: 2.

The protein having the amino acid sequence denoted by SEQ. ID NO: 2 was obtained by separating for the first time a bacterial strain of genus *Pseudomonas* from the natural world, and cloning the gene coding for the L-amino acid oxidase produced by the microorganism belonging to the genus *Pseudomonas*. This point will be described in detail in the Examples.

The protein consisting of the amino acid sequence denoted by SEQ. ID NO: 2, as confirmed in the Examples, is a protein having L-amino acid oxidase activity. The L-amino acid oxidase activity of the protein is one that acts on L-lysine, L-ornithine, and L-arginine at pH of 7.0 (30° C.) in the presence of oxygen and water, producing hydrogen peroxide and ammonia. In the present description, the oxidase activity on L-lysine, L-ornithine, and L-arginine will be separately referred to as L-lysine oxidase activity, L-ornithine oxidase activity, and L-arginine oxidase activity. These oxidase activities can be measured using the measurement reagents and measurement methods described in the Examples.

The protein as described herein can be a variant L-amino acid oxidase that can be obtained by replacing the cysteine at position 254 in the amino acid sequence denoted by SEQ. ID NO: 2 with methionine, phenylalanine, tyrosine, tryptophan, alanine, glycine, valine, isoleucine, leucine, lysine, arginine, histidine, aspartic acid, glutamic acid, serine, threonine, asparagine, glutamine, or proline. The protein obtained by replacing the 254th amino acid with these amino acids, as is indicated in the Examples, exhibits higher specificity of oxidase activity on L-lysine than the amino acid oxidase consisting of the amino acid sequence denoted by SEQ. ID NO: 2.

The protein having "oxidase activity with higher substrate specificity for L-lysine than the amino acid oxidase consisting of the amino acid sequence denoted by SEQ. ID NO: 2" can refer to a protein of relatively higher substrate specificity for L-lysine than the wild-type amino acid oxidase ("wild-type enzyme" hereinafter). Specifically, this means that compared to the wild-type enzyme, the ratio of L-arginine oxidase activity to L-lysine oxidase activity is lower, the ratio of the L-ornithine oxidase activity to L-lysine oxidase activity is lower, or both the ratio of L-arginine oxidase activity to L-lysine oxidase activity and the ratio of L-ornithine oxidase activity to L-lysine oxidase activity are lower. The protein having "oxidase activity with higher substrate specificity for L-lysine than the amino acid oxidase consisting of the amino acid sequence denoted by SEQ. ID NO: 2," from the perspective of a higher substrate specificity for L-lysine can be a protein in which both the ratio of L-arginine oxidase activity to L-lysine oxidase activity, and the ratio of L-ornithine oxidase activity to L-lysine oxidase activity, are lower than in the above wild-type enzyme.

From the perspective of imparting "oxidase activity with higher substrate specificity for L-lysine" than the wild-type enzyme, the 254th amino acid in the protein as described herein can be methionine, phenylalanine, tyrosine, alanine, valine, isoleucine, leucine, aspartic acid, glutamic acid, or serine. That is because when the 254th amino acid is replaced with one of these amino acids, as indicated in the Examples below, both the ratio of L-arginine oxidase activity to L-lysine oxidase activity and the ratio of L-ornithine oxidase activity to L-lysine oxidase activity are lower than those of the wild-type enzyme. In addition, from the perspective of obtaining a protein (amino acid oxidase) in which the substrate specificity of the oxidase activity to L-lysine is markedly enhanced, the 254th amino acid can be isoleucine or tyrosine.

Within the ranges as described herein, the protein of the present invention is not specifically limited so long as it has oxidase activity with high substrate specificity for L-lysine. When the L-lysine oxidase activity of the protein is defined as 100%, the L-arginine oxidase activity of the protein can be 15% or lower, 10% or lower, 5% or lower, 4% or lower, 3% or lower, 2% or lower, 1% or lower, 0.5% or lower, 0.01% or lower, or 0%. Additionally, the L-ornithine oxidase activity of the protein can be 80% or less, 60% or less, 50% or less, 20% or less, 15% or less, 10% or less, 5% or less, 4% or less, 3% or less, 2% or less, 1% or less, 0.5% or less, 0.01% or less, or 0%. In this connection, in the case of the wild-type enzyme serving as a reference, when the L-lysine oxidase activity at pH 7.0 and 30° C. is defined as 100%, the L-arginine oxidase activity can be about 20% and the L-ornithine oxidase activity is about 83%.

So long as the protein of the present invention exhibits the "oxidase activity of high substrate specificity for L-lysine" set forth above, the absolute value of the L-lysine oxidase activity is not specifically limited. For example, the L-lysine oxidase activity of the protein of the present invention can be at least equivalent to or greater than the L-lysine oxidase activity of the wild-type enzyme. Specifically, the protein of the present invention, at pH 7.0, can have an L-lysine oxidase activity of 0.6 U/mg or greater, or 1.0 U/mg or greater.

The variant L-amino acid oxidase as described herein does not exhibit activity toward L-tyrosine, L-alanine, L-cysteine, L-aspartic acid, L-glutamic acid, glycine, L-histidine, L-isoleucine, L-leucine, L-methionine, L-asparagine, L-proline, L-glutamine, L-serine, L-threonine, L-valine, L-phenylalanine, and L-tryptophan, which are constituent amino acids of proteins other than L-lysine, L-ornithine, and L-arginine.

In the present invention, the variant protein can be a protein in which the amino acid at position 254 is replaced, and in addition, one or a plurality of amino acids in a region excluding the 254th amino acid are deleted, substituted, and/or added, wherein the protein exhibits oxidase activity with higher substrate specificity for L-lysine than the amino acid oxidase consisting of the amino acid sequence denoted by SEQ. ID NO: 2. Here, the expression of "one or a plurality" is not specifically limited so long as oxidase activity with high substrate specificity for L-lysine is present. Since the proportion of proteins having oxidase activity with high substrate specificity for L-lysine is high, the range of "one or a plurality" is, for example, 1 to 30, 1 to 20, 1 to 10, 1 to 7, 1 to 5, 1 to 3 or 1 to 2, and can be about 1.

Additionally, the variant protein can be a protein having an amino acid sequence which has at least 67% sequence identity with the amino acid sequence of the protein of SEQ. ID NO: 2, and has oxidase activity with greater substrate specificity for L-lysine than the amino acid oxidase consisting of the amino acid sequence denoted by SEQ. ID NO: 2, wherein the amino acid corresponding to the 254th amino acid is methionine, phenylalanine, tyrosine, tryptophan, alanine, glycine, valine, isoleucine, leucine, lysine, arginine, histidine, aspartic acid, glutamic acid, serine, threonine, asparagine, glutamine, or proline.

The expression "sequence identity" is not specifically limited so long as the enzyme has oxidase activity with high substrate specificity for L-lysine. The sequence identity of the amino acid sequences is not specifically limited to 67% or greater. It can be 68% or more, 69% or more, 70% or more, 71% or more, 72% or more, 73% or more, or 74% or more. It can be 75% or more, 80% or more, 85% or more, or 90% or more. It is even more preferably 91% or more, 92% or more, 93% or more, 94% or more, 95% or more, 96% or more, 97% or more, 98% or more, 99% or more, or 99.5% or more. The expression "sequence identity" can mean a degree of identity of amino acids in two or more amino acid sequences relative to each other. Accordingly, the higher the degree of identity of two given amino acid sequences, the higher the identity or similarity of the sequences. Whether or not two amino acid sequences have similarity can be analyzed by direct comparison of the sequences. Specifically, it can be analyzed using commercial sequence analysis software.

The term "mutation" can mean, specifically, the deletion or substitution of amino acids. That is, the amino acid corresponding to the 254th amino acid in the amino acid sequence of the protein of SEQ ID NO: 2, can be deleted or substituted with the specified amino acids. Accordingly, so long as the amino acid that is substituted into the protein of SEQ ID NO: 2 above is isoleucine, the amino acid corresponding to the 254th amino acid in the amino acid sequence will be isoleucine.

In the third protein as described above, the amino acid corresponding to the 254th amino acid in the amino acid sequence of the protein of SEQ ID NO: 2, which can serve as the reference for determining sequence identity can be checked by the above-described sequence identity or homology. Specifically, using commercial sequence analysis software, by analyzing the alignment of the amino acid sequences that are the targets of analysis against the amino acid sequence of SEQ. ID NO: 2 or the amino acid sequence of the protein of (1) above, it is possible to search for the amino acid corresponding to the 254th amino acid. Such methods of alignment analysis are widely known to persons having ordinary skill in the art.

So long as the above protein of the present invention falls within the scope specified herein, the origin thereof is not specifically limited. For example, the protein of the present invention can be a recombinant protein fabricated with various genetic engineering techniques, a synthetic protein fabricated by chemical synthesis, or a protein produced by extracting or generating a protein that produces a variant after obtaining a variant capable of producing the variant enzyme of the present invention by subjecting a specific species of organism (such as a bacterium) having a genetic homologue to the L-amino acid oxidase consisting of the amino acid sequence denoted by SEQ. ID NO: 2 to a mutagen.

When producing the recombinant protein of the present invention by a genetic engineering technique, nucleic acid (DNA or RNA) coding for the above-described proteins can be prepared and combined into various expression vectors to express the protein of the present invention. In producing the nucleic acid coding for the protein of the present invention, amino acid substitutions, deletions, or addition or mutations can be achieved, for example, by the error-prone PCR method, DNA shuffling method, various site-specific mutagenic methods, or the like. By introducing the nucleic acid coding for the protein of the present invention that has been produced in this manner into a suitable expression system, it is possible to produce the protein of the present invention.

The expression system that can be used to produce the protein of the present invention is not specifically limited. However, by way of example, various expression vectors that are capable of expressing recombinant proteins in various species of organism (hosts) can be employed. Potential expression vectors that can be used include various expression vectors that are capable of expressing proteins in hosts such as microorganisms such as bacteria and fungi (for example, yeast), plants, insect cells, and mammalian cells. These can also be viral vectors (including phage vectors) and plasmid vectors. Alternatively, a cell-free protein expression system employing rabbit reticulocyte lysate, wheat germ lysate, *E. coli* lysate, or the like can be employed to fabricate the protein of the present invention.

When the protein of the present invention is being expressed in an expression system employing a host in the form of a specific species of organism, it can be prepared by a method comprising loading the nucleic acid coding for the protein of the present invention into a vector, using the vector to transform the host cell, culturing the transformed host cell to cause the protein coded for by the gene to accumulate in the culture solution, and collecting the accumulated protein.

The nucleic acid coding for the protein of the present invention, the vector containing the nucleic acid, and the transformant that is transformed by the vector are one embodiment of the present invention.

The method used to obtain the nucleic acid coding for the protein of the present invention is not specifically limited. For example, as described below in the Examples, the nucleic acid coding for the protein of the present invention can be obtained using a material in the form of nucleic acid coding for the L-amino acid oxidase gene (SEQ. ID NOS: 1 and 2) that has been isolated from *Pseudomonas* sp. H-8-1-3. Alternatively, nucleic acid coding for the protein of the present invention can be fabricated by isolating from various bacteria a gene with homology to the amino acid sequence (L-amino acid oxidase) described in SEQ. ID NO: 2 of the protein of the present invention, preparing nucleic acid coding for the gene, and conducting amino acid substitution corresponding to the 254th amino acid set forth above. Further, the nucleic acid coding for the protein of the present invention can be fabricated by any method known to persons having ordinary skill in the art, such as chemical synthesis, genetic engineering techniques, or mutagenesis based on information about the base pair sequence described in SEQ. ID NO: 1, the amino acid sequence described in SEQ. ID NO: 2, known base pair sequences having a certain identity to the base pair sequence described by SEQ. ID NO: 1, or known amino acid sequences having a certain identity to the amino acid sequence described in SEQ. ID NO: 2.

The amino acid sequence denoted by SEQ. ID NO: 2 is the amino acid sequence of L-amino acid oxidase (wild-type enzyme) derived from *Pseudomonas* sp. H-8-1-3 isolated by the present inventors from the natural world. However, a large number of genes exhibiting a certain homology with this L-amino acid oxidase are known. For example, genes derived from the bacteria shown in Table 1 are known.

TABLE 1

| Species | Name of gene (name of enzyme) | Accession No. | SEQ. ID NO. | Sequence identity with variant enzyme C254I | Amino acid corresponding to 254th amino acid |
|---|---|---|---|---|---|
| *Pseudomonas putida* | Lysine 2-monooxygenase | BAG54787.1 | SEQ. ID NO: 5 | 93.75% | No. 254 |
| *Pseudomonas entomophila* | Am inooxygenase | YP_606177.1 | SEQ. ID NO: 6 | 93.75% | No. 254 |
| *Pseudomonas fluorescens* Pf-5 | Monoamine oxygenase | YP_262728.1 | SEQ. ID NO: 7 | 92.5% | No. 254 |
| *Pseudomonas fluorescens* F113 | Lysine 2-monooxygenase | ACT32386.1 | SEQ. ID NO: 8 | 91.07% | No. 254 |
| *Pseudomonas fluorescens* Pf-5 | Tryptophan 2-monooxygenase | YP_350882.1 | SEQ. ID NO: 9 | 90.18% | No. 254 |
| *Pseudomonas fluorescens* WH6 | Tryptophan 2-monooxygenase | ZP_07777919.1 | SEQ. ID NO: 10 | 88.18% | No. 261 |
| *Pseudomonas syringae* pv. Lachrymans str. M3022780PT | Tryptophan 2-monooxygenase | EGH95128.1 | SEQ. ID NO: 11 | 88.39% | No. 253 |
| Alpha proteobacterium BAL199 | Tryptophan 2-monooxygenase | ZP_02189967.1 | SEQ. ID NO: 12 | 72.73% | No. 254 |
| *Pseudonocardia* sp. P1 | Tryptophan 2-monooxygenase | ZP_08123759.1 | SEQ. ID NO: 13 | 70.54% | No. 247 |
| *Gordonia amarae* NBRC 15530 | Aminooxidase | ZP_09216582.1 | SEQ. ID NO: 14 | 67.91% | No. 246 |
| *Roseobacter denitrificans* Och 114 | Tryptophan oxygenase | YP_681814.1 | SEQ. ID NO: 15 | 67.86% | No. 243 |
| *Mycobacterium abscessus* ATCC 19977 | Tryptophan 2-oxygenase | YP_001701566.1 | SEQ. ID NO: 16 | 68.81% | No. 254 |

Figure 4:
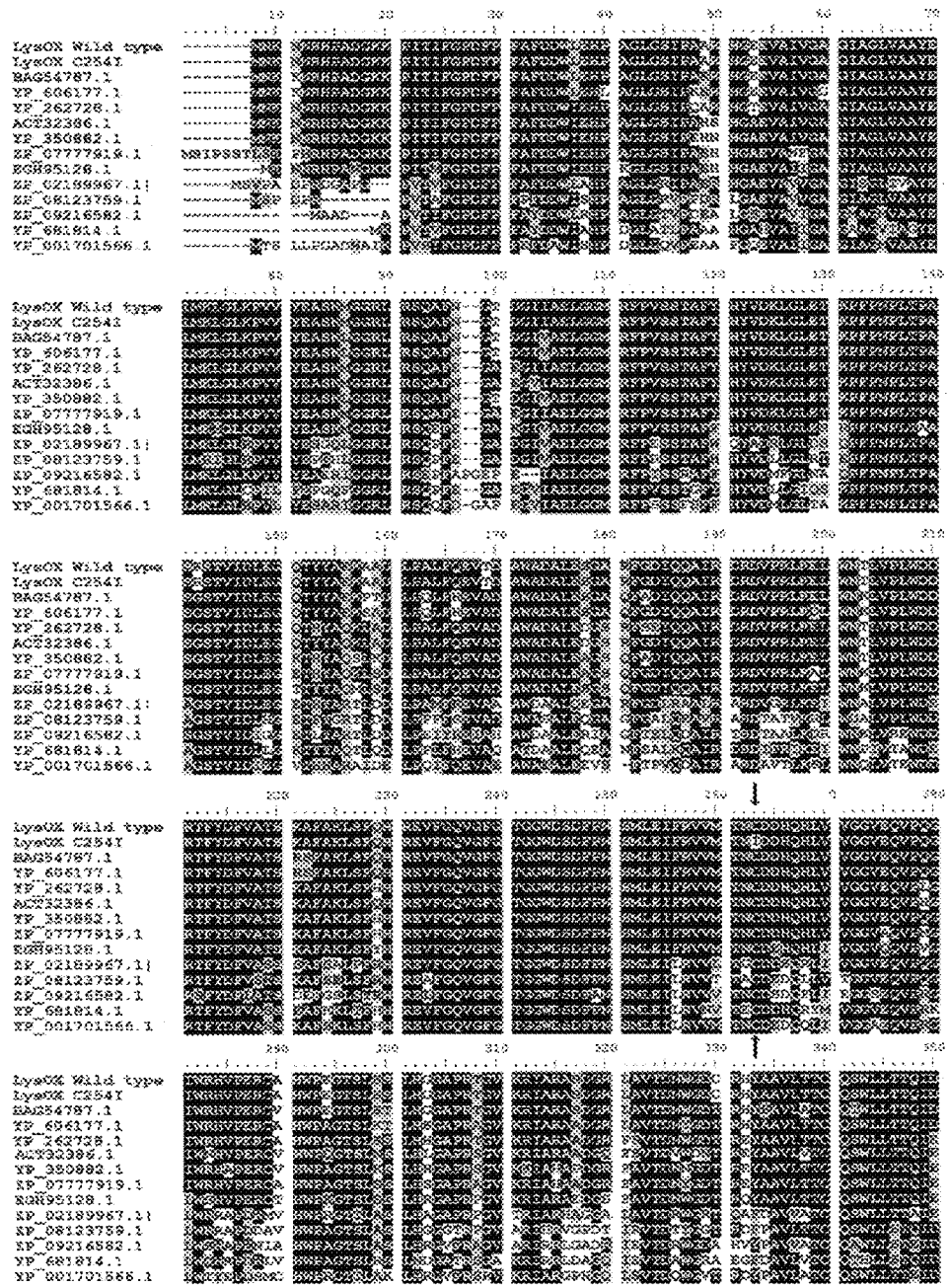
FIG. 4-4a show the results of an alignment analysis of the amino acid sequence of the above wild-type enzyme, the amino acid sequence of the variant enzyme C254I, and the amino acid sequence of a known homologue gene.
Figure 4A:
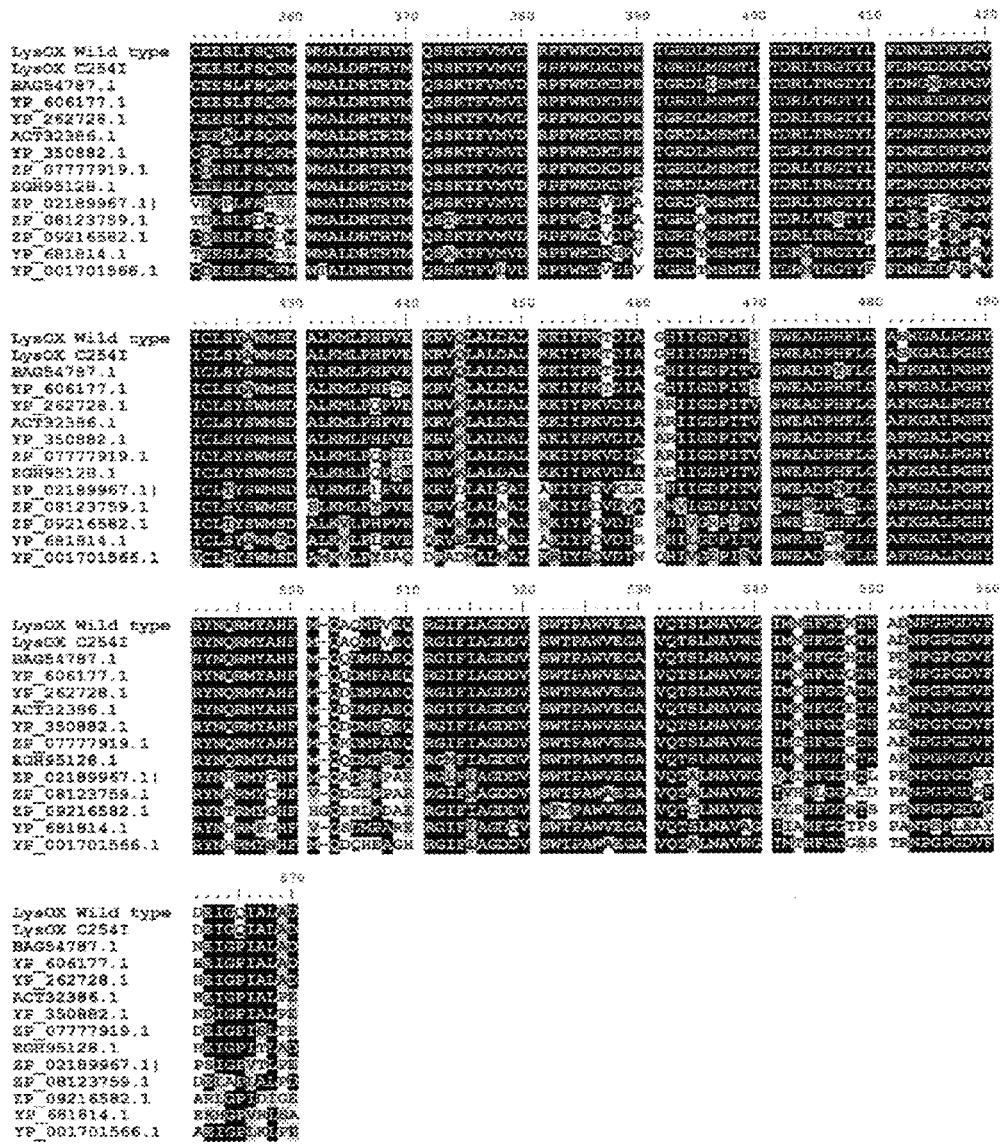

The results of an alignment analysis of the amino acid sequence of wild-type enzyme, the amino acid sequence of the variant enzyme C254I and the amino acid sequence of known genes shown in Table 1 are provided in FIGS. 4-4a. In FIGS. 4-4a, the amino acid at the position indicated by the arrow corresponds to the 254th amino acid. As shown in FIG. 4-4a, in the same manner as the wild-type enzyme, in the known genes shown in Table 1, the amino acid corresponding to the 254th amino acid is cysteine. The amino acid sequence of the protein of the present invention can be designed based on the sequences of these known genes, or designed based on the sequence information of other known homologous genes.

Specifically, the nucleic acid coding for the protein of the present invention can be prepared using the method of contacting DNA having the base pair sequence given by SEQ. ID NO: 1 of the SEQUENCE LISTING, for example, with a reagent serving as a mutagen, the method of irradiation with ultraviolet radiation, genetic engineering methods, and the like. The site-specific mutagenic method, a type of genetic engineering method, can be a method permitting the introduction of a mutation at a specific position. Thus, it is useful to introduce a mutation at a specific site in a nucleic acid when producing a nucleic acid coding for the protein of the present invention.

For example, it is possible to prepare nucleic acid serving as a material for fabricating nucleic acid coding for the protein of the present invention by preparing suitable probes and primers based on information about the base pair sequence given in SEQ. ID NO: 1 or the amino acid sequence given in SEQ. ID NO: 2 of the SEQUENCE LISTING in the present Description, and using them to screen cDNA of bacteria including the strain *Pseudomonas* sp. H-3-1-3 or a genome library. The cDNA or genome library can be prepared by the conventional methods.

Material for preparing nucleic acid coding for the protein of the present invention can also be obtained by the PCR method. For example, a genome library, cDNA, or genomic DNA of bacteria including *Pseudomonas* sp. H-8-1-3 can be employed as template and PCR can be conducted using a pair of primers designed to amplify the base pair sequence given by SEQ. ID NO: 1. The PCR reaction conditions can be suitably set. An example of conditions is 30 cycles of a reaction process consisting of 30 seconds at 94° C. (denaturation), 30 seconds to 1 minute at 55° C. (annealing), and 2 minutes at 72° C. (elongation), followed by a 7 minute reaction at 72° C. The DNA fragment being amplified can be employed as the material for fabricating the nucleic acid coding for the protein of the present invention. Further, a vector obtained by cloning the amplified DNA fragment in a vector suited to amplification in a host such as *E. coli* can also be employed as the material for fabricating the nucleic acid coding for the protein of the present invention.

The nucleic acid coding for the protein of the present invention, or a vector containing this nucleic acid, can be fabricated by substituting base pairs by various mutagenic methods into the base sequence (codon) coding for the amino acid corresponding to the 254th amino acid in the material for fabricating the nucleic acid coding for the protein of the present invention that has been prepared as set forth above. The operations of preparing the above probe or primers, constructing a genome library, screening the genome library, and cloning the target gene are known to persons having ordinary skill in the art.

The nucleic acid coding for the protein of the present invention can be employed after having been inserted into a suitable vector. The type of vector that is employed in the present invention is not specifically limited. For example, an independently replicating vector (such as a plasmid) will do, as will a vector that recombines into the genome of a host cell in the course of being introduced into the host cell, and is replicated along with the chromosome into which it has recombined. The vector is desirably an expression vector. In an expression vector, elements (such as promoters) that are essential for transcription are functionally linked to the above nucleic acid. A promoter is a DNA sequence that exhibits transcription activity in a host cell, and can be suitably selected based on the type of host cell.

Examples of promoters that can function in bacterial cells are promoters of the *Geobacillus stearothermophilus* maltogenic amylase gene, *Bacillus licheniformis* alpha-amylase gene, *Bacillus amyloliquefaciens* BAN amylase gene, *Bacillus subtilis* alkaline protease gene, and *Bacillus pumilus* xylosidase gene; phage lambda $P_R$ or $P_L$ promoters, and lac, trp and tac promoters of *E. coli*.

Examples of promoters that function in mammalian cells are the SV40 promoter, MT-1 (metallothionein gene) promoter, or the adenovirus 2 major late promoter. Examples of promoters that function in insect cells are the polyhedrin promoter, P10 promoter, *Autographa californica* polyhedrosis basic protein promoter, Baculovirus immediate early gene 1 promoter, and the Baculovirus 39K delayed-early gene promoter. Examples of promoters that are capable of functioning in yeast host cells are promoters derived from yeast glycolytic genes, alcohol dehydrogenase gene promoters, TPI1 promoters, and ADH2-4-c promoters. Examples of promoters that function in filamentous fungal cells are ADH3 promoters and tpiA promoters.

In the above vectors, the nucleic acid coding for the protein of the present invention can be functionally bound to a suitable terminator as needed. The vector containing the nucleic acid coding for the protein of the present invention can also have elements such as polyadenylation signals (such as those derived from SV40 or the adenovirus 5E1b region) and transcription enhancing sequences (such as the SV40 enhancer). A recombinant vector containing the L-amino acid oxidase gene can also comprise a DNA sequence enabling replication of the vector within the host cell. One example is the SV40 replication origin (when the host cell is a mammalian cell).

The vector containing the nucleic acid coding for the protein of the present invention can also contain selection markers. Examples of selection markers are a gene the complement of which is lacking in the host cell, such as the dihydrofolate reductase (DHFR) or the *Schizosaccharomyces pombe* TPI gene, or a gene imparting resistance to a drug such as ampicillin, kanamycin, tetracycline, chloramphenicol, neomycin, or hygromycin. The methods of splicing the nucleic acid coding for the protein of the present invention, the promoters, and as needed, terminators and/or secretion signal sequences and inserting them into suitable vectors are widely known to persons having ordinary skill in the art.

The vector containing the nucleic acid coding for the protein of the present invention can be introduced into a suitable host to fabricate the transformant of the present invention. The host cell into which the vector of the present invention is introduced can be any cell in which the vector of the present invention can be replicated. When a transformant expressing the protein of the present invention is being fabricated, in addition to vector replication, it must be a cell that is capable of expressing the protein of the present invention. Examples of such host cells are bacteria, yeast, fungi, and higher eukaryotic cells.

Examples of bacterial cells are Gram-positive bacteria such as *Bacillus* and *Streptococcus*, and Gram-negative bacteria such as *E. coli*. The transformation of the bacteria can be done by the protoplast method, or using competent cells, which is a known method. Examples of mammalian cells are HEK293 cells, HeLa cells, COS cells, BHK cells, CHL cells, and CHO cells. Methods of transforming mammalian cells and expressing the DNA sequence that has been introduced into the cells are also known. For example, the electroporation method, calcium phosphate method, and lipofection method can be employed.

Examples of yeast cells are cells belonging to *Saccharomyces* and *Schizosaccharomyces*, such as *Saccharomyces cerevisiae* and *Saccharomyces kluyveri*. Examples of methods of introducing recombinant vectors into a yeast host are the electroporation method, spheroplast method, and lithium acetate method.

Examples of other fungal cells are cells belonging to the filamentous fungi such as *Aspergillus, Neurospora, Fusarium*, and *Trichoderma*. When employing a filamentous fungi as host cell, it is possible to conduct transformation by obtaining a recombinant host cell by recombining a DNA construct into the host chromosome. The recombination of the DNA construct into the host chromosome can be conducted by known methods, such as homologous recombination or heterogeneous recombination.

When employing an insect cell as a host, a vector into which a recombinant gene has been introduced and a Baculovirus can be jointly introduced into an insect cell to obtain a recombinant virus in the supernatant of an insect cell culture, and then infecting insect cells with the recombinant virus and inducing protein expression.

For example, the *Autographa californica* nuclear polyhedrosis virus, a virus that infects insects of the family Noctuidae, or the like can be employed.

Sf9 and Sf21, which are *Spodoptera frugiperda* of the Noctuidae, and HiFive (manufactured by Invitrogen), which are ovarian cells of *Trichoplusia ni*, can also be employed as insect cells.

For example, the calcium phosphate method or the lipofection method can be used to jointly introduce a recombinant gene vector and the above Baculovirus into an insect cell to prepare a recombinant virus.

The above transformant is cultured in a suitable nutrient medium under conditions permitting the replication of the vector of the present invention or under conductions permitting expression of the protein of the present invention. When expressing the protein of the present invention, the usual protein isolation and purifying methods can be used to isolate and purify the protein of the present invention from the culture product (containing the transformant and culture medium) of the transformant. For example, when the protein of the present invention is expressed in a dissolved state within the cell, following the end of culturing, the cells are recovered by centrifugation, suspended in an aqueous buffer, and crushed in an ultrasonic crusher to obtain a cell-free extract. The cell-free extract is then centrifuged. The protein of the present invention can be obtained as a purified preparation from the supernatant using just one or a combination of the usual protein isolating and purifying methods, such as the solvent extraction method, salting out with ammonium sulfate or the like, desalination method, precipitation with an organic solvent, anion-exchange chromatography employing a resin such as diethylaminoethyl (DEAE) Sepharose, cation-exchange chromatography employing a resin such as S-Sepharose FF (made by Pharmacia Co.), hydrophobic chromatography employing a resin such as butyl Sepharose or phenyl Sepharose, gel filtration with a molecular sieve, affinity chromatography, the chromatofocussing method, and electrophoresis such as isoelectric point electrophoresis.

<Method of Quantifying L-Lysine>

The method of quantifying L-lysine in the present invention can include the following steps:

(A) maintaining a specimen and the protein according to the present invention in the presence of water and oxygen; and (B) detecting or quantifying at least one reaction product produced in the reaction solution by the effect of the oxidase activity of the protein on L-lysine.

In the method of the present invention, the biological sample that is employed as the specimen can be any sample potentially containing L-lysine. The biological sample is subjected to the action of the protein of the present invention, and some product thereof is quantified to measure the concentration of L-lysine in the biological sample, making it possible to suitably select biological samples. For example, when using a color-developing agent or a fluorescent agent to quantify the product, a colorless aqueous solution is desirable, with blood serum and blood plasma being examples.

Reaction scheme A below gives the oxidation reaction of L-lysine by the protein of the present invention.

Scheme A

Chem. 1

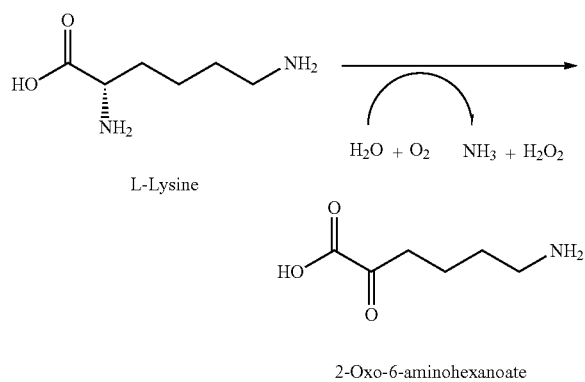

The above protein employed in the method of the present invention catalyzes the reaction given by Scheme A above.

Step (A)

The quantity of protein of the present invention that is admixed in step (A) is suitably 10 mU/mL or greater (a quantity of enzyme exhibiting activity such that it consumes 1 μmol of lysine in one minute is denoted as 1 U). The quantity of water that is admixed can be suitably determined based on the concentration of lysine in the sample, but normally falls within a range of 5 to 95%, for example. There is not a specific upper limit to the quantity of protein of the present invention that is admixed. In practical terms, it can be 100 mU/mL or less, for example. However, there is no intent to limit the quantities of the protein of the present invention and water that are added to these ranges, and they can be suitably adjusted.

In addition to water and the protein of the present invention, a reaction buffer is also desirably incorporated. The pH of the reaction buffer is not specifically limited so long as the oxidase activity with high substrate specificity for L-lysine of the above protein of the present invention is ensured. It can be suitably adjusted taking into account the relation between the optimal pH for oxidase activity on L-lysine and the substrate specificity for L-lysine. For example, it can be set to within a range of from pH 1.0 to 14 by taking into account the properties of the various enzymes to ensure oxidase activity on L-lysine and high substrate specificity for L-lysine that permits the detection of L-lysine. When employing the variant enzyme C254I described in the Examples below, taking into account a range yielding an oxidase activity with high substrate specificity for L-lysine, the pH of the reaction buffer can be adjusted, for example, to within a range of pH 6.0 to 10.5, pH 6.5 to 10, pH 7 to 9, oe, pH 7.0 to 8.0.

The reaction solution obtained by the above mixing is maintained for a prescribed period in the presence of oxygen. In the L-lysine oxidation reaction based on the protein of the present invention, as shown in reaction Scheme A, 2-oxo-6-aminohexanoic acid, which is an L-lysine deamination product, ammonia ($NH_3$), and hydrogen peroxide ($H_2O_2$) are obtained as products. By conducting the reaction in air, the oxygen is supplied as oxygen dissolved in the reaction solution. It is normally not necessary to forcefully supply an oxygen-containing gas such as air to the reaction solution to supply oxygen to the reaction solution. A trace amount of oxygen is required for the enzymatic reaction based on the protein of the present invention, which is adequately covered by dissolved oxygen. The maintenance time for the enzyme reaction will depend on the quantity of enzyme employed (quantity of protein of the present invention), for example, and can range from 10 minutes to an hour, for example. Additionally, so long as the catalytic reaction based on the protein of the present invention that is shown in reaction Scheme A can take place when L-lysine is present in the specimen, the maintenance temperature of the enzyme reaction is not specifically limited. It can be constant over the maintenance period, or can vary. The maintenance temperature will depend on the optimal temperature of the enzyme employed (the protein of the present invention) and the substrate specificity for L-lysine that is exhibited at that temperature, for example. A suitable reaction temperature can be selected from within a range of 10 to 60° C.; for example, a range of 20 to 55° C., or a range of 25 to 40° C., can be employed. However, there is no intent to limit the retention time and retention temperature to these ranges, and they can be suitably adjusted as needed.

Step (B)

In step (B), at least one of the reaction products that is present in the reaction solution due to the action of the protein of the present invention following maintenance in step (A) is detected or quantified.

When the product that is used in detection or quantification is hydrogen peroxide, for example, a known method such as a peroxidase reaction can be used for measurement, making it possible to detect or quantify the hydrogen peroxide. When employing a peroxidase reaction for measurement, it suffices for the peroxidase employed to be an enzyme that can be used to detect or quantify hydrogen peroxide. An example is peroxidase derived from horseradish. It is also possible to use a color-developing agent that is capable of serving as a substrate for the peroxidase employed. When employing peroxidase derived from horseradish, an example is 4-aminoantipyrine: phenol. The reaction for detecting or quantifying hydrogen peroxide employing peroxidase derived from horseradish is as indicated below.

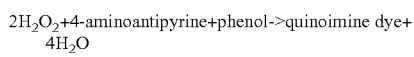

Chem. 2:

Color-developing agents and fluorescence agents such as 4-aminoantipyrine can be suitably selected based on the type of peroxidase employed.

The hydrogen peroxide that is the product of the L-amino acid oxidase reaction based on the protein of the present invention can be detected with a current detection sensor employing a hydrogen peroxide electrode. An example of a hydrogen peroxide electrode is a sensor employing an electrode in the form of a membrane upon which peroxidase and bovine serum albumin have been immobilized with glutaraldehyde, with ferrocene incorporated into a carbon paste.

When the product that is used for detection or quantification is ammonia, detection can be conducted with an ammonia-detecting agent. An example of an ammonia-detecting agent is the indophenol method in which phenol and hypochlorous acid are combined. Specifically, the sample is mixed with a phenol nitroprusside solution and a perchloric acid solution, developing color. Absorbance at 635 nm is measured, permitting the detection or quantification of ammonia.

When the product used for detection or quantification is 2-oxy-6-aminohexanoic acid, which is a deamination product of L-lysine, the 2-oxo-6-aminohexanoic acid reacts with 3-methyl-2-benzothiazolone hydrazine hydrochloride, making it possible to quantify the 2-oxo-6-aminohexaonic acid by spectrally quantifying hydrazone derivatives.

<The L-Lysine Quantification Kit>

The present invention further includes a kit for detecting or quantifying L-lysine, containing the above protein of the present invention.

The kit of the present invention can contain a reaction buffer, hydrogen peroxide-detecting reagent, ammonia-detecting agent, and at least one agent for detecting 2-oxy-6-aminohexanoic acid, which is an L-lysine deamination product.

The reaction buffer is used to maintain a pH suited to the enzymatic reaction by the protein of the present invention in the reaction solution. The pH of the reaction buffer solution is not specifically limited so long as the oxidase activity with high substrate specificity for L-lysine of the protein of the present invention is ensured. It can be suitably adjusted taking into account the relation between the optimal pH of oxidase activity on L-lysine and substrate specificity for L-lysine. For example, a range ensuring the oxidase activity on L-lysine and high substrate specificity permitting the detection of L-lysine can be set within the range of pH 1.0 to 14 taking into account the properties of the various enzymes. When variant enzyme C245I described in the Examples below is used, taking into account a range yielding oxidase activity with high substrate specificity for L-lysine, the pH of the reaction buffer can be adjusted to, for example, a range of pH 6.0 to 10.5, pH 6.5 to 10, pH 7 to 9, andor, pH 7.0 to 8.0.

A hydrogen peroxide-detecting reagent is employed when detecting hydrogen peroxide by color development or fluorescence, for example. Examples of hydrogen peroxide-detecting reagents are combinations of peroxidase and a color-developing agent that is capable of using it as a substrate. A specific example is a combination of horseradish peroxidase and 2-aminoantipyrine phenol.

An example of an ammonia-detecting agent is the indophenol method based on a combination of a phenol and hypochlorous acid.

As a reagent for detecting 2-oxo-6-aminohexanoic acid, which is a deamination product of L-lysine, for example, 2-oxo-6-aminohexanoic acid and 3-methyl-2-benzothiazolone hydrazine hydrochloride can be reacted and the method of spectrally quantifying the hydrazone derivatives can be used.

<The Enzyme Sensor>

The present invention includes an L-lysine-detecting or quantifying enzyme sensor that includes an electrode for detecting hydrogen peroxide, wherein the protein of the present invention is disposed on the surface or in the vicinity of the electrode for detecting hydrogen peroxide.

The detection electrode is an electrode that detects hydrogen peroxide. The hydrogen peroxide-detecting electrode can be an enzymatic hydrogen peroxide electrode or a diaphragm-type hydrogen peroxide electrode. The protein of the present invention reacts with L-lysine to produce hydrogen peroxide. Thus, the hydrogen peroxide can be detected by a hydrogen peroxide-detecting electrode. By way of example, the enzymatic hydrogen peroxide electrode can be in the form of a sensor employing an electrode in the form of a membrane upon which peroxidase and bovine serum albumin have been immobilized with glutaraldehyde, with ferrocene incorporated into a carbon paste. The diaphragm hydrogen peroxide electrode is a type of electrode in which an electrode reacting with hydrogen peroxide is separated by a membrane.

The protein of the present invention is desirably disposed on the surface of the detection electrode or in the vicinity of the detection electrode. When disposed on the surface of the detection electrode, it can be immobilized, or not immobilized, on the surface of the detection electrode. Immobilization on the surface of the detection-use electrode is advantageous in that the sensor of the present invention can be repeatedly used.

The present invention will be specifically described based on the following non-limiting Examples.

EXAMPLES

In the Examples, the active measurement reagents and L-lysine measuring reagent composition are prepared by the following composition. The measurement conditions were as set forth below. The activity of the L-amino acid oxidase was measured as set forth below.

(1) Preparation of L-Amino Acid Oxidase Activity Measuring Reagent

TABLE 2

| Activity measuring reagents | |
|---|---|
| Horseradish peroxidase | 0.66 U |
| Substrate* | 40 mM |
| 4-Aminoantipyrine | 0.005% |
| TOOS (N-ethyl-N-(2-hydroxy-3-sulfopropyl)-3-methylaniline, sodium salt, dehydrate) | 0.03% |
| 40 mM potassium phosphate buffer solution (pH 7.0) | |

TABLE 3

| Amino acids employed | | | | | |
|---|---|---|---|---|---|
| L-Lys | L-Cys | L-Arg | L-Asn | L-Asp | L-Tyr |
| L-Gln | L-Glu | L-Ala | L-Leu | L-Ile | D-Lys |
| L-Val | L-Phe | L-His | L-Trp | L-Pro | D-Arg |
| L-Ser | L-Met | L-Thr | L-Ornithine | Gly | D-Ornithine |

(2) Method Measuring the Activity of L-Amino Acid Oxidase

The activity of L-amino acid oxidase was determined by the colorimetric method using the color-developing solutions of Table 2 from the quantity of hydrogen peroxide produced in the oxidation of L-amino acid. When measuring activity with microplates, to 100 μL of color-developing solution were added 100 μL of 100 mM solutions of the amino acids shown in Table 3 and 50 μL of enzyme solution. After dispensing on ice, reactions were conducted for 0, 0.5, 1, 1.5, 2, 3, 4, and 5 hours at 30° C. A microplate reader was then used to measure the absorbance at 550 nm. For the substrates with L-amino acid oxidase activity, the 20 types of amino acid (100 mM solutions) shown in Table 3 were employed. For blanks, 100 mM potassium phosphate buffer solution (pH 7.0) was added instead of the substrate.

In measurement with an absorption spectrometer with 1 cm quartz cells in enzyme purification, a 1 mL total quantity of reaction solution was employed. Based on the change in absorbance obtained, the L-lysine oxidase enzymatic activity was calculated with the calculation equation given below. A quantity of enzyme that yielded one micromol of substrate per minute under the above conditions was defined as 1 U. Based on the change in absorbance obtained, the enzymatic activity of the L-amino acid oxidase was calculated from the calculation equation given below.

(3) Equation for Calculating L-Amino Acid Oxidase Activity $$\text{Activity level (U/mL)} = \{\Delta OD/\min(\Delta OD\text{test}-\Delta OD\text{blank}) \times 3.1 \text{ (mL)} \times \text{dilution rate}\}/\{13 \times 1.0 \text{ (cm)} \times 0.1 \text{ (mL)}\}$$

3.1 (mL): Total quantity of solution
13: Millimolar extinction coefficient
1.0 cm: Length of optical path of cell
0.1 (mL): Amount of enzyme sample solution (4) Enzyme Purification of *Pseudomonas* Sp. H-8-1-3-Derived L-Amino Acid Oxidase Method of Culturing *Pseudomonas* Sp. H-8-1-3

*Pseudomonas* sp. H-8-1-3 was precultured by being inoculated onto 5 mL of TGY medium (0.5% polypeptone, 0.5% yeast extract, 0.1% $KH_2PO_4$, 0.1% D-glucose, pH 7.0) and cultured for 12 hours at 30° C. and 200 rpm. Subsequently, it was inoculated onto a two-liter Sakaguchi flask containing 500 mL of TGY medium and cultured for 48 hours at 30° C. and 96 rpm. Following culturing, the product was centrifuged for 20 minutes at 5,000×g, yielding a bacterial mass.

(ii) Preparation of Cell-Free Extract

Strain H-8-1-3 was precultured (200 rpm, 30° C., 12 hours) in 5 mL of TGY medium. The precultured solution was inoculated onto 500 mL of TGY medium and cultured with shaking (96 rpm) for 2 days at 30° C. using two-liter Sakaguchi flasks (total 20 L). The bacteria were collected with a large centrifuge (5,000 rpm, 10 minutes, 4° C.), washed with physiological saline (0.9% NaCl), after which the bacterial mass of 5 liters of medium was suspended in 100 mL of 20 mM phosphate buffer solution (pH 7.0) (KPB). A 100 mL quantity of the bacterial solution was ultrasonically processed for 15 minutes and centrifuged (8,000 rpm, 20 minutes, 4° C.). The supernatant obtained was employed as the cell-free extract.

(iii) Processing with Protamine Sulfate to Remove Nucleic Acid

To the cell-free extract was added 0.5% of protamine sulfate sodium. After stirring the mixture for 30 minutes, it was centrifuged in a large centrifuge (3,000 rpm, 10 minutes, 4° C.) and the supernatant was recovered.

(iv) Ammonium Sulfate Fractionation

While stirring the cell-free extract, from which the nucleic acid had been removed, in ice with a stirrer, ammonium sulfate powder was added little by little to 30% saturation. After stirring for 30 minutes, the mixture was centrifuged (8,000 rpm, 10 minutes, 4° C.). While stirring the supernatant on ice, ammonium sulfate powder was added to 60% saturation. After stirring for 30 minutes, the mixture was centrifuged. Similarly, ammonium sulfate powder was added to 90% saturation and the mixture was centrifuged. The precipitates obtained from the various fractions (0 to 30% fraction, 30 to 60% fraction, and 60 to 90% fraction) were suspended in 10 mL of 20 mM KPB (pH 7.0) and dialyzed overnight in 5 L of the same buffer (×3 times).

(v) Anion-Exchange Column Chromatography (DEAE-Toyopearl)

A column was packed with 15 mL of DEAE-Toyopearl resin equilibrated with 20 mM KPB and the dialyzed 30 to 60% fraction of enzyme solution was adsorbed. The column was washed with 100 mL of 20 mM KPB, after which 200 mL of 20 mM KPB and 200 mL of 20 mM KPB containing 500 mM NaCl were used to gradually raise the NaCl concentration above gradient, causing the enzyme to elute. A fraction collector was used to collect each fraction in a 50 mL test tube. The fractions in which activity was found were collected and dialyzed overnight with the same buffer.

(vi) Hydroxyapatite Column Chromatography (GIGA-PITE)

A column was packed with 5 mL of GIGA-PITE resin equilibrated with 20 mM phosphate buffer and the enzyme solution was adsorbed. After washing the column with 50 mL of 20 mM KPB, 50 mL of 20 mM KPB and 200 mL of 500 mM KPB were employed to gradually raise the KPB concentration above gradient, causing the enzyme to elute. Non-adsorbing fractions in which activity was found were dialyzed overnight with 5 L of the same buffer (×3 times).

(vii) Strong Ion Exchange Chromatography (MonoQ HR 10/100)

Medium pressure high performance liquid chromatography (FPLC, column: 20 mM KPB-equilibrated MonoQ HR 10/100 column) was employed. A 200 µL quantity of enzyme solution concentrated by ultrafiltration (Centricon tube) was introduced into the sample loop, and the enzyme was eluted with an FPLC gradient system using the two solvents of 20 mM KPB and 20 mM KPB containing 0.5 mM NaCl. Those fractions (0.5 mL each) in which activity was found were collected and dialyzed overnight. Following dialysis, a Centricon was used to concentrate the enzyme solutions to 200 µL.

(viii) Gel Filtration Chromatography (Superdex 200 10/30)

Medium pressure high performance liquid chromatography (FPLC, column: Superdex 200 10/30 column equilibrated with 20 mM KPB containing 150 mM NaCl) was employed. A 200 µL quantity of enzyme solution was introduced into the sample loop, and the enzyme was eluted with an FPLC system using a solvent in the form of 20 mM KPB containing 150 mM NaCl. Those fractions in which activity was found were collected and dialyzed overnight.

Table 4 shows the quantities of protein and the enzyme activity in each purification step.

TABLE 4

| Step | Total protein (mg) | Total activity (munit) | Specific activity (munit/mg) | Yield (%) | Purification (fold) |
| --- | --- | --- | --- | --- | --- |
| (ii) Cell-free extract | 4,300 | 0.83 | 0.20 | — | — |
| (iii) Removal of nucleic acid | 3,700 | 1.11 | 0.30 | — | — |
| (iv) Ammonium sulfate fractionation (30-60%) | 1,100 | 3.30 | 3.03 | 100 | 1 |
| (v) DEAE-Toyopearl | 970 | 1.42 | 1.46 | 43 | 0.4 |
| (vi) Giga-pite (Flowthrough) | 700 | 0.57 | 0.82 | 17 | 0.3 |
| (vii) MonoQ 10/100 | 130 | 0.32 | 2.51 | 9 | 0.8 |
| (viii) Su perdex 200 10/30 | 9 | 0.31 | 35.0 | 9 | 11.6 |

(5) Determination of Molecular Weight of H-8-1-3-Derived L-Amino Acid Oxidase by SDS Polyacrylamide Gel Electrophoresis The electrophoretic gel employed consisted of a concentrated gel comprised of 0.5 mL of 36% polyacrylamide, 3.5 mL of 0.179M tris-HCl (pH 6.8), 0.5 mL of 1% SDS, 125 µL of 10% TEMED, and 375 µL of 2% APS layered over a gel comprised of 5.25 mL of 36% acrylamide, 8.25 mL of 0.68 M tris-HCl buffer (pH 8.8), 1.58 mL of 1% SDS, 187 µL of 10% TEMED, and 562.5 µL of 2% APS. A 10 µL quantity of purified enzyme sample mixed with an equal quantity of buffer (200 µL glycresol, 40 µL 1 M tris-HCl (pH 8.0), 360 µL water, 200 µL 2-mercaptoethanol, and 200 µL of 10% SDS) was subjected to electrophoresis at 30 mA in running buffer (tris 3.0 g, glycine 14.1 g, and SDS 10 g). Subsequently, it was stained for one hour with protein staining solution (CBB 2.5 g, methanol 500 mL, acetic acid 50 mL, and water 450 mL) and decolored with a destaining solution (methanol:acetic acid:water=3:1:6) until the bands became distinct.

Molecular weight markers (Bio-Rad) were employed in the form of phosphorylase (97,400), bovine serum albumin (66,267), aldolase (42,200), carbonic anhydrase (30,000), and soybean trypsin inhibitor (20,000).

Figure 2:
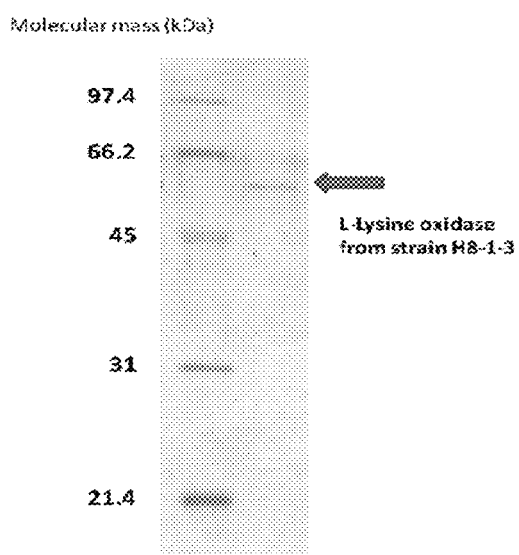
FIG. 2 is an SDS-PAGE photograph of the above wild-type enzyme.

FIG. 2 is an SDS-PAGE photo of *Pseudomonas* sp. H-8-1-3-derived L-amino acid oxidase (wild-type enzyme).

(6) Determining the N-Terminal Amino Acid Sequence of *Pseudomonas* Sp. H-8-1-3-Derived L-Amino Acid Oxidase Eight residues from the N-terminal of the purified *Pseudomonas* sp. H-8-1-3-derived L-amino acid oxidase were determined by the Edman degradation procedure.

(7) Cloning of the *Pseudomonas* Sp. H-8-1-3-Derived L-Amino Acid Oxidase Gene (i) Extraction of Chromosomal DNA from *Pseudomonas* Sp. H-8-1-3

*Pseudomonas* sp. H-8-1-3 was inoculated onto 3 mL of TGY medium and cultured for 12 hours at 30° C. and 200 rpm. The cells were collected by centrifuging (15,000 rpm, 5 minutes, 4° C.) the bacterial mass from 1 mL of culture solution. After washing the cells with 1 mL of STE buffer (0.58 g of NaCl, 1 mL of 1 M tris-HCl (pH 8.0), and 200 µL of 0.5 M EDTA (pH 8.0) to which water was added to make 100 mL), the cells were suspended in the same buffer. They were heated for 15 minutes at 68° C. and centrifuged (15,000 rpm, 5 minutes, 4° C.). The supernatant was removed. The cells were suspended in 300 µL of lysozyme-RNase (lysozyme 5 mg and 10 mL of 10 mg/mL RNase per solution; dissolved in 1 mL of a solution of 0.9 g of glucose, 2.5 mL of 1 M tris-HCl (pH 8.0), 2 mL of 0.5 M EDTA (pH 8.0) to which ultrapure water was added to make 100 mL). Following incubation for 30 minutes at 37° C., 6 µL of proteinase K solution was added (10 mg/L proteinase K per mL of solution), the mixture was gently stirred, and the mixture was incubated for 10 minutes at 37° C. A 3 mg quantity of N-lauroylsarcosine was added. The mixture was gently stirred and then incubated for 3 hours at 37° C., and a phenol-chloroform treatment was gently conducted twice. To 300 µL of the supernatant were added 10 µL of 5 M NaCl solution and 600 µL of ethanol, the mixture was stirred, and centrifugation was conducted (15,000 rpm, 10 minutes, 4° C.). After washing with 70% ethanol, the product was air dried and dissolved in 100 µL of TE buffer, yielding the targeted chromosomal DNA.

(ii) Amplification of *Pseudomonas* Sp. H-8-1-3-Derived L-Amino Acid Oxidase Gene by PCR The composition of the PCR reaction solution was 35 µL of water, 5 µL of 10×Ex Taq buffer, 5 µL of 2 mM dNTP, 1 µL of 100 pmol primer 1 (5'-ATGAACAANAANAACCGCCAC-CCSGCCGAC-3') (SEQ. ID NO: 17), 1 µL of 100 pmol primer 2 (5'-TCARTCYGCCAGGGCGATYGGSC-CGATYTC-3') (SEQ. ID NO: 18), 2 µL of template DNA, and 1 µL of Ex Taq. The PCR reaction conditions were (i) 5 minutes at 98° C., (ii) 10 seconds at 96° C., (iii) 5 seconds at 50° C., (iv) 4 minutes at 60° C., and 31 cycles up to (ii). The amplified gene was confirmed by agarose gel electrophoresis. The amplified gene was extracted with a Gel-M gel extraction kit from Viogene (USA).

(iii) Sequencing *Pseudomonas* Sp. H-8-1-3-Derived L-Amino Acid Oxidase Gene

To sequence both strands of the gene, a sequencing reaction was conducted using primer 1, primer 2, primer 3 (5'-AGCACGGTAATCGATCTGGA-3') (SEQ. ID NO: 19), and primer 4 (5'-CATCGAGTGCCAGTTGCACG-3') (SEQ. ID NO: 20). The composition of the reaction solution was 1.6 µL of each primer, 1.6 µL of template DNA, 1 µL of BigDye premixed solution, 1.6 µL of 5× BigDye sequencing buffer, and 2.8 µL of sterilized water. A total quantity of 10 µL was employed. The PCR reaction conditions were (i) 2 minutes at 96° C., (ii) 10 seconds at 96° C., (iii) 5 seconds at 50° C., (iv) 4 minutes at 60° C., (v) 25 cycles of (ii) to (iv), and (vi) 5 minutes at 72° C. To the PCR product were added 1 µL of 3 M sodium acetate (pH 5.2), 1 µL of 0.125 M EDTA, and 25 µL of ethanol. The mixture was left standing for 15 minutes at room temperature and then centrifuged (15,000 rpm, 8 minutes, 4° C.) to induce precipitation. The supernatant was discarded, 10 µL of Hi Di Formamide was added, and the mixture was heated for 5 minutes at 100° C. The mixture was then rapidly cooled with ice water and the base sequence thereof was read with an ABI PRISM 310 Genetic Analyzer. The sequence data obtained were analyzed with Genetyx and the base sequences of fragments amplified with the various primers were linked. FIG. 3 shows the primary structure that was predicted from the base sequence of *Pseudomonas* sp. H-8-1-3-derived L-amino acid oxidase (wild-type enzyme).

(iv) Transformation of *E. coli* (*E. coli* JM 109) with the *Pseudomonas* Sp. H-8-1-3-Derived L-Amino Acid Oxidase Gene The composition of the ligation reaction was 5 µL of PCR product, 1 µL of pT7 Blue T-Vecter (Novagen), and 6 µL of ligation mix (Takara). The reaction was conducted for 30 minutes at 16° C. To 100 µL of competent cells of *E. coli* (*E. coli* JM 109) was added 12 µL of the ligation reaction solution and transformation was conducted by the heat shock method. Several colonies growing in LB medium (1.0% of polypeptone, 0.5% of yeast extract, and 1.0% of NaCl) containing 80 µg/mL of ampicillin were selected, extracted with plasmid, and subjected to 0.7% agarose electrophoresis to confirm the presence of the insert.

(8) Expression in *E. coli* (*E. coli* BL21) of *Pseudomonas* Sp. H-8-1-3-Derived L-Amino Acid Oxidase Gene (i) Amplification of *Pseudomonas* Sp. H-8-1-3-Derived L-Amino Acid Oxidase Gene PCR was conducted using the plasmids obtained in the above cloning as template DNA. The composition of the PCR reaction solution was 35 µL of water, 5 µL of 10×Ex Taq buffer, 5 µL of 2 mM dNTP, 1 µL of 100 pmol/µL primer 5 (5'-TATAATCATATGAACAAGAACAACCGCCA-3') (SEQ. ID NO: 21), 1 µL of 100 pmol/µL primer 6 (5'-TAT-TACTCGAGTCAGTCCGCCAGGGCGATTG-3') (SEQ. ID NO: 22), 100 ng of template DNA, and 5 units of Ex Taq. Primers 5 and 6 were provided with NdeI and XhoI restriction enzyme sites, respectively. The PCR reaction conditions were (i) 5 minutes at 98° C., (ii) 10 seconds at 96° C., (iii) 5 seconds at 50° C., (iv) 4 minutes at 60° C., and 31 cycles up to (ii).

(ii) Recombination of *Pseudomonas* Sp. H-8-1-3-Derived L-Amino Acid Oxidase Gene into pET15b Vector and Transformation of *E. coli* (*E. coli* BL21)

To 5 µL of the PCR product obtained in the PCR reaction were added 1 µL of NdeI and 1 µL of XhoI and the mixture was incubated for 1 hour at 37° C. to conduct restriction enzyme treatment. The ligation reaction was conducted with 5 µL of DNA, 1 µL of pET15B (which had been subjected to the same restriction enzyme treatment as the amplified gene), and 6 µL of ligation mix, which were incubated for 30 minutes at 16° C. The entire quantity of the ligation reaction solution obtained was introduced into *E. coli* (*E. coli* BL21) by the heat shock method. An expression plasmid was constructed so that the L-amino acid oxidase produced by the recombinant *E. coli* would be produced as a fused protein to which 6× histidine tags were added to the N-terminal side.

(iii) Expression of *Pseudomonas* Sp. H-8-1-3-Derived L-Amino Acid Oxidase Gene and Purification of Fused Enzyme with 6 Histidine Tags Using Ni-Sepharose The recombinant *E. coli* (BL21) was inoculated onto 4 liters of LB medium (1.0% of polypeptone, 0.5% of yeast extract, 1.0% of NaCl, pH 7.0) containing 80 µg/mL of ampicillin and cultured for 12 hours at 37° C. Subsequently, 0.5 mM IPTG was added. The mixture was then cultured for 12 hours at 30° C. and L-amino acid oxidase was induced. The cells were collected using a large centrifuge (5,000 rpm, 10 minutes, 4° C.), washed with physiological saline (0.9% NaCl), and suspended in 100 mL of 20 mM phosphate buffer (pH 7.0) (KPB). A 100 mL quantity of the bacterial cell solution was ultrasonically treated for 15 minutes and centrifuged (8,000 rpm, 20 minutes, 4° C.). The supernatant obtained was adopted as a cell-free extract. The cell-free extract was adsorbed on a Ni-Sepharose column substituted with 20 mM KPB and the column was washed with 20 mM of KPB and then, with 20 mM of KPB containing 500 mM imidazole, causing the enzyme solution to elute.

(9) Measurement of the Activity of *Pseudomonas* Sp. H-8-1-3-Derived L-Amino Acid Oxidase The enzymatic activity of the purified enzyme preparation was measured with measurement reagents containing the single amino acids indicated in Table 3. The enzyme preparation was found to have the following properties:

(a) It employed L-lysine, L-arginine, and L-ornithine as a substrate (Table 5). The L-amino acid oxidase did not exhibit activity for other amino acids constituting proteins (L-tyrosine, L-alanine, L-cysteine, L-aspartic acid, L-glutamic acid, glycine, L-histidine, L-isoleucine, L-leucine, L-methionine, L-asparagine, L-proline, L-glutamine, L-serine, L-threonine, L-valine, L-phenylalanine, and L-tryptophan).

TABLE 5

| | Enzyme activity (munit/mL) | |
|---|---|---|
| L-lysine | 0.532 | 100 |
| L-ornithine | 0.146 | 27 |
| L-arginine | 0.108 | 20 |

Figure 5:
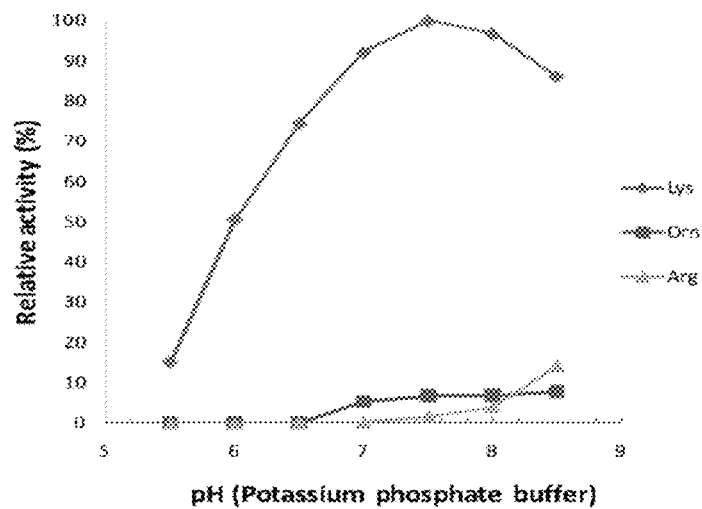
FIG. 5 shows the enzymatic activity (pH dependence) of the wild-type enzyme purified in the Examples relative to L-lysine (Lys), L-ornithine (Orn), and L-arginine (Arg).

(b) At pH 6.5 and below, it only acted on L-lysine (FIG. 5).

(10) Quantification of L-Lysine with *Pseudomonas* Sp. H-8-1-3-Derived L-Amino Acid Oxidase The above L-lysine-detecting reagent composition was prepared using the L-amino acid oxidase preparation purified in (8) (iii) above in which histidine tags had been added to the N-terminal side. L-lysine was measured using this reagent composition. Specimens in the form of 1 to 6 mM L-lysine aqueous solutions were prepared.

Figure 6:
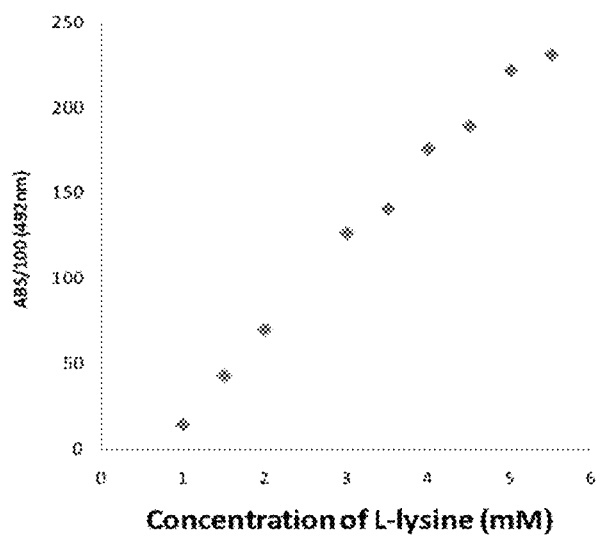
FIG. 6 shows the correlation between the L-lysine concentration and the absorbance at 492 nm when 1 to 6 mM L-lysine aqueous solutions were employed as specimens using the wild-type enzyme preparation purified in the Examples.

The results revealed that when L-lysine aqueous solutions were employed as specimens, reactivity was observed. The L-lysine concentration and measurement data indicated a good, positive correlation (see FIG. 6).

(11) the Introduction of Mutations into the *Pseudomonas* Sp. H-8-1-3-Derived L-Amino Acid Oxidase Gene Variant L-amino acid oxidase having oxidase activity highly substrate specific to L-lysine was fabricated by conducting saturation mutation of the cysteine at position 254 in the amino acid sequence of the above L-amino acid oxidase.

The expression plasmids into which the L-amino acid oxidase genes had been incorporated, constructed in (8) (ii) above, were employed as templates in mutagenic PCR. In the PCR reaction, a QuikChange® Multi Site-Directed Mugagenesis Kit (Stratagene) was employed. The composition of the PCR reaction solution was 16.5 µL of sterile water (MilliQ), 2.5 µL of 10×QuikChange Lightening Multireaction buffer, 1.0 µL of 100 ng/µL template DNA, 1.0 µL of 100 ng/µL primer 7 (5'-GTGGTGAT-GACCAATNNSGAC-GACCACCAACAC-3') (SEQ. ID NO: 23), 1.0 µL of 100 ng/µL primer 8 (5'-GCGGTGCTGACGACCNNSCAGAGT-TGGCTGCTG-3') (SEQ. ID NO: 24), 1.0 µL of 100 ng/µL primer 9 (5'-AAGCCAGGGGTGATCNNSCTGTC-CTACGCGTGG-3') (SEQ. ID NO: 25), 1.0 µL of dNTP mix, and 1.0 µL of QuikChange Lightning Multi enzyme blend. The PCR reaction conditions were (i) 2 minutes at 95° C., (ii) 20 seconds at 95° C., (iii) 30 seconds at 55° C., (iv) 4 minutes at 65° C., and (v) (ii) to (iv) for 5 minutes at 65° C. To the PCR product was added 1.0 µL of DpnI and the mixture was left standing for 5 minutes at 37° C. (sample 1). Similarly, 1.0 µL of 100 ng/µL primer 10 (5'-CATGTGCCAGAGCGTNNS-GCGCACTGGCCCGAA-3') (SEQ. ID NO: 26) and 1.0 µL of 100 ng/µL primer 11 (5'-ACCACCCAGATCGACNNS-GAAGAGTCGTTGTTC-3') (SEQ. ID NO: 27) were employed to conduct the above processing (sample 2).

*Escherichia coli* JM109 was transformed using each of samples 1 and 2 and cultured for 12 hours at 37° C. in 5 mL of LB liquid medium to which 500 µg of ampicillin had been added. Once the culturing had ended, the various samples were centrifuged (13,000 rpm, 4° C., 5 minutes) to collect the bacteria. The collected bacterial mass was subjected to plasmid extraction by the alkali mini prep method. The alkali mini prep method was conducted according to the following procedure. (1) *E. coli* culture solution containing plasmid DNA was moved to a 1.5 mL tube and centrifuged. The bacterial mass was recovered as pellets. (2) A 100 µL quantity of solution I (25 mM Tris-HCl (pH 8.0), 10 mM EDTA, 0.9% glucose) was added to the bacterial pellets to prepare a suspension. (3) A 200 µL quantity of solution II (0.2 M NaOH, 1% SDS) was added, the bacterial mass was dissolved, and the protein and nucleic acid were denatured. (4) A 150 µL quantity of solution III (3 M potassium acetate and 11.5% acetic acid) was added, the solution was neutralized, and the SDS was removed. These operations rendered the chromosomal DNA and protein in the form of an aggregated precipitate. However, the plasmid DNA remained in the dissolved portion. (5) The aggregated precipitate was removed from the solution by centrifugation, and the solution containing the plasmid DNA was recovered. (6) The solution containing the plasmid DNA that was obtained was subjected to phenol chloroform extraction to remove the protein. (7) A quantity of ethanol double that of the plasmid solution was added and the mixture was placed for 5 minutes on dry ice. (8) The plasmid DNA was precipitated by a centrifugal operation. (9) The precipitate of plasmid DNA obtained was dissolved in TE (10 mM Tris-HCl, pH 8.0, 1 mM EDTA) to obtain a sample.

The product obtained by PCR1 was denoted as plasmid1 and the product obtained by PCR2 was denoted as plasmid2 among the plasmids obtained. These were used to transform E. coli BL21(DE3) by the heat shock method. The procedure of the heat shock method was as follows. To a 50 μL quantity of E. coli BL21(DE3) was added 5 μL quantity of each of the plasmids and the mixtures were left standing on ice for 60 minutes. Subsequently, heat shock was conducted for 90 seconds at 42 degrees, after which 1 mL of LB liquid medium was added and the bacteria were incubated for 1 hour at 37 degrees. The culture was spread on plates containing ampicillin and cultured for 16 hours at 37 degrees.

To each well of a 96-deep-well plate was dispensed a 300 μL quantity of LB liquid medium containing 100 μL/mL of ampicillin. A colony picker was then employed to inoculate the colonies obtained into the medium of each well. Following inoculation, a shaker was used to conduct culturing for 12 hours at 37 degrees and 700 rpm. Subsequently 20 μL of 7.5 mM IPTG was added and shake culturing was again conducted for 12 hours at 30 degrees. Following culturing, centrifugation (2,500 rpm, 4° C., 20 minutes) was used to collect the bacteria. To each mass of collected bacteria was added 200 μL of 10 mM KPB (pH 7.0) to form a suspension. The bacteria were transferred to a 96-well round-bottomed plate and the bacterial mass was crushed in an eight-section sonicator (output 3, 30 seconds). Following centrifugation under identical conditions, the supernatant obtained was collected as a cell-free extract. A 50 μL quantity of this cell-free extract was employed to measure relative activity with L-lysine as substrate by the above active measurement method.

The transformants were screened for those exhibiting marked activity. As a result, 175 colonies were obtained from the 4,000 colonies obtained in PCR1 and 50 colonies were obtained from the 500 colonies obtained in PCR2.

The supernatant of the colonies obtained was used to again measure the activity with p-chloromercuribenzoate (PCMB). The SH group in the protein reacted with the metal ion, forming a mercaptide. Although this reaction was reversible, equilibrium is generally highly skewed by mercaptides. Hg2+ is highly hydrophilic with respect to SH groups. For enzymes having oxidase activity or monooxygenase activity, it is widely known among persons having ordinary skill in the art that the addition of PCMB reagent skews oxidase activity.

Based on the above, screening was conducted to find enzymes exhibiting no difference in activity when PCMB was added to the cell-free extract and when it was not. As a result, four colonies were obtained among the 175 colonies from PCR1 and four colonies were obtained among the 50 colonies from PCR2. A Big Dye Terminator v3.1 Cycle Sequencing Kit (made by Applied Biosystems) and a DNA Sequencer 310 Genetic Analyzer (also made by Applied Biosystems) were used to sequence the plasmids contained in the colonies obtained. As a result, it was found that the TGC base sequence of numbers 760 to 762 in the coding region had mutated to ATC, and that this mutation had replaced the cysteine at position 254 in the amino acid sequence with isoleucine. This variant enzyme was named variant enzyme C254I.

The variant enzymes obtained as the results of this screening were purified by the method described in (8) (iii) above. As shown in FIG. 1, in the wild-type enzyme, the monooxygenase reaction accounts for a far greater portion than the oxidase reaction. However, in purified variant enzyme C254I, PCMB produced no visible effect, and no products of monooxygenase were detected by HPLC.

To examine the effect of pH on variant enzyme C254I during the reaction, the pH of the reagent composition was varied and the oxidase activity at various pH levels was measured for substrates in the form of L-lysine, L-ornithine, and L-arginine. FIG. 7 shows the effects of pH on the wild-type enzyme and the variant enzymes.

As shown in FIG. 7A, at pH 7.0, since wild-type enzyme catalyzed not only L-lysine, but also L-arginine and L-ornithine, there was a limitation in that it was necessary to conduct the reaction at pH 6.5 or lower to accurately quantify L-lysine with the wild-type enzyme. By contrast, as shown in FIG. 7B, variant enzyme C254I exhibited high substrate specificity for L-lysine even in the vicinity of pH 7.0. Thus, it was possible to specifically detect L-lysine irrespective of the pH of the reaction system. As shown in FIG. 7A-B, the relative activity of the wild-type enzyme at pH 6.5 was 0.56 U/mg. By contrast, the relative activity of variant enzyme C254I at pH 7.5 was 2.5 U/mg. Variant enzyme C254I exhibited higher oxidase activity than the wild-type enzyme.

The oxidase activity of variant enzyme C254I was measured for substrates in the form of amino acids other than L-lysine, L-arginine, and L-ornithine. The activity measuring reagents and activity measuring method were as indicated in (1) and (2) above. The reaction conditions were pH 7.0 and 30° C. The results are given in FIG. 8B. FIG. 8A shows the results for the wild-type enzyme.

As shown in FIG. 8A-B, variant enzyme C254I did not exhibit activity for L-arginine or L-ornithine as well as it did not exhibit activity for any other amino acids. It only exhibited oxidase activity for L-lysine. The variant enzyme of the present invention exhibited oxidase activity of high substrate specificity for L-lysine, showing that it could specifically detect L-lysine.

Further, the above L-lysine measuring reagent composition was prepared using the purified wild-type enzyme prepared in (8) (iii) above and variant enzyme C254I. L-lysine was measured with this reagent composition. As specimens, 1 to 10 mM L-lysine aqueous solutions were prepared.

Figure 9:
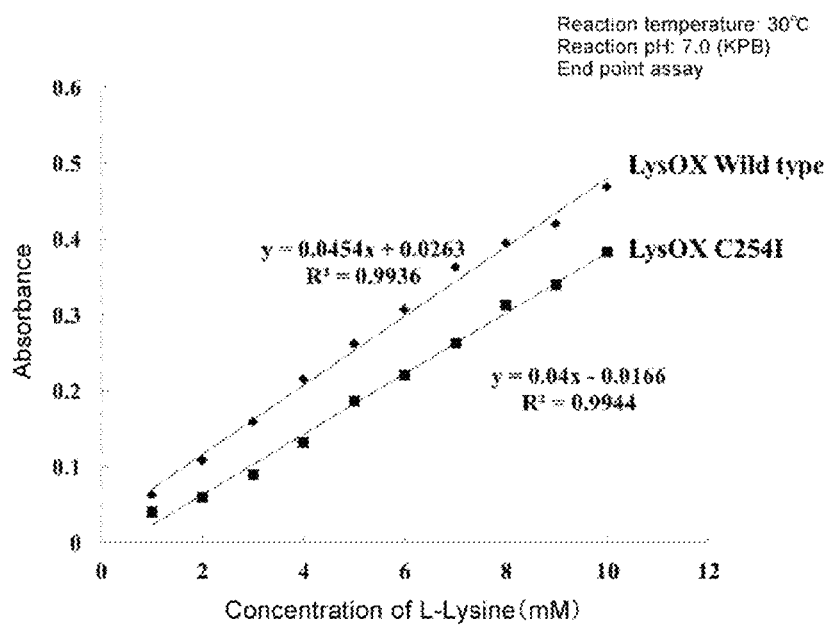
FIG. 9 shows the relation between L-lysine concentration and absorbance when 1-10 mM L-lysine aqueous solutions were employed as specimens using wild-type enzyme and the variant enzyme C254I of the present invention.

As a result, reactivity was observed when L-lysine aqueous solutions were employed as specimens. The L-lysine concentration and measurement data exhibited a good, positive correlation (see FIG. 9).

Further, in the variant obtained by the above saturation mutation, even when the cysteine at position 254 had been replaced with an amino acid other than isoleucine, oxidase activity was measured for L-lysine, L-arginine, and L-ornithine. The activity measuring reagents and activity measurement method were identical to those indicated in (1) and (2) above. Reaction conditions of pH 7.0 and 30° C. were employed. The results are given in Tables 6 and 7 and FIGS. 10 and 11.

TABLE 6

Enzymatic activity of individual variants (U/mg)

| | | Substrate | | |
|---|---|---|---|---|
| | | L-lysine | L-arginine | L-ornithine |
| Amino acid | Cys | 0.580 | 0.121 | 0.481 |
| substituted in | Met | 1.80 | 0.000 | 0.080 |
| saturation | Phe | 1.84 | 0.180 | 0.000 |
| mutation of | Tyr | 1.93 | 0.000 | 0.000 |
| C254 | Trp | 1.33 | 0.332 | 0.151 |
| | Ala | 0.350 | 0.031 | 0.190 |
| | Gly | 0.360 | 0.251 | 0.184 |
| | Val | 1.24 | 0.113 | 0.121 |
| | Ile | 2.80 | 0.010 | 0.000 |

TABLE 6-continued

Enzymatic activity of individual variants (U/mg)

| | | Substrate | | |
|---|---|---|---|---|
| | | L-lysine | L-arginine | L-ornithine |
| | Leu | 2.21 | 0.111 | 0.092 |
| | Lys | 1.00 | 0.260 | 0.000 |
| | Arg | 0.890 | 0.563 | 0.000 |
| | His | 0.410 | 0.210 | 0.110 |
| | Asp | 1.77 | 0.000 | 0.461 |
| | Glu | 1.60 | 0.000 | 0.240 |
| | Ser | 0.530 | 0.020 | 0.114 |
| | Thr | 0.300 | 0.051 | 0.250 |
| | Asn | 1.20 | 0.620 | 0.141 |
| | Gln | 1.10 | 0.282 | 0.111 |
| | Pro | 1.15 | 0.430 | 0.811 |

TABLE 7

Enzymatic activity of individual variants (relative activity %)

| | | Substrate | | |
|---|---|---|---|---|
| | | L-lysine | L-arginine | L-ornithine |
| Amino acid substituted in saturation mutation of C254 | Cys | 100 | 20.9 | 82.9 |
| | Met | 100 | 0.000 | 4.44 |
| | Phe | 100 | 9.78 | 0.000 |
| | Tyr | 100 | 0.000 | 0.000 |
| | Trp | 100 | 25.0 | 11.4 |
| | Ala | 100 | 8.86 | 54.3 |
| | Gly | 100 | 69.7 | 51.1 |
| | Val | 100 | 9.11 | 9.76 |
| | Ile | 100 | 0.357 | 0.000 |
| | Leu | 100 | 5.02 | 4.16 |
| | Lys | 100 | 26.0 | 0.000 |
| | Arg | 100 | 63.3 | 0.000 |
| | His | 100 | 51.2 | 26.8 |
| | Asp | 100 | 0.000 | 26.0 |
| | Glu | 100 | 0.000 | 15.0 |
| | Ser | 100 | 3.77 | 21.5 |
| | Thr | 100 | 17.0 | 83.3 |
| | Asn | 100 | 51.7 | 11.8 |
| | Gln | 100 | 25.6 | 10.1 |
| | Pro | 100 | 37.4 | 70.5 |

Figure 10:
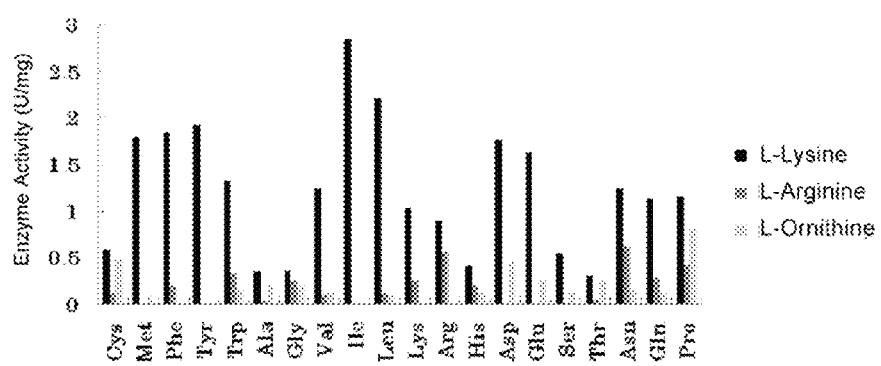
FIG. 10 shows the results of examining the substrate specificity of various variant enzymes obtained by mutating the cysteine at position 254 to various amino acids in the amino acid sequence of the wild-type enzyme.
Figure 11:
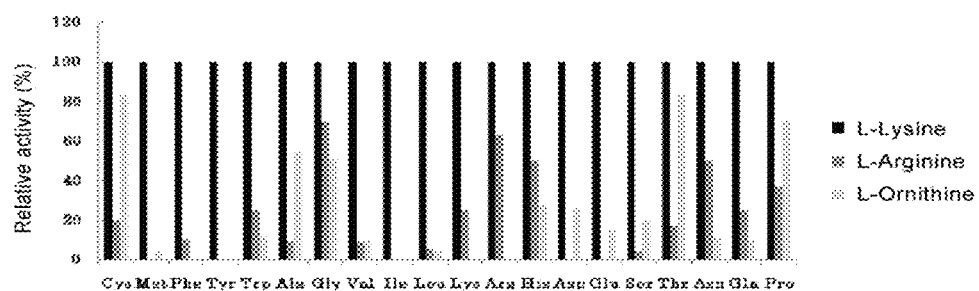
FIG. 11 shows the relative activity of L-arginine and L-ornithine to the oxidase activity on L-lysine as 100% for the results of FIG. 10.

As shown in Table 6 and FIG. 10, in addition to variant enzyme C254I, variant enzymes substituted with methionine (Met), phenylalanine (Phe), tyrosine (Tyr), tryptophan (Trp), valine (Val), leusine (Leu), lysine (Lys), arginine (Arg), aspartic acid (Asp), glutamic acid (Glu), asparagine (Asn), glutamine (Gln), and proline (Pro) were found to tend to exhibit greater oxidase activity on L-lysine than the wild-type enzyme. Further, as shown in Table 7 and FIG. 11, the fact that the variant enzymes substituted with methionine (Met), phenylalanine (Phe), tyrosine (Tyr), tryptophan (Trp), alanine (Ala), glycine (Gly), valine (Val), leusine (Leu), lysine (Lys), arginine (Arg), histidine (His), aspartic acid (Asp), glutamic acid (Glu), serine (Ser), threonine (Thr), asparagine (Asn), glutamine (Gln), and proline (Pro) were found to exhibit lower relative activity on L-ornithine and L-arginine than the wild-type enzyme when the oxidase activity on L-lysine was defined as 100% showed that these variant enzymes exhibited oxidase activity with high substrate specificity for L-lysine. Additionally, among these amino acid substitutions, in variant enzymes substituted with methionine (Met), phenylalanine (Phe), tyrosine (Tyr), alanine (Ala), valine (Val), isoleucine (Ile), leucine (Leu), asparagine (Asp), glutamic acid (Glu), or serine (Ser), the relative activity both in terms of L-arginine oxidase activity and L-ornithine oxidase activity was lower than in the wild-type enzyme. Thus, these variant enzymes had particularly high substrate specificity for L-lysine (see Table 7 and FIG. 11). Further, in the variant enzymes substituted with tyrosine and isoleucine, no oxidase activity on L-ornithine and L-arginine was detected. These enzymes were found to have extremely high substrate specificity for L-lysine (Tables 6 and 7 and FIGS. 10 and 11).

L-amino acid oxidase activity was measured for substrates in the form of the constituent amino acids of proteins in the form of L-tyrosine, L-alanine, L-cysteine, L-aspartic acid, L-glutamic acid, glycine, L-histidine, L-isoleucine, L-leucine, L-methionine, L-asparagine, L-proline, L-glutamine, L-serine, L-threonine, L-valine, L-phenylalanine, and L-tryptophan when the cysteine at position 254 was substituted with an amino acid other than isoleucine in the variants obtained by the above saturation mutation. As a result, no L-amino acid oxidase activity was detected in any of the variant enzymes when these amino acids were employed as substrates. Additionally, no L-amino acid oxidase activity was detected in any of the variant enzymes even when D-lysine, D-arginine, and D-ornithine were employed as substrates.

(12) Measurement of Blood Plasma Samples

Human blood plasma samples to which L-lysine, L-ornithine, or L-arginine had been added were used to measure oxidase activity in the above variant enzyme C254I. Amicon Ultra 0.5 (UFC501096, Millipore) was used as the human serum and a deproteinized solution was prepared by centrifugation for 30 minutes at 16,100×g and 4° C. To the prepared human plasma were added L-lysine, L-ornithine, or L-arginine to final concentrations of 0, 5, 10, 15, 20, 25, 30, 35, 40, and 45 μM to prepare plasma samples. The measurement reagent composition and measurement method were the same as those indicated in (1) and (2) above. The reaction conditions were pH 7.0 and 30° C. The results are given in FIG. 14. The same human plasma samples were employed and the oxidase activity was measured for the wild-type enzyme by way of comparison. The results are given in FIG. 12.

Figure 12:
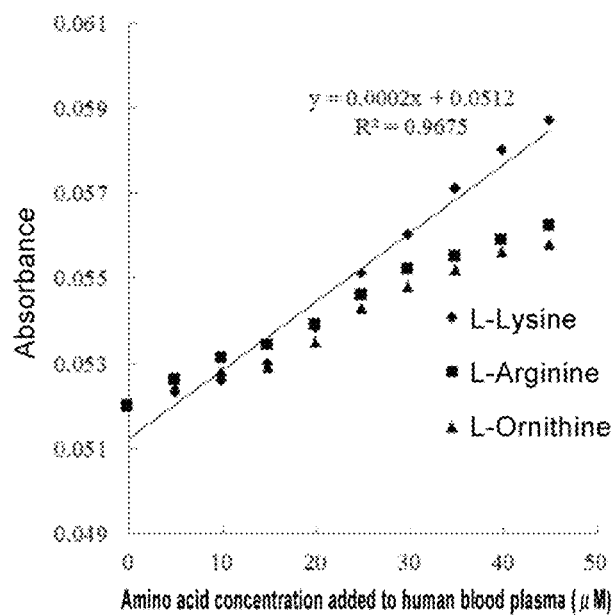
FIG. 12 shows the results of quantifying various amino acids using wild-type enzyme for blood plasma samples to which L-lysine, L-arginine, and L-ornithine have been added.
Figure 13:
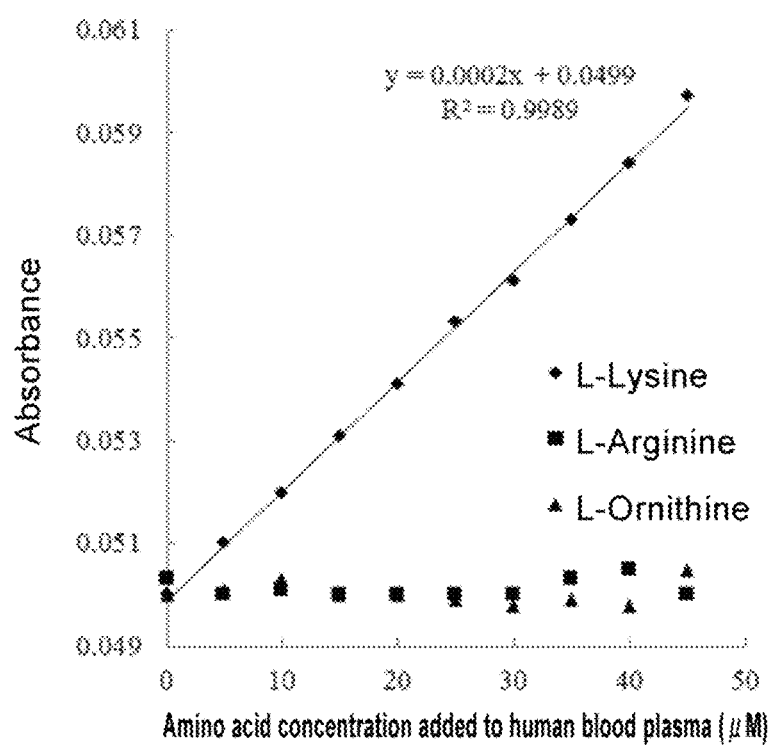
FIG. 13 shows the results of quantifying various amino acids using the variant enzyme C254I of the present invention for blood plasma samples to which L-lysine, L-arginine, and L-ornithine have been added.

As shown in FIG. 12, although the wild-type enzyme permitted quantification of lysine, oxidase activity was detected for ornithine and arginine, as well. By contrast, as shown in FIG. 13, oxidase activity was only detected for L-lysine in the case of the variant enzyme C254I, making it possible to plot a straight calibration curve.

Based on the above test examples, the use of the variant enzyme of the present invention permitted the accurate detection or quantification of L-lysine even in clinical samples containing amino acids other than L-lysine.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

The invention claimed is:

1. An isolated lysine oxidase selected from the group consisting of:
   (1) a lysine oxidase consisting of the amino acid sequence of SEQ ID NO: 2, but wherein the cysteine at position 254 has been replaced with a replacement amino acid selected from the group consisting of methionine, phenylalanine, tyrosine, tryptophan, alanine, glycine, valine, isoleucine, leucine, lysine, arginine, histidine, aspartic acid, glutamic acid, serine, threonine, asparagine, glutamine, and proline; and
   (2) a lysine oxidase comprising an amino acid sequence having at least 90% sequence identity with the amino acid sequence of SEQ ID NO: 2, wherein the amino acid at position 254 is replaced with a replacement amino acid selected from the group consisting of methionine, phenylalanine, tyrosine, tryptophan, alanine, glycine, valine, isoleucine, leucine, lysine, arginine, histidine, aspartic acid, glutamic acid, serine, threonine, asparagine, glutamine, and proline;
   wherein said lysine oxidase has oxidase activity with higher substrate specificity for L-lysine than a lysine oxidase consisting of the amino acid sequence of SEQ ID NO: 2.

2. The lysine oxidase according to claim 1, wherein the replacement amino acid is selected from the group consisting of methionine, phenylalanine, tyrosine, alanine, valine, isoleucine, leucine, aspartic acid, glutamic acid, and serine.

3. The lysine oxidase according to claim 1, wherein the replacement amino acid is isoleucine or tyrosine.

4. The lysine oxidase according to claim 1, wherein the replacement amino acid is selected from the group consisting of methionine, phenylalanine, tyrosine, alanine, valine, isoleucine, leucine, aspartic acid, glutamic acid, and serine and the oxidase activity of the lysine oxidase on L-arginine is 15% or less than the oxidase activity on L-lysine, and the oxidase activity of the lysine oxidase on L-ornithine is 80% or less than the oxidase activity on L-lysine.

5. An isolated nucleic acid coding for the lysine oxidase according to claim 1.

6. A vector comprising the nucleic acid according to claim 5.

7. A transformant that has been transformed by the vector according to claim 6.

8. A method for detecting or quantifying L-lysine, comprising:
   (A) maintaining a specimen and the lysine oxidase according to claim 1 in the presence of water and oxygen; and
   (B) detecting or quantifying at least one reaction product produced in the reaction solution by the effect of the oxidase activity of the lysine oxidase on L-lysine.

9. The method according to claim 8, wherein the reaction product that is detected or quantified in step (B) is hydrogen peroxide and the hydrogen peroxide is detected or quantified using peroxidase.

10. The method according to claim 8, wherein the reaction product that is detected or quantified in step (B) is ammonia and the ammonia is detected or quantified using an ammonia-detecting reagent.

11. The method according to claim 8, wherein the reaction product that is detected or quantified in step (B) is a deamination product of L-lysine.

12. A kit for detecting or quantifying L-lysine, comprising the lysine oxidase according to claim 1.

13. The kit according to claim 12, further comprising a kit component selected from the group consisting of a reaction buffer, a hydrogen peroxide-detecting reagent, an ammonia-detecting reagent, and an L-lysine deamination product-detecting agent.

14. A L-lysine-detecting or quantifying enzyme sensor comprising an electrode for detecting hydrogen peroxide, wherein the lysine oxidase according to claim 1 is disposed on the surface or in the vicinity of the electrode for detecting hydrogen peroxide.

15. The sensor according to claim 14, wherein the electrode for detecting hydrogen peroxide is an enzymatic hydrogen peroxide electrode or a diaphragm hydrogen peroxide electrode.

* * * * *

SEQUENCE LISTING

<160> NUMBER OF SEQ ID NOS: 27

<210> SEQ ID NO 1
<211> LENGTH: 1683
<212> TYPE: DNA
<213> ORGANISM: Pseudomonas sp.
<220> FEATURE:
<221> NAME/KEY: CDS
<222> LOCATION: (1)..(1680)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | aac | aag | aac | aac | cgc | cac | ccg | gcc | gac | ggt | aaa | aaa | ccg | atc | acc | 48 |
| Met | Asn | Lys | Asn | Asn | Arg | His | Pro | Ala | Asp | Gly | Lys | Lys | Pro | Ile | Thr | |
| 1 | | | | 5 | | | | | 10 | | | | | 15 | | |
| atc | ttc | ggc | ccg | gac | ttc | cct | ttt | gcc | ttc | gat | gat | tgg | ctg | gaa | cac | 96 |
| Ile | Phe | Gly | Pro | Asp | Phe | Pro | Phe | Ala | Phe | Asp | Asp | Trp | Leu | Glu | His | |
| | | | 20 | | | | | 25 | | | | | 30 | | | |
| ccg | gct | ggc | ctg | ggt | agc | atc | cca | gcc | gcg | cgt | cat | ggt | gaa | gaa | gtg | 144 |
| Pro | Ala | Gly | Leu | Gly | Ser | Ile | Pro | Ala | Ala | Arg | His | Gly | Glu | Glu | Val | |
| | | 35 | | | | | 40 | | | | | 45 | | | | |
| gcg | atc | gtg | ggc | gcc | ggc | atc | gcc | ggg | ctg | gtg | gcg | gcc | tac | gag | ctg | 192 |
| Ala | Ile | Val | Gly | Ala | Gly | Ile | Ala | Gly | Leu | Val | Ala | Ala | Tyr | Glu | Leu | |
| | 50 | | | | | 55 | | | | | 60 | | | | | |
| atg | aag | ctg | ggc | ctc | aaa | ccg | gtg | gtc | tac | gag | gcg | tcg | aag | atg | ggt | 240 |
| Met | Lys | Leu | Gly | Leu | Lys | Pro | Val | Val | Tyr | Glu | Ala | Ser | Lys | Met | Gly | |
| 65 | | | | | 70 | | | | | 75 | | | | | 80 | |
| ggg | cgg | ctg | cgc | tcg | cag | gcc | ttc | aac | ggc | acc | gac | ggt | atc | atc | gcc | 288 |
| Gly | Arg | Leu | Arg | Ser | Gln | Ala | Phe | Asn | Gly | Thr | Asp | Gly | Ile | Ile | Ala | |
| | | | | 85 | | | | | 90 | | | | | 95 | | |
| gag | ctg | ggc | gga | atg | cgc | ttt | ccg | gtg | tcg | tcc | acg | gcg | ttc | tac | cac | 336 |
| Glu | Leu | Gly | Gly | Met | Arg | Phe | Pro | Val | Ser | Ser | Thr | Ala | Phe | Tyr | His | |
| | | | 100 | | | | | 105 | | | | | 110 | | | |
| tac | gtc | gac | aag | ctg | ggc | ctg | gaa | acc | aag | cct | ttc | ccc | aac | ccg | ctc | 384 |
| Tyr | Val | Asp | Lys | Leu | Gly | Leu | Glu | Thr | Lys | Pro | Phe | Pro | Asn | Pro | Leu | |
| | | 115 | | | | | 120 | | | | | 125 | | | | |
| acc | cct | gcc | tca | cgc | agc | acg | gta | atc | gat | ctg | gaa | ggc | cag | acc | tac | 432 |
| Thr | Pro | Ala | Ser | Arg | Ser | Thr | Val | Ile | Asp | Leu | Glu | Gly | Gln | Thr | Tyr | |
| | 130 | | | | | 135 | | | | | 140 | | | | | |
| tac | gcg | gaa | aaa | gcc | gcc | gac | ttg | ccg | gcc | ctg | ttc | cag | gaa | gtt | acc | 480 |
| Tyr | Ala | Glu | Lys | Ala | Ala | Asp | Leu | Pro | Ala | Leu | Phe | Gln | Glu | Val | Thr | |
| 145 | | | | | 150 | | | | | 155 | | | | | 160 | |
| gat | gcc | tgg | gcc | gac | gcc | ctg | gaa | agc | ggt | gcg | cgc | ttt | ggt | gac | atc | 528 |
| Asp | Ala | Trp | Ala | Asp | Ala | Leu | Glu | Ser | Gly | Ala | Arg | Phe | Gly | Asp | Ile | |
| | | | | 165 | | | | | 170 | | | | | 175 | | |
| cag | caa | gca | att | cgt | gac | cgt | gac | gtg | cct | cgc | ttg | aaa | gaa | ctg | tgg | 576 |
| Gln | Gln | Ala | Ile | Arg | Asp | Arg | Asp | Val | Pro | Arg | Leu | Lys | Glu | Leu | Trp | |
| | | | 180 | | | | | 185 | | | | | 190 | | | |
| aac | acc | ctg | gtg | ccg | ctg | tgg | gac | gac | cgc | act | ttc | tac | gac | ttc | gtc | 624 |
| Asn | Thr | Leu | Val | Pro | Leu | Trp | Asp | Asp | Arg | Thr | Phe | Tyr | Asp | Phe | Val | |
| | | 195 | | | | | 200 | | | | | 205 | | | | |
| gcc | acc | tcc | aaa | gcc | ttc | gcc | aaa | ctg | agt | ttc | cag | cac | cgc | gaa | gtg | 672 |
| Ala | Thr | Ser | Lys | Ala | Phe | Ala | Lys | Leu | Ser | Phe | Gln | His | Arg | Glu | Val | |
| | 210 | | | | | 215 | | | | | 220 | | | | | |
| ttc | ggc | cag | gtg | ggc | ttc | ggc | acc | ggt | ggt | tgg | gat | tcg | gac | ttc | ccc | 720 |
| Phe | Gly | Gln | Val | Gly | Phe | Gly | Thr | Gly | Gly | Trp | Asp | Ser | Asp | Phe | Pro | |
| 225 | | | | | 230 | | | | | 235 | | | | | 240 | |
| aac | tcg | atg | ctg | gaa | atc | ttc | cgt | gtg | gtg | atg | acc | aat | tgc | gac | gac | 768 |
| Asn | Ser | Met | Leu | Glu | Ile | Phe | Arg | Val | Val | Met | Thr | Asn | Cys | Asp | Asp | |
| | | | | 245 | | | | | 250 | | | | | 255 | | |

```
cac caa cac ctg gtg gtc ggc ggc gtc gag caa gtg ccg cag ggc atc        816
His Gln His Leu Val Val Gly Gly Val Glu Gln Val Pro Gln Gly Ile
            260                 265                 270 tgg cgc cat gtg cca gag cgt tgt gcg cac tgg ccc gaa ggt acc agc        864
Trp Arg His Val Pro Glu Arg Cys Ala His Trp Pro Glu Gly Thr Ser
        275                 280                 285 ctg agc tcg ctg cac ggc ggt gca ccg cgc acc ggc gtc aag cgc att        912
Leu Ser Ser Leu His Gly Gly Ala Pro Arg Thr Gly Val Lys Arg Ile
    290                 295                 300 gcc cgc gcc agc gac ggc cgc ctg gca gtc acc gac aac tgg ggc gac        960
Ala Arg Ala Ser Asp Gly Arg Leu Ala Val Thr Asp Asn Trp Gly Asp
305                 310                 315                 320 tgc cgc cat tac gcg gcg gtg ctg acg acc tgc cag agt tgg ctg ctg       1008
Cys Arg His Tyr Ala Ala Val Leu Thr Thr Cys Gln Ser Trp Leu Leu
            325                 330                 335 acc acc cag atc gac tgt gaa gag tcg ttg ttc tcg cag aag atg tgg       1056
Thr Thr Gln Ile Asp Cys Glu Glu Ser Leu Phe Ser Gln Lys Met Trp
        340                 345                 350 atg gcc ctg gac cgc acc cgc tac atg caa tcg tcg aaa acc ttc gtc       1104
Met Ala Leu Asp Arg Thr Arg Tyr Met Gln Ser Ser Lys Thr Phe Val
    355                 360                 365 atg gtc gac cgg ccg ttc tgg aaa gac aaa gac cca gaa acc ggt cgc       1152
Met Val Asp Arg Pro Phe Trp Lys Asp Lys Asp Pro Glu Thr Gly Arg
370                 375                 380 gac ctg atg agc atg acc ctc acc gac cgg ctg acc cgt ggc acc tac       1200
Asp Leu Met Ser Met Thr Leu Thr Asp Arg Leu Thr Arg Gly Thr Tyr
385                 390                 395                 400 ctg ttc gat aac ggc gac gac aag cca ggg gtg atc tgc ctg tcc tac       1248
Leu Phe Asp Asn Gly Asp Asp Lys Pro Gly Val Ile Cys Leu Ser Tyr
            405                 410                 415 gcg tgg atg agc gat gcc ctg aag atg ctc ccg cac ccg gtg gaa aaa       1296
Ala Trp Met Ser Asp Ala Leu Lys Met Leu Pro His Pro Val Glu Lys
        420                 425                 430 cgc gtg caa ctg gca ctc gat gca ttg aaa aag atc tac ccg aaa acc       1344
Arg Val Gln Leu Ala Leu Asp Ala Leu Lys Lys Ile Tyr Pro Lys Thr
    435                 440                 445 gat atc gcc ggg cat atc atc ggc gac cct att acc att tcc tgg gaa       1392
Asp Ile Ala Gly His Ile Ile Gly Asp Pro Ile Thr Ile Ser Trp Glu
450                 455                 460 gcc gac ccg cac ttc ctc ggt gca tcc aaa ggc gcg ctg ccg ggc cac       1440
Ala Asp Pro His Phe Leu Gly Ala Ser Lys Gly Ala Leu Pro Gly His
465                 470                 475                 480 tat cgc tac aac cag cgg atg tac gcg cac ttc atg cag gcg cag atg       1488
Tyr Arg Tyr Asn Gln Arg Met Tyr Ala His Phe Met Gln Ala Gln Met
            485                 490                 495 cca gtc gag cag cgt ggc att ttc att gcc ggc gac gac gtg tcg tgg       1536
Pro Val Glu Gln Arg Gly Ile Phe Ile Ala Gly Asp Asp Val Ser Trp
        500                 505                 510 acc ccg gcc tgg gtg gaa ggc gcg gtg cag acc tcg ctc aat gcc gtg       1584
Thr Pro Ala Trp Val Glu Gly Ala Val Gln Thr Ser Leu Asn Ala Val
    515                 520                 525 tgg ggt atc atg aat cac ttt ggt ggc aag acc cac gcg gac aac ccc       1632
Trp Gly Ile Met Asn His Phe Gly Gly Lys Thr His Ala Asp Asn Pro
530                 535                 540 ggc cct ggc gac gtg ttc gat gag atc ggc caa atc gcc ctg gcg gac       1680
Gly Pro Gly Asp Val Phe Asp Glu Ile Gly Gln Ile Ala Leu Ala Asp
545                 550                 555                 560 tga                                                                    1683
```

-continued

```
<210> SEQ ID NO 2
<211> LENGTH: 560
<212> TYPE: PRT
<213> ORGANISM: Pseudomonas sp.

<400> SEQUENCE: 2
```

| | | | | | | | | | | | | | | |
|---|---|---|---|---|---|---|---|---|---|---|---|---|---|---|
| Met | Asn | Lys | Asn | Asn | Arg | His | Pro | Ala | Asp | Gly | Lys | Lys | Pro | Ile | Thr |
| 1 | | | | 5 | | | | | 10 | | | | | 15 | |

| Ile | Phe | Gly | Pro | Asp | Phe | Pro | Phe | Ala | Phe | Asp | Asp | Trp | Leu | Glu | His |
|---|---|---|---|---|---|---|---|---|---|---|---|---|---|---|---|
| | | | 20 | | | | | 25 | | | | | 30 | | |

| Pro | Ala | Gly | Leu | Gly | Ser | Ile | Pro | Ala | Ala | Arg | His | Gly | Glu | Glu | Val |
| | | | 35 | | | | | 40 | | | | | 45 | | |

| Ala | Ile | Val | Gly | Ala | Gly | Ile | Ala | Gly | Leu | Val | Ala | Ala | Tyr | Glu | Leu |
| | 50 | | | | | 55 | | | | | 60 | | | | |

| Met | Lys | Leu | Gly | Leu | Lys | Pro | Val | Val | Tyr | Glu | Ala | Ser | Lys | Met | Gly |
| 65 | | | | | 70 | | | | | 75 | | | | | 80 |

| Gly | Arg | Leu | Arg | Ser | Gln | Ala | Phe | Asn | Gly | Thr | Asp | Gly | Ile | Ile | Ala |
| | | | | 85 | | | | | 90 | | | | | 95 | |

| Glu | Leu | Gly | Gly | Met | Arg | Phe | Pro | Val | Ser | Ser | Thr | Ala | Phe | Tyr | His |
| | | | 100 | | | | | 105 | | | | | 110 | | |

| Tyr | Val | Asp | Lys | Leu | Gly | Leu | Glu | Thr | Lys | Pro | Phe | Pro | Asn | Pro | Leu |
| | | | 115 | | | | | 120 | | | | | 125 | | |

| Thr | Pro | Ala | Ser | Arg | Ser | Thr | Val | Ile | Asp | Leu | Glu | Gly | Gln | Thr | Tyr |
| 130 | | | | | 135 | | | | | 140 | | | | | |

| Tyr | Ala | Glu | Lys | Ala | Ala | Asp | Leu | Pro | Ala | Leu | Phe | Gln | Glu | Val | Thr |
| 145 | | | | | 150 | | | | | 155 | | | | | 160 |

| Asp | Ala | Trp | Ala | Asp | Ala | Leu | Glu | Ser | Gly | Ala | Arg | Phe | Gly | Asp | Ile |
| | | | | 165 | | | | | 170 | | | | | 175 | |

| Gln | Gln | Ala | Ile | Arg | Asp | Arg | Asp | Val | Pro | Arg | Leu | Lys | Glu | Leu | Trp |
| | | | 180 | | | | | 185 | | | | | 190 | | |

| Asn | Thr | Leu | Val | Pro | Leu | Trp | Asp | Asp | Arg | Thr | Phe | Tyr | Asp | Phe | Val |
| | | | 195 | | | | | 200 | | | | | 205 | | |

| Ala | Thr | Ser | Lys | Ala | Phe | Ala | Lys | Leu | Ser | Phe | Gln | His | Arg | Glu | Val |
| 210 | | | | | 215 | | | | | 220 | | | | | |

| Phe | Gly | Gln | Val | Gly | Phe | Gly | Thr | Gly | Gly | Trp | Asp | Ser | Asp | Phe | Pro |
| 225 | | | | | 230 | | | | | 235 | | | | | 240 |

| Asn | Ser | Met | Leu | Glu | Ile | Phe | Arg | Val | Val | Met | Thr | Asn | Cys | Asp | Asp |
| | | | | 245 | | | | | 250 | | | | | 255 | |

| His | Gln | His | Leu | Val | Val | Gly | Val | Glu | Gln | Val | Pro | Gln | Gly | Ile |
| | | | 260 | | | | | 265 | | | | | 270 | | |

| Trp | Arg | His | Val | Pro | Glu | Arg | Cys | Ala | His | Trp | Pro | Glu | Gly | Thr | Ser |
| | | | 275 | | | | | 280 | | | | | 285 | | |

| Leu | Ser | Ser | Leu | His | Gly | Gly | Ala | Pro | Arg | Thr | Gly | Val | Lys | Arg | Ile |
| | 290 | | | | | 295 | | | | | 300 | | | | |

| Ala | Arg | Ala | Ser | Asp | Gly | Arg | Leu | Ala | Val | Thr | Asp | Asn | Trp | Gly | Asp |
| 305 | | | | | 310 | | | | | 315 | | | | | 320 |

| Cys | Arg | His | Tyr | Ala | Ala | Val | Leu | Thr | Thr | Cys | Gln | Ser | Trp | Leu | Leu |
| | | | | 325 | | | | | 330 | | | | | 335 | |

| Thr | Thr | Gln | Ile | Asp | Cys | Glu | Glu | Ser | Leu | Phe | Ser | Gln | Lys | Met | Trp |
| | | | 340 | | | | | 345 | | | | | 350 | | |

| Met | Ala | Leu | Asp | Arg | Thr | Arg | Tyr | Met | Gln | Ser | Ser | Lys | Thr | Phe | Val |
| | | | 355 | | | | | 360 | | | | | 365 | | |

| Met | Val | Asp | Arg | Pro | Phe | Trp | Lys | Asp | Lys | Asp | Pro | Glu | Thr | Gly | Arg |
| | 370 | | | | | 375 | | | | | 380 | | | | |

```
Asp Leu Met Ser Met Thr Leu Thr Asp Arg Leu Thr Arg Gly Thr Tyr
385                 390                 395                 400

Leu Phe Asp Asn Gly Asp Asp Lys Pro Gly Val Ile Cys Leu Ser Tyr
            405                 410                 415

Ala Trp Met Ser Asp Ala Leu Lys Met Leu Pro His Pro Val Glu Lys
        420                 425                 430

Arg Val Gln Leu Ala Leu Asp Ala Leu Lys Lys Ile Tyr Pro Lys Thr
    435                 440                 445

Asp Ile Ala Gly His Ile Ile Gly Asp Pro Ile Thr Ile Ser Trp Glu
450                 455                 460

Ala Asp Pro His Phe Leu Gly Ala Ser Lys Gly Ala Leu Pro Gly His
465                 470                 475                 480

Tyr Arg Tyr Asn Gln Arg Met Tyr Ala His Phe Met Gln Ala Gln Met
            485                 490                 495

Pro Val Glu Gln Arg Gly Ile Phe Ile Ala Gly Asp Val Ser Trp
        500                 505                 510

Thr Pro Ala Trp Val Glu Gly Ala Val Gln Thr Ser Leu Asn Ala Val
        515                 520                 525

Trp Gly Ile Met Asn His Phe Gly Gly Lys Thr His Ala Asp Asn Pro
530                 535                 540

Gly Pro Gly Asp Val Phe Asp Glu Ile Gly Gln Ile Ala Leu Ala Asp
545                 550                 555                 560

<210> SEQ ID NO 3
<211> LENGTH: 1683
<212> TYPE: DNA
<213> ORGANISM: Artificial
<220> FEATURE:
<223> OTHER INFORMATION: Mutated L-amino acid Oxydase
<220> FEATURE:
<221> NAME/KEY: CDS
<222> LOCATION: (1)..(1680)
<223> OTHER INFORMATION:

<400> SEQUENCE: 3 atg aac aag aac aac cgc cac ccg gcc gac ggt aaa aaa ccg atc acc      48
Met Asn Lys Asn Asn Arg His Pro Ala Asp Gly Lys Lys Pro Ile Thr
1               5                   10                  15 atc ttc ggc ccg gac ttc cct ttt gcc ttc gat gat tgg ctg gaa cac      96
Ile Phe Gly Pro Asp Phe Pro Phe Ala Phe Asp Asp Trp Leu Glu His
            20                  25                  30 ccg gct ggc ctg ggt agc atc cca gcc gcg cgt cat ggt gaa gaa gtg     144
Pro Ala Gly Leu Gly Ser Ile Pro Ala Ala Arg His Gly Glu Glu Val
        35                  40                  45 gcg atc gtg ggc gcc ggc atc gcc ggg ctg gtg gcg gcc tac gag ctg     192
Ala Ile Val Gly Ala Gly Ile Ala Gly Leu Val Ala Ala Tyr Glu Leu
    50                  55                  60 atg aag ctg ggc ctc aaa ccg gtg gtc tac gag gcg tcg aag atg ggt     240
Met Lys Leu Gly Leu Lys Pro Val Val Tyr Glu Ala Ser Lys Met Gly
65                  70                  75                  80 ggg cgg ctg cgc tcg cag gcc ttc aac ggc acc gac ggt atc atc gcc     288
Gly Arg Leu Arg Ser Gln Ala Phe Asn Gly Thr Asp Gly Ile Ile Ala
            85                  90                  95 gag ctg ggc gga atg cgc ttt ccg gtg tcg tcc acg gcg ttc tac cac     336
Glu Leu Gly Gly Met Arg Phe Pro Val Ser Ser Thr Ala Phe Tyr His
            100                 105                 110 tac gtc gac aag ctg ggc ctg gaa acc aag cct ttc ccc aac ccg ctc     384
Tyr Val Asp Lys Leu Gly Leu Glu Thr Lys Pro Phe Pro Asn Pro Leu
        115                 120                 125
```

-continued

```
acc cct gcc tca cgc agc acg gta atc gat ctg gaa ggc cag acc tac        432
Thr Pro Ala Ser Arg Ser Thr Val Ile Asp Leu Glu Gly Gln Thr Tyr
    130                 135                 140 tac gcg gaa aaa gcc gcc gac ttg ccg gcc ctg ttc cag gaa gtt acc        480
Tyr Ala Glu Lys Ala Ala Asp Leu Pro Ala Leu Phe Gln Glu Val Thr
145                 150                 155                 160 gat gcc tgg gcc gac gcc ctg gaa agc ggt gcg cgc ttt ggt gac atc        528
Asp Ala Trp Ala Asp Ala Leu Glu Ser Gly Ala Arg Phe Gly Asp Ile
                165                 170                 175 cag caa gca att cgt gac cgt gac gtg cct cgc ttg aaa gaa ctg tgg        576
Gln Gln Ala Ile Arg Asp Arg Asp Val Pro Arg Leu Lys Glu Leu Trp
            180                 185                 190 aac acc ctg gtg ccg ctg tgg gac gac cgc act ttc tac gac ttc gtc        624
Asn Thr Leu Val Pro Leu Trp Asp Asp Arg Thr Phe Tyr Asp Phe Val
        195                 200                 205 gcc acc tcc aaa gcc ttc gcc aaa ctg agt ttc cag cac cgc gaa gtg        672
Ala Thr Ser Lys Ala Phe Ala Lys Leu Ser Phe Gln His Arg Glu Val
    210                 215                 220 ttc ggc cag gtg ggc ttc ggc acc ggt ggt tgg gat tcg gac ttc ccc        720
Phe Gly Gln Val Gly Phe Gly Thr Gly Gly Trp Asp Ser Asp Phe Pro
225                 230                 235                 240 aac tcg atg ctg gaa atc ttc cgt gtg gtg atg acc aat atc gac gac        768
Asn Ser Met Leu Glu Ile Phe Arg Val Val Met Thr Asn Ile Asp Asp
                245                 250                 255 cac caa cac ctg gtg gtc ggc ggc gtc gag caa gtg ccg cag ggc atc        816
His Gln His Leu Val Val Gly Gly Val Glu Gln Val Pro Gln Gly Ile
            260                 265                 270 tgg cgc cat gtg cca gag cgt tgt gcg cac tgg ccc gaa ggt acc agc        864
Trp Arg His Val Pro Glu Arg Cys Ala His Trp Pro Glu Gly Thr Ser
        275                 280                 285 ctg agc tcg ctg cac ggc ggt gca ccg cgc acc ggc gtc aag cgc att        912
Leu Ser Ser Leu His Gly Gly Ala Pro Arg Thr Gly Val Lys Arg Ile
    290                 295                 300 gcc cgc gcc agc gac ggc cgc ctg gca gtc acc gac aac tgg ggc gac        960
Ala Arg Ala Ser Asp Gly Arg Leu Ala Val Thr Asp Asn Trp Gly Asp
305                 310                 315                 320 tgc cgc cat tac gcg gcg gtg ctg acg acc tgc cag agt tgg ctg ctg       1008
Cys Arg His Tyr Ala Ala Val Leu Thr Thr Cys Gln Ser Trp Leu Leu
                325                 330                 335 acc acc cag atc gac tgt gaa gag tcg ttg ttc tcg cag aag atg tgg       1056
Thr Thr Gln Ile Asp Cys Glu Glu Ser Leu Phe Ser Gln Lys Met Trp
            340                 345                 350 atg gcc ctg gac cgc acc cgc tac atg caa tcg tcg aaa acc ttc gtc       1104
Met Ala Leu Asp Arg Thr Arg Tyr Met Gln Ser Ser Lys Thr Phe Val
        355                 360                 365 atg gtc gac cgg ccg ttc tgg aaa gac aaa gac cca gaa acc ggt cgc       1152
Met Val Asp Arg Pro Phe Trp Lys Asp Lys Asp Pro Glu Thr Gly Arg
    370                 375                 380 gac ctg atg agc atg acc ctc acc gac cgg ctg acc cgt ggc acc tac       1200
Asp Leu Met Ser Met Thr Leu Thr Asp Arg Leu Thr Arg Gly Thr Tyr
385                 390                 395                 400 ctg ttc gat aac ggc gac gac aag cca ggg gtg atc tgc ctg tcc tac       1248
Leu Phe Asp Asn Gly Asp Asp Lys Pro Gly Val Ile Cys Leu Ser Tyr
                405                 410                 415 gcg tgg atg agc gat gcc ctg aag atg ctc ccg cac ccg gtg gaa aaa       1296
Ala Trp Met Ser Asp Ala Leu Lys Met Leu Pro His Pro Val Glu Lys
            420                 425                 430 cgc gtg caa ctg gca ctc gat gca ttg aaa aag atc tac ccg aaa acc       1344
Arg Val Gln Leu Ala Leu Asp Ala Leu Lys Lys Ile Tyr Pro Lys Thr
        435                 440                 445
```

```
gat atc gcc ggg cat atc atc ggc gac cct att acc att tcc tgg gaa      1392
Asp Ile Ala Gly His Ile Ile Gly Asp Pro Ile Thr Ile Ser Trp Glu
450                 455                 460 gcc gac ccg cac ttc ctc ggt gca tcc aaa ggc gcg ctg ccg ggc cac      1440
Ala Asp Pro His Phe Leu Gly Ala Ser Lys Gly Ala Leu Pro Gly His
465                 470                 475                 480 tat cgc tac aac cag cgg atg tac gcg cac ttc atg cag gcg cag atg      1488
Tyr Arg Tyr Asn Gln Arg Met Tyr Ala His Phe Met Gln Ala Gln Met
                485                 490                 495 cca gtc gag cag cgt ggc att ttc att gcc ggc gac gac gtg tcg tgg      1536
Pro Val Glu Gln Arg Gly Ile Phe Ile Ala Gly Asp Asp Val Ser Trp
            500                 505                 510 acc ccg gcc tgg gtg gaa ggc gcg gtg cag acc tcg ctc aat gcc gtg      1584
Thr Pro Ala Trp Val Glu Gly Ala Val Gln Thr Ser Leu Asn Ala Val
        515                 520                 525 tgg ggt atc atg aat cac ttt ggt ggc aag acc cac gcg gac aac ccc      1632
Trp Gly Ile Met Asn His Phe Gly Gly Lys Thr His Ala Asp Asn Pro
530                 535                 540 ggc cct ggc gac gtg ttc gat gag atc ggc caa atc gcc ctg gcg gac      1680
Gly Pro Gly Asp Val Phe Asp Glu Ile Gly Gln Ile Ala Leu Ala Asp
545                 550                 555                 560 tga                                                                   1683

<210> SEQ ID NO 4
<211> LENGTH: 560
<212> TYPE: PRT
<213> ORGANISM: Artificial
<220> FEATURE:
<223> OTHER INFORMATION: Mutated L-amino acid Oxydase

<400> SEQUENCE: 4

Met Asn Lys Asn Asn Arg His Pro Ala Asp Gly Lys Lys Pro Ile Thr
1               5                   10                  15

Ile Phe Gly Pro Asp Phe Pro Phe Ala Phe Asp Asp Trp Leu Glu His
            20                  25                  30

Pro Ala Gly Leu Gly Ser Ile Pro Ala Ala Arg His Gly Glu Glu Val
        35                  40                  45

Ala Ile Val Gly Ala Gly Ile Ala Gly Leu Val Ala Ala Tyr Glu Leu
    50                  55                  60

Met Lys Leu Gly Leu Lys Pro Val Val Tyr Glu Ala Ser Lys Met Gly
65                  70                  75                  80

Gly Arg Leu Arg Ser Gln Ala Phe Asn Gly Thr Asp Gly Ile Ile Ala
                85                  90                  95

Glu Leu Gly Gly Met Arg Phe Pro Val Ser Ser Thr Ala Phe Tyr His
            100                 105                 110

Tyr Val Asp Lys Leu Gly Leu Glu Thr Lys Pro Phe Pro Asn Pro Leu
        115                 120                 125

Thr Pro Ala Ser Arg Ser Thr Val Ile Asp Leu Glu Gly Gln Thr Tyr
    130                 135                 140

Tyr Ala Glu Lys Ala Ala Asp Leu Pro Ala Leu Phe Gln Glu Val Thr
145                 150                 155                 160

Asp Ala Trp Ala Asp Ala Leu Glu Ser Gly Ala Arg Phe Gly Asp Ile
                165                 170                 175

Gln Gln Ala Ile Arg Asp Arg Asp Val Pro Arg Leu Lys Glu Leu Trp
            180                 185                 190

Asn Thr Leu Val Pro Leu Trp Asp Asp Arg Thr Phe Tyr Asp Phe Val
        195                 200                 205
```

```
Ala Thr Ser Lys Ala Phe Ala Lys Leu Ser Phe Gln His Arg Glu Val
    210                 215                 220

Phe Gly Gln Val Gly Phe Gly Thr Gly Gly Trp Asp Ser Asp Phe Pro
225                 230                 235                 240

Asn Ser Met Leu Glu Ile Phe Arg Val Val Met Thr Asn Ile Asp Asp
                245                 250                 255

His Gln His Leu Val Val Gly Val Glu Gln Val Pro Gln Gly Ile
            260                 265                 270

Trp Arg His Val Pro Glu Arg Cys Ala His Trp Pro Glu Gly Thr Ser
        275                 280                 285

Leu Ser Ser Leu His Gly Gly Ala Pro Arg Thr Gly Val Lys Arg Ile
    290                 295                 300

Ala Arg Ala Ser Asp Gly Arg Leu Ala Val Thr Asp Asn Trp Gly Asp
305                 310                 315                 320

Cys Arg His Tyr Ala Ala Val Leu Thr Thr Cys Gln Ser Trp Leu Leu
                325                 330                 335

Thr Thr Gln Ile Asp Cys Glu Glu Ser Leu Phe Ser Gln Lys Met Trp
            340                 345                 350

Met Ala Leu Asp Arg Thr Arg Tyr Met Gln Ser Ser Lys Thr Phe Val
        355                 360                 365

Met Val Asp Arg Pro Phe Trp Lys Asp Lys Asp Pro Glu Thr Gly Arg
    370                 375                 380

Asp Leu Met Ser Met Thr Leu Thr Asp Arg Leu Thr Arg Gly Thr Tyr
385                 390                 395                 400

Leu Phe Asp Asn Gly Asp Asp Lys Pro Gly Val Ile Cys Leu Ser Tyr
                405                 410                 415

Ala Trp Met Ser Asp Ala Leu Lys Met Leu Pro His Pro Val Glu Lys
            420                 425                 430

Arg Val Gln Leu Ala Leu Asp Ala Leu Lys Lys Ile Tyr Pro Lys Thr
        435                 440                 445

Asp Ile Ala Gly His Ile Ile Gly Asp Pro Ile Thr Ile Ser Trp Glu
    450                 455                 460

Ala Asp Pro His Phe Leu Gly Ala Ser Lys Gly Ala Leu Pro Gly His
465                 470                 475                 480

Tyr Arg Tyr Asn Gln Arg Met Tyr Ala His Phe Met Gln Ala Gln Met
                485                 490                 495

Pro Val Glu Gln Arg Gly Ile Phe Ile Ala Gly Asp Val Ser Trp
            500                 505                 510

Thr Pro Ala Trp Val Glu Gly Ala Val Gln Thr Ser Leu Asn Ala Val
        515                 520                 525

Trp Gly Ile Met Asn His Phe Gly Gly Lys Thr His Ala Asp Asn Pro
    530                 535                 540

Gly Pro Gly Asp Val Phe Asp Glu Ile Gly Gln Ile Ala Leu Ala Asp
545                 550                 555                 560

<210> SEQ ID NO 5
<211> LENGTH: 560
<212> TYPE: PRT
<213> ORGANISM: Pseudomonas putida

<400> SEQUENCE: 5

Met Asn Lys Lys Asn Arg His Pro Ala Asp Gly Lys Lys Pro Ile Thr
1               5                   10                  15

Ile Phe Gly Pro Asp Phe Pro Phe Ala Phe Asp Asp Trp Leu Glu His
```

```
                20                  25                  30
Pro Ala Gly Leu Gly Ser Ile Pro Ala Glu Arg His Gly Glu Val
            35                  40                  45
Ala Ile Val Gly Ala Gly Ile Ala Gly Leu Val Ala Ala Tyr Glu Leu
 50                  55                  60
Met Lys Leu Gly Leu Lys Pro Val Val Tyr Glu Ala Ser Lys Leu Gly
 65                  70                  75                  80
Gly Arg Leu Arg Ser Gln Ala Phe Asn Gly Thr Asp Gly Ile Val Ala
                85                  90                  95
Glu Leu Gly Gly Met Arg Phe Pro Val Ser Ser Thr Ala Phe Tyr His
                100                 105                 110
Tyr Val Asp Lys Leu Gly Leu Glu Thr Lys Pro Phe Pro Asn Pro Leu
            115                 120                 125
Thr Pro Ala Ser Gly Ser Thr Val Ile Asp Leu Glu Gly Gln Thr Tyr
 130                 135                 140
Tyr Ala Glu Lys Pro Thr Asp Leu Pro Gln Leu Phe His Glu Val Ala
145                 150                 155                 160
Asp Ala Trp Ala Asp Ala Leu Glu Ser Gly Ala Gln Phe Ala Asp Ile
                165                 170                 175
Gln Gln Ala Ile Arg Asp Arg Asp Val Pro Arg Leu Lys Glu Leu Trp
                180                 185                 190
Asn Lys Leu Val Pro Leu Trp Asp Asp Arg Thr Phe Tyr Asp Phe Val
            195                 200                 205
Ala Thr Ser Arg Ser Phe Ala Lys Leu Ser Phe Gln His Arg Glu Val
 210                 215                 220
Phe Gly Gln Val Gly Phe Gly Thr Gly Gly Trp Asp Ser Asp Phe Pro
225                 230                 235                 240
Asn Ser Met Leu Glu Ile Phe Arg Val Val Met Thr Asn Cys Asp Asp
                245                 250                 255
His Gln His Leu Val Val Gly Val Glu Gln Val Pro Gln Gly Ile
                260                 265                 270
Trp Arg His Val Pro Glu Arg Cys Val His Trp Pro Glu Gly Thr Ser
            275                 280                 285
Leu Ser Thr Leu His Gly Gly Ala Pro Arg Thr Gly Val Lys Arg Ile
 290                 295                 300
Ala Arg Ala Ser Asp Gly Arg Leu Ala Val Thr Asp Asn Trp Gly Asp
305                 310                 315                 320
Thr Arg His Tyr Ser Ala Val Leu Ala Thr Cys Gln Thr Trp Leu Leu
                325                 330                 335
Thr Thr Gln Ile Asp Cys Glu Glu Ser Leu Phe Ser Gln Lys Met Trp
                340                 345                 350
Met Ala Leu Asp Arg Thr Arg Tyr Met Gln Ser Ser Lys Thr Phe Val
            355                 360                 365
Met Val Asp Arg Pro Phe Trp Lys Asp Lys Asp Pro Glu Thr Gly Arg
 370                 375                 380
Asp Leu Leu Ser Met Thr Leu Thr Asp Arg Leu Thr Arg Gly Thr Tyr
385                 390                 395                 400
Leu Phe Asp Asn Gly Asn Asp Lys Pro Gly Val Ile Cys Leu Ser Tyr
                405                 410                 415
Ser Trp Met Ser Asp Ala Leu Lys Met Leu Pro His Pro Val Glu Lys
                420                 425                 430
Arg Val Gln Leu Ala Leu Asp Ala Leu Lys Lys Ile Tyr Pro Lys Thr
            435                 440                 445
```

```
Asp Ile Ala Gly His Ile Ile Gly Asp Pro Ile Thr Val Ser Trp Glu
    450                 455                 460
Ala Asp Pro Tyr Phe Leu Gly Ala Phe Lys Gly Ala Leu Pro Gly His
465                 470                 475                 480
Tyr Arg Tyr Asn Gln Arg Met Tyr Ala His Phe Met Gln Gln Asp Met
                485                 490                 495
Pro Ala Glu Gln Arg Gly Ile Phe Ile Ala Gly Asp Val Ser Trp
            500                 505                 510
Thr Pro Ala Trp Val Glu Gly Ala Val Gln Thr Ser Leu Asn Ala Val
            515                 520                 525
Trp Gly Ile Met Asn His Phe Gly Gly His Thr His Pro Asp Asn Pro
        530                 535                 540
Gly Pro Gly Asp Val Phe Asn Glu Ile Gly Pro Ile Ala Leu Ala Asp
545                 550                 555                 560

<210> SEQ ID NO 6
<211> LENGTH: 560
<212> TYPE: PRT
<213> ORGANISM: Pseudomonas entomophila L48

<400> SEQUENCE: 6

Met Asn Lys Lys Asn Arg His Pro Ala Asp Gly Lys Lys Pro Ile Thr
1               5                   10                  15
Ile Phe Gly Pro Asp Phe Pro Phe Ala Phe Asp Asp Trp Leu Glu His
            20                  25                  30
Leu Ala Gly Leu Gly Ser Ile Pro Lys Glu Arg His Gly Glu Glu Val
        35                  40                  45
Ala Ile Val Gly Gly Gly Ile Ala Gly Leu Val Ala Ala Tyr Glu Leu
    50                  55                  60
Met Lys Leu Gly Leu Lys Pro Val Val Tyr Glu Ala Ser Lys Leu Gly
65              70                  75                  80
Gly Arg Leu Arg Ser Gln Ala Phe Asn Gly Thr Asp Gly Ile Val Ala
                85                  90                  95
Glu Leu Gly Gly Met Arg Phe Pro Val Ser Ser Thr Ala Phe Tyr His
            100                 105                 110
Tyr Val Asp Lys Leu Gly Leu Glu Thr Lys Pro Phe Pro Asn Pro Leu
        115                 120                 125
Thr Pro Ala Ser Gly Ser Thr Val Ile Asp Leu Glu Gly Gln Thr Tyr
    130                 135                 140
Tyr Ala Glu Lys Ser Ala Asp Leu Pro Gln Leu Phe His Glu Val Ala
145                 150                 155                 160
Asp Ala Trp Ala Asp Ala Leu Glu Ser Gly Ala Gln Phe Gly Asp Ile
                165                 170                 175
Gln Gln Ala Ile Arg Asp Arg Asp Val Pro Arg Leu Lys Asp Leu Trp
            180                 185                 190
Asn Lys Leu Val Pro Leu Trp Asp Asp Arg Thr Phe Tyr Asp Phe Val
        195                 200                 205
Ala Thr Ser Arg Ser Phe Ala Lys Leu Ser Phe Gln His Arg Glu Val
    210                 215                 220
Phe Gly Gln Val Gly Phe Gly Thr Gly Gly Trp Asp Ser Asp Phe Pro
225                 230                 235                 240
Asn Ser Met Leu Glu Ile Phe Arg Val Val Met Thr Asn Cys Asp Asp
                245                 250                 255
His Gln His Leu Val Val Gly Gly Val Glu Gln Val Pro Gln Gly Ile
```

-continued

```
                260                 265                 270
Trp Arg His Val Pro Glu Arg Cys Ala His Trp Pro Ala Gly Thr Ser
            275                 280                 285

Leu Lys Thr Leu His Ser Gly Ala Pro Arg Ala Gly Val Lys Arg Ile
        290                 295                 300

Ala Arg Ala Ala Asp Gly Arg Leu Ala Val Thr Asp Asn Tyr Gly Asp
305                 310                 315                 320

Thr Arg His Tyr Ala Ala Val Leu Thr Thr Cys Gln Ser Trp Leu Leu
                325                 330                 335

Thr Thr Gln Ile Asp Cys Glu Glu Ser Leu Phe Ser Gln Lys Met Trp
            340                 345                 350

Met Ala Leu Asp Arg Thr Arg Tyr Met Gln Ser Ser Lys Thr Phe Val
        355                 360                 365

Met Val Asp Arg Pro Phe Trp Lys Asp Lys Asp Pro Glu Thr Gly Arg
    370                 375                 380

Asp Leu Met Ser Met Thr Leu Thr Asp Arg Leu Thr Arg Gly Thr Tyr
385                 390                 395                 400

Leu Phe Asp Asn Gly Asp Asp Lys Pro Gly Val Ile Cys Leu Ser Tyr
                405                 410                 415

Ala Trp Met Ser Asp Ala Leu Lys Met Leu Pro His Pro Thr Glu Lys
            420                 425                 430

Arg Val Gln Leu Ala Leu Asp Ala Leu Lys Lys Ile Tyr Pro Lys Thr
        435                 440                 445

Asp Ile Ala Gly His Ile Ile Gly Asp Pro Ile Thr Ile Ser Trp Glu
    450                 455                 460

Ala Asp Pro His Phe Leu Gly Ala Phe Lys Gly Ala Leu Pro Gly His
465                 470                 475                 480

Tyr Arg Tyr Asn Gln Arg Met Tyr Ala His Phe Met Gln Gln Asp Met
                485                 490                 495

Pro Ala Glu Gln Arg Gly Ile Phe Ile Ala Gly Asp Asp Val Ser Trp
            500                 505                 510

Thr Pro Ala Trp Val Glu Gly Ala Val Gln Thr Ser Leu Asn Ala Val
        515                 520                 525

Trp Gly Ile Met Asn His Phe Gly Gly Gln Thr His Pro Asp Asn Pro
    530                 535                 540

Gly Pro Gly Asp Val Phe His Glu Ile Gly Pro Ile Ala Leu Ala Asp
545                 550                 555                 560

<210> SEQ ID NO 7
<211> LENGTH: 560
<212> TYPE: PRT
<213> ORGANISM: Pseudomonas fluorescens Pf-5

<400> SEQUENCE: 7

Met Asn Lys Asn Arg His Pro Ala Asp Gly Lys Lys Pro Ile Thr
1               5                   10                  15

Ile Phe Gly Pro Asp Phe Pro Phe Ala Phe Asp Trp Ile Glu His
            20                  25                  30

Pro Ala Gly Leu Gly Ser Ile Pro Gln Ala Arg His Gly Thr Glu Val
        35                  40                  45

Ala Ile Val Gly Ala Gly Ile Ala Gly Leu Val Ala Ala Tyr Glu Leu
    50                  55                  60

Met Lys Leu Gly Leu Lys Pro Val Val Tyr Glu Ala Ser Lys Met Gly
65                  70                  75                  80
```

```
Gly Arg Leu Arg Ser Gln Ala Phe Glu Gly Ala Glu Gly Ile Ile Ala
             85                  90                  95
Glu Leu Gly Gly Met Arg Phe Pro Val Ser Ser Thr Ala Phe Tyr His
            100                 105                 110
Tyr Val Asp Lys Leu Gly Leu Glu Thr Lys Pro Phe Pro Asn Pro Leu
        115                 120                 125
Thr Pro Ala Ser Gly Ser Thr Val Ile Asp Leu Glu Gly Gln Thr His
    130                 135                 140
Tyr Ala Gln Lys Leu Ala Asp Leu Pro Ala Leu Phe Gln Glu Val Ala
145                 150                 155                 160
Asp Ala Trp Ala Asp Ala Leu Glu Asp Gly Ser Arg Phe Ser Glu Ile
                165                 170                 175
Gln Gln Ala Ile Arg Asp Arg Asp Val Pro Arg Leu Lys Glu Leu Trp
            180                 185                 190
Asn Thr Leu Val Pro Leu Trp Asp Asp Arg Thr Phe Tyr Asp Phe Val
        195                 200                 205
Ala Thr Ser Lys Ala Phe Ala Lys Leu Ser Phe His His Arg Glu Val
    210                 215                 220
Phe Gly Gln Val Gly Phe Gly Thr Gly Gly Trp Asp Ser Asp Phe Pro
225                 230                 235                 240
Asn Ser Met Leu Glu Ile Phe Arg Val Val Met Thr Asn Cys Asp Asp
                245                 250                 255
His Gln His Leu Val Val Gly Val Glu Gln Val Pro Leu Gly Ile
            260                 265                 270
Trp Arg His Val Pro Glu Arg Cys Ala His Trp Pro Ala Gly Thr Ser
        275                 280                 285
Leu Ser Ser Leu His His Gly Ala Pro Arg Thr Gly Val Lys Arg Ile
    290                 295                 300
Ala Arg Ala Ala Asp Gly Arg Phe Ser Val Thr Asp Asn Trp Gly Asp
305                 310                 315                 320
Thr Arg Glu Tyr Ala Ala Val Leu Thr Thr Cys Gln Ser Trp Leu Leu
                325                 330                 335
Thr Thr Gln Ile Glu Cys Glu Glu Ser Leu Phe Ser Gln Lys Met Trp
            340                 345                 350
Met Ala Leu Asp Arg Thr Arg Tyr Met Gln Ser Ser Lys Thr Phe Val
    355                 360                 365
Met Val Asp Arg Pro Phe Trp Lys Asp Lys Asp Pro Glu Thr Gly Arg
370                 375                 380
Asp Leu Met Ser Met Thr Leu Thr Asp Arg Leu Thr Arg Gly Thr Tyr
385                 390                 395                 400
Leu Phe Asp Asn Gly Asp Asp Lys Pro Gly Val Ile Cys Leu Ser Tyr
                405                 410                 415
Ser Trp Met Ser Asp Ala Leu Lys Met Leu Pro Gln Pro Val Glu Lys
            420                 425                 430
Arg Val Lys Leu Ala Leu Asp Ala Leu Lys Lys Ile Tyr Pro Lys Val
    435                 440                 445
Asp Ile Ala Ser Arg Ile Ile Gly Asp Pro Ile Thr Val Ser Trp Glu
450                 455                 460
Ala Asp Pro His Phe Leu Gly Ala Phe Lys Gly Ala Leu Pro Gly His
465                 470                 475                 480
Tyr Arg Tyr Asn Gln Arg Met Tyr Ala His Phe Met Gln Asp Asp Met
                485                 490                 495
Pro Ala Glu Gln Arg Gly Ile Phe Ile Ala Gly Asp Asp Val Ser Trp
```

```
                500              505              510
Thr Pro Ala Trp Val Glu Gly Ala Val Gln Thr Ser Leu Asn Ala Val
            515                  520              525

Trp Gly Ile Met Lys His Phe Gly Gly Ala Thr His Ala Glu Asn Pro
            530                  535              540

Gly Pro Gly Asp Val Phe His Glu Ile Gly Pro Ile Ala Leu Ala Asp
545                  550              555                  560
```

<210> SEQ ID NO 8
<211> LENGTH: 560
<212> TYPE: PRT
<213> ORGANISM: Pseudomonas fluorescens

<400> SEQUENCE: 8

```
Met Asn Lys Asn Asn Arg His Pro Ala Asp Gly Lys Lys Pro Ile Thr
1               5                   10                  15

Ile Phe Gly Pro Asp Phe Pro Phe Ala Phe Asp Trp Ile Glu His
            20                  25                  30

Pro Ala Gly Leu Gly Ser Ile Pro Ala His Ser His Gly Ala Glu Val
            35                  40                  45

Ala Ile Val Gly Ala Gly Ile Ala Gly Leu Val Ala Ala Tyr Glu Leu
50                  55                  60

Met Lys Leu Gly Leu Lys Pro Val Val Tyr Glu Ala Ser Lys Met Gly
65                  70                  75                  80

Gly Arg Leu Arg Ser Gln Ala Phe Asn Gly Ala Glu Gly Val Ile Ala
            85                  90                  95

Glu Leu Gly Gly Met Arg Phe Pro Val Ser Ser Thr Ala Phe Tyr His
            100                 105                 110

Tyr Val Asp Lys Leu Gly Leu Glu Thr Lys Pro Phe Pro Asn Pro Leu
            115                 120                 125

Thr Pro Ala Ser Gly Ser Thr Val Ile Asp Leu Glu Gly Gln Thr Tyr
            130                 135                 140

Tyr Ala Gln Lys Leu Ala Asp Leu Pro Ala Leu Phe Gln Glu Val Ala
145                 150                 155                 160

Asp Ala Trp Ala Asp Ala Leu Glu Asp Gly Ser Arg Phe Gly Asp Ile
            165                 170                 175

Gln Gln Ala Ile Arg Asp Arg Asp Val Pro Arg Leu Lys Glu Leu Trp
            180                 185                 190

Asn Thr Leu Val Pro Leu Trp Asp Asp Arg Thr Phe Tyr Asp Phe Val
            195                 200                 205

Ala Thr Ser Lys Ala Phe Ala Lys Leu Ser Phe Gln His Arg Glu Val
210                 215                 220

Phe Gly Gln Val Gly Phe Gly Thr Gly Gly Trp Asp Ser Asp Phe Pro
225                 230                 235                 240

Asn Ser Met Leu Glu Ile Phe Arg Val Val Met Thr Asn Cys Asp Asp
            245                 250                 255

His Gln His Leu Val Val Gly Val Glu Val Pro His Gly Ile
            260                 265                 270

Trp Asn His Val Pro Glu Arg Cys Val His Trp Pro Gln Gly Thr Ser
            275                 280                 285

Leu Asn Ser Leu His Leu Gly Ala Pro Arg Ser Gly Val Lys Arg Ile
            290                 295                 300

Ala Arg Ala Ala Asp Gly Gln Phe Ser Val Thr Asp Val Trp Asp Asn
305                 310                 315                 320
```

```
Thr Arg Glu Tyr Ala Val Leu Val Thr Cys Gln Ser Trp Leu Leu
                325                 330                 335

Thr Thr Gln Ile Glu Cys Glu Glu Ala Leu Phe Ser Gln Lys Met Trp
            340                 345                 350

Met Ala Leu Asp Arg Thr Arg Tyr Met Gln Ser Ser Lys Thr Phe Val
            355                 360                 365

Met Val Asp Arg Pro Phe Trp Lys Asp Lys Pro Glu Thr Gly Arg
370                 375                 380

Asp Leu Met Ser Met Thr Leu Thr Asp Arg Leu Thr Arg Gly Thr Tyr
385                 390                 395                 400

Leu Phe Asp Asn Gly Asp Asp Lys Pro Gly Val Ile Cys Leu Ser Tyr
                405                 410                 415

Ser Trp Met Ser Asp Ala Leu Lys Met Leu Pro His Pro Val Glu Lys
            420                 425                 430

Arg Val Lys Leu Ala Leu Asp Ala Leu Lys Lys Ile Tyr Pro Lys Val
            435                 440                 445

Asp Ile Ala Ala Arg Ile Ile Gly Asp Pro Ile Thr Val Ser Trp Glu
450                 455                 460

Ala Asp Pro His Phe Leu Gly Ala Phe Lys Gly Ala Leu Pro Gly His
465                 470                 475                 480

Tyr Arg Tyr Asn Gln Arg Met Tyr Ala His Phe Met Gln Asp Asp Met
                485                 490                 495

Pro Ala Glu Gln Arg Gly Ile Phe Ala Gly Asp Val Ser Trp
            500                 505                 510

Thr Pro Ala Trp Val Gly Ala Val Gln Thr Ser Leu Asn Ala Val
            515                 520                 525

Trp Gly Ile Met Lys His Phe Gly Gly Glu Thr His Ala Glu Asn Pro
            530                 535                 540

Gly Pro Gly Asp Val Phe His Glu Ile Gly Pro Ile Ala Leu Pro Glu
545                 550                 555                 560

<210> SEQ ID NO 9
<211> LENGTH: 560
<212> TYPE: PRT
<213> ORGANISM: Pseudomonas fluorescens Pf0-1

<400> SEQUENCE: 9

Met Asn Lys Asn Arg His Pro Ala Asp Gly Lys Lys Pro Ile Thr
1               5                   10                  15

Ile Phe Gly Pro Asp Phe Pro Phe Ala Phe Asp Asp Trp Ile Glu His
            20                  25                  30

Pro Ala Gly Leu Gly Ser Ile Pro Glu His Asn His Gly Ala Glu Val
        35                  40                  45

Ala Ile Val Gly Ala Gly Ile Ala Gly Leu Val Ala Ala Tyr Glu Leu
    50                  55                  60

Met Lys Leu Gly Leu Lys Pro Val Val Tyr Glu Ala Ser Lys Leu Gly
65                  70                  75                  80

Gly Arg Leu Arg Ser Gln Ala Phe Asn Gly Thr Asp Gly Ile Val Ala
                85                  90                  95

Glu Leu Gly Gly Met Arg Phe Pro Val Ser Ser Thr Ala Phe Tyr His
            100                 105                 110

Tyr Val Asp Lys Leu Gly Leu Glu Thr Lys Pro Phe Pro Asn Pro Leu
        115                 120                 125

Thr Pro Ala Ser Gly Ser Thr Val Ile Asp Leu Glu Gly Lys Thr His
    130                 135                 140
```

```
Tyr Ala Gln Ser Leu Lys Asp Leu Pro Ala Leu Phe Gln Glu Val Ala
145                 150                 155                 160

Asp Ala Trp Ala Asp Ala Leu Glu Ala Gly Ser Gln Phe Ala Asp Ile
                165                 170                 175

Gln Gln Ala Ile Arg Asp Arg Val Pro Arg Leu Lys Glu Leu Trp
            180                 185                 190

Asn Thr Leu Val Pro Leu Trp Asp Asp Arg Thr Phe Tyr Asp Phe Val
            195                 200                 205

Ala Thr Ser Lys Ala Phe Ala Lys Leu Ser Phe His His Arg Glu Val
        210                 215                 220

Phe Gly Gln Val Gly Phe Gly Thr Gly Gly Trp Asp Ser Asp Phe Pro
225                 230                 235                 240

Asn Ser Met Leu Glu Ile Phe Arg Val Val Met Thr Asn Cys Asp Asp
                245                 250                 255

His Gln His Leu Val Val Gly Val Glu Gln Val Pro Gln Gly Ile
            260                 265                 270

Trp Arg His Ala Pro Glu Arg Cys Val His Trp Pro Ala Gly Thr Ser
        275                 280                 285

Leu Lys Ser Leu His His Gly Ala Pro Arg Ser Gly Val Lys Lys Ile
        290                 295                 300

Ala His Ala Pro Asp Gly Arg Phe Ala Val Thr Asp Asn Asn Gly Asp
305                 310                 315                 320

Thr Arg Glu Tyr Ala Ala Val Leu Thr Thr Cys Gln Ser Trp Leu Leu
                325                 330                 335

Thr Thr Gln Ile Glu Cys Asp Glu Ser Leu Phe Ser Gln Lys Met Trp
            340                 345                 350

Met Ala Leu Asp Arg Thr Arg Tyr Met Gln Ser Ser Lys Thr Phe Val
        355                 360                 365

Met Val Asp Arg Pro Phe Trp Lys Asp Lys Asp Pro Glu Thr Gly Arg
370                 375                 380

Asp Leu Met Ser Met Thr Leu Thr Asp Arg Leu Thr Arg Gly Thr Tyr
385                 390                 395                 400

Leu Phe Asp Asn Gly Asp Asp Lys Pro Gly Val Ile Cys Leu Ser Tyr
                405                 410                 415

Ser Trp Met Ser Asp Ala Leu Lys Met Leu Pro His Pro Val Glu Lys
            420                 425                 430

Arg Val Lys Leu Ala Leu Asp Ala Leu Lys Lys Ile Tyr Pro Lys Val
        435                 440                 445

Asp Ile Ala Ala Arg Ile Ile Gly Asp Pro Ile Thr Val Ser Trp Glu
        450                 455                 460

Ala Asp Pro His Phe Leu Gly Ala Phe Lys Gly Ala Leu Pro Gly His
465                 470                 475                 480

Tyr Arg Tyr Asn Gln Arg Met Tyr Ala His Phe Met Gln Asp Met
                485                 490                 495

Pro Gln Glu Gln Arg Gly Ile Phe Ile Ala Gly Asp Val Ser Trp
                500                 505                 510

Thr Pro Ala Trp Val Glu Gly Ala Val Gln Thr Ser Leu Asn Ala Val
            515                 520                 525

Trp Gly Ile Met Lys His Phe Gly Gly Ser Thr His Lys Glu Asn Pro
        530                 535                 540

Gly Pro Gly Asp Val Phe Asn Asp Ile Gly Pro Ile Ala Leu Pro Glu
545                 550                 555                 560
```

<210> SEQ ID NO 10
<211> LENGTH: 567
<212> TYPE: PRT
<213> ORGANISM: Pseudomonas fluorescens WH6

<400> SEQUENCE: 10

Met Ser Ile Pro Ser Ser Thr Leu Ser Lys Pro His Arg His Pro Ala
1               5                   10                  15

Asp Gly Lys Lys Pro Ile Thr Ile Phe Gly Pro Asp Phe Pro Phe Ala
            20                  25                  30

Phe Asp Asp Trp Ile Glu His Pro Ala Gly Leu Gly Ser Ile Pro Ala
        35                  40                  45

Glu His His Gly Ala Glu Val Ala Asn Phe Gly Ala Gly Ile Ala Gly
    50                  55                  60

Leu Val Ala Ala Tyr Glu Leu Met Lys Leu Gly Leu Lys Pro Val Val
65                  70                  75                  80

Tyr Glu Ala Ser Lys Met Gly Gly Arg Leu Arg Ser Gln Ala Phe Glu
                85                  90                  95

Gly Ala Glu Gly Ile Ile Ala Glu Leu Gly Gly Met Arg Phe Pro Val
            100                 105                 110

Ser Ser Thr Ala Phe Tyr His Tyr Val Asp Lys Leu Gly Leu Glu Thr
        115                 120                 125

Lys Pro Phe Pro Asn Pro Leu Thr Pro Ala Ser Gly Ser Thr Val Ile
    130                 135                 140

Asp Leu Glu Gly Glu Thr His Tyr Ala Gln Lys Leu Ser Asp Leu Pro
145                 150                 155                 160

Ala Leu Phe Gln Glu Val Ala Asp Ala Trp Ala Asp Ala Leu Glu Ala
                165                 170                 175

Gly Ser Gln Phe Gly Asp Ile Gln Gln Ala Ile Arg Asp Arg Asp Val
            180                 185                 190

Pro Arg Leu Lys Ala Leu Trp Asn Lys Leu Val Pro Leu Trp Asp Asp
        195                 200                 205

Arg Thr Phe Tyr Asp Phe Val Ala Thr Ser Lys Ala Phe Ala Lys Leu
    210                 215                 220

Ser Phe His His Arg Glu Val Phe Gly Gln Val Gly Phe Gly Thr Gly
225                 230                 235                 240

Gly Trp Asp Ser Asp Phe Pro Asn Ser Met Leu Glu Ile Phe Arg Val
                245                 250                 255

Val Met Thr Asn Cys Asp Asp His Gln His Leu Val Val Gly Gly Val
            260                 265                 270

Ala Gln Val Pro Met Gly Ile Trp Arg His Val Pro Glu Arg Cys Ala
        275                 280                 285

His Trp Pro Ala Gly Thr Ser Leu Ser Ser Leu Ser Gly Ala Pro
    290                 295                 300

Arg Ala Gly Val Lys Arg Ile Ala His Ala Ala Asp Gly Arg Phe Ala
305                 310                 315                 320

Val Thr Asp Asn Tyr Gly Asp Thr Arg Glu Tyr Ala Ala Val Leu Thr
                325                 330                 335

Thr Cys Gln Ser Trp Leu Leu Thr Gln Ile Glu Cys Asp Glu Ser
            340                 345                 350

Leu Phe Ser Gln Lys Met Trp Met Ala Leu Asp Arg Thr Arg Tyr Met
        355                 360                 365

Gln Ser Ser Lys Thr Phe Val Met Val Asp Arg Pro Phe Trp Lys Asp
    370                 375                 380

```
Lys Asp Pro Glu Thr Gly Arg Asp Leu Met Ser Met Thr Leu Thr Asp
385                 390                 395                 400

Arg Leu Thr Arg Gly Thr Tyr Leu Phe Asp Asn Gly Asp Asp Lys Pro
            405                 410                 415

Gly Val Ile Cys Leu Ser Tyr Ser Trp Met Ser Asp Ala Leu Lys Met
        420                 425                 430

Leu Pro Gln Pro Ile Asp Lys Arg Val Lys Leu Ala Leu Asp Ala Leu
    435                 440                 445

Lys Lys Ile Tyr Pro Lys Val Asp Ile Lys Ala Arg Ile Ile Gly Asp
450                 455                 460

Pro Ile Thr Val Ser Trp Glu Ala Asp Pro His Phe Leu Gly Ala Phe
465                 470                 475                 480

Lys Gly Ala Leu Pro Gly His Tyr Arg Tyr Asn Gln Arg Met Tyr Ala
            485                 490                 495

His Phe Met Gln Lys Asp Met Pro Ala Glu Gln Arg Gly Ile Phe Ile
        500                 505                 510

Ala Gly Asp Asp Val Ser Trp Thr Pro Ala Trp Val Glu Gly Ala Val
    515                 520                 525

Gln Thr Ser Leu Asn Ala Val Trp Gly Ile Met Thr His Phe Gly Gly
530                 535                 540

Ser Thr His Ala Glu Asn Pro Gly Pro Gly Asp Val Phe Asp Glu Ile
545                 550                 555                 560

Gly Pro Ile Ser Leu Pro Glu
            565

<210> SEQ ID NO 11
<211> LENGTH: 559
<212> TYPE: PRT
<213> ORGANISM: Pseudomonas syringae pv. lachrymans str. M302278PT

<400> SEQUENCE: 11

Met Lys Asn Asn Arg His Pro Ala Asn Gly Lys Lys Pro Ile Thr Met
1               5                   10                  15

Phe Gly Pro Asp Phe Pro Phe Ala Phe Asp Asp Trp Ile Glu His Pro
            20                  25                  30

Lys Gly Leu Gly Ser Ile Pro Ala Glu His His Gly Ala Glu Val Ala
        35                  40                  45

Ile Ile Gly Ala Gly Ile Ala Gly Leu Val Ala Ala Tyr Glu Leu Met
    50                  55                  60

Lys Met Gly Leu Lys Pro Val Val Tyr Glu Ala Ser Lys Met Gly Gly
65                  70                  75                  80

Arg Leu Arg Ser Gln Glu Phe Glu Gly Ala Lys Gly Ile Val Ala Glu
            85                  90                  95

Leu Gly Gly Met Arg Phe Pro Val Ser Ser Thr Ala Phe His Tyr
        100                 105                 110

Val Asp Lys Leu Gly Leu Glu Ser Arg Pro Phe Pro Asn Pro Leu Thr
    115                 120                 125

Ala Ala Ser Gly Ser Thr Val Ile Asp Leu Glu Gly Thr Thr Tyr Tyr
130                 135                 140

Ala Gln Met Leu Ser Asp Leu Pro Ala Leu Phe Gln Glu Val Ala Asp
145                 150                 155                 160

Ala Trp Ala Asp Ala Leu Glu Ser Gly Ser Gln Phe Gly Asp Ile Gln
            165                 170                 175

Gln Ala Ile Arg Asp Arg Asp Val Pro Arg Leu Lys Glu Leu Trp Asn
```

```
            180                 185                 190
Lys Leu Val Pro Leu Trp Asp Asp Arg Thr Phe Tyr Asp Phe Val Ala
            195                 200                 205

Thr Ser Lys Ala Phe Ala Lys Leu Ser Phe Tyr His Arg Glu Val Phe
            210                 215                 220

Gly Gln Val Gly Phe Gly Thr Gly Gly Trp Asp Ser Asp Phe Pro Asn
225                 230                 235                 240

Ser Met Leu Glu Ile Phe Arg Val Val Met Thr Asn Cys Asp Glu His
                245                 250                 255

Gln His Leu Ile Val Gly Gly Val Gln Val Pro Val Gly Leu Trp
    260                 265                 270

Ser His Val Pro Glu Arg Cys Thr His Trp Pro Lys Gly Thr Ser Leu
            275                 280                 285

Ser Ser Leu His Arg Gly Ala Pro Arg Pro Gly Val Lys Arg Ile Ala
            290                 295                 300

Arg Ala Glu Asp Gly Ser Phe Ala Val Thr Asp Asn Trp Gly Asp Thr
305                 310                 315                 320

Arg Gln Tyr Ala Ala Val Leu Thr Thr Cys Gln Ser Trp Leu Leu Thr
                325                 330                 335

Thr Gln Ile Glu Cys Glu Glu Ser Leu Phe Ser Gln Lys Met Trp Met
                340                 345                 350

Ala Leu Asp Arg Thr Arg Tyr Met Gln Ser Ser Lys Thr Phe Val Met
            355                 360                 365

Val Asp Arg Pro Phe Trp Lys Asp Lys Asp Pro Gln Thr Gly Arg Asp
            370                 375                 380

Leu Met Ser Met Thr Leu Thr Asp Arg Leu Thr Arg Gly Thr Tyr Leu
385                 390                 395                 400

Phe Asp Asn Gly Asp Asp Lys Pro Gly Val Ile Cys Leu Ser Tyr Ser
                405                 410                 415

Trp Met Ser Asp Ala Leu Lys Met Leu Pro Gln Pro Ile Glu Lys Arg
            420                 425                 430

Val Lys Leu Ala Leu Asp Ala Leu Lys Lys Ile Tyr Pro Lys Val Asp
            435                 440                 445

Ile Ala Ala Arg Ile Ile Gly Asp Pro Ile Thr Val Ser Trp Glu Ala
450                 455                 460

Asp Pro His Phe Leu Gly Ala Phe Lys Gly Ala Leu Pro Gly His Tyr
465                 470                 475                 480

Arg Tyr Asn Gln Arg Met Tyr Ala His Phe Met Gln Gln Asp Met Pro
                485                 490                 495

Ser Glu Gln Arg Gly Met Phe Ile Ala Gly Asp Asp Val Ser Trp Thr
            500                 505                 510

Pro Ala Trp Val Glu Gly Ala Val Gln Thr Ser Leu Asn Ala Val Trp
            515                 520                 525

Gly Ile Met Asn His Phe Gly Gly Lys Thr His Ala Glu Asn Pro Gly
            530                 535                 540

Pro Gly Asp Val Phe His Glu Ile Gly Pro Ile Thr Leu Ala Asp
545                 550                 555
```

<210> SEQ ID NO 12
<211> LENGTH: 560
<212> TYPE: PRT
<213> ORGANISM: alpha proteobacterium BAL199

<400> SEQUENCE: 12

```
Met Ser Val Pro Ala Asp Pro Arg Asp Gly Ala Pro Gly Pro Val Thr
  1               5                  10                  15

Val Phe Gly Pro Asp Phe Pro Phe Ala Phe Asp Asp Trp Leu Ala His
             20                  25                  30

Pro Ala Gly Leu Gly Arg Ile Pro Ala Glu Arg His Gly Ala Glu Val
             35                  40                  45

Ala Val Val Gly Ala Gly Ile Ser Gly Leu Ile Val Ala Tyr Glu Leu
 50                  55                  60

Met Lys Leu Gly Leu Arg Pro Val Val Tyr Glu Ser Gly Gln Leu Gly
 65                  70                  75                  80

Gly Arg Leu Arg Ser Gln Pro Phe Glu Gly Ala Asp Gly Ile Val Ala
             85                  90                  95

Glu Leu Gly Gly Met Arg Phe Pro Glu Ser Ser Thr Ala Phe Trp Gln
             100                 105                 110

Tyr Ala Asp Arg Leu Gly Leu Asp Ser Gln Pro Phe Pro Asn Pro Leu
             115                 120                 125

Thr Pro Ala Ala Gly Ser Thr Val Ile Asp Leu Glu Gly Glu Thr His
             130                 135                 140

Tyr Ala Arg Thr Leu Asp Asp Leu Pro Ala Met Phe Arg Glu Val Ala
145                 150                 155                 160

Ala Ala Trp Asp Ala Ala Leu Gln Glu Gly Ala Arg Phe Gly Asp Leu
             165                 170                 175

Arg Ala Ala Leu Arg Ala Arg Asp Val Gly Arg Leu Lys Glu Ile Trp
             180                 185                 190

Asn Ala Leu Val Pro Leu Trp Asp Glu Arg Thr Phe Tyr Asp Phe Val
             195                 200                 205

Ala Ser Ser Ser Ala Phe Ser Ala Leu Pro Phe Arg His Arg Glu Val
             210                 215                 220

Phe Gly Gln Val Gly Phe Gly Thr Gly Gly Trp Asp Ser Asp Phe Pro
225                 230                 235                 240

Asn Ser Met Leu Glu Ile Leu Arg Val Val Leu Thr Gly Cys Asp Asp
             245                 250                 255

Ser Gln Arg Leu Ile Val Gly Val Glu Gln Val Pro Gln Gly Leu
             260                 265                 270

Trp Arg Arg Ala Pro Asp Arg Met Val His Trp Pro Arg Gly Thr Thr
275                 280                 285

Leu Ala Ser Leu His Ala Gly Ala Pro Arg Pro Gly Val Thr Arg Ile
             290                 295                 300

Ala Arg His Ala Gly Gly Ala Leu Ala Val Thr Asp Arg Trp Gly Arg
305                 310                 315                 320

Thr Gln Ala Phe Asp Ala Val Val Ala Thr Cys Gln Ser Trp Leu Leu
             325                 330                 335

Thr Thr Ala Ile Glu Val Asp Glu Pro Leu Phe Ser His Arg Leu Trp
             340                 345                 350

Met Ala Leu Asp Arg Thr Arg Tyr Met Gln Ser Ser Lys Thr Phe Val
             355                 360                 365

Met Val Asp Arg Pro Phe Trp Lys Asp Val Ala Pro Ala Thr Gly Arg
             370                 375                 380

Asp Arg Met Ser Met Thr Leu Thr Asp Arg Leu Thr Arg Gly Thr Tyr
385                 390                 395                 400

Leu Phe Asp Asn Gly Pro Gly Lys Pro Gly Val Ile Cys Leu Thr Tyr
             405                 410                 415

Ser Trp Met Ser Asp Ala Leu Lys Met Leu Pro Leu Pro Val Glu Lys
```

```
            420                 425                 430
Arg Val Asp Leu Ala Leu Gly Ala Leu Ala Lys Ile Tyr Pro Asp Val
            435                 440                 445

Lys Leu Arg Glu His Ile Ile Gly Asp Pro Ile Thr Val Ser Trp Glu
        450                 455                 460

Ala Asp Pro Asn Phe Leu Gly Ala Phe Lys Gly Ala Leu Pro Gly His
465                 470                 475                 480

Tyr Arg Tyr Asn His Arg Met Tyr Gly His Phe Met Gln Ala Asp Leu
                485                 490                 495

Pro Pro Ala Glu Arg Gly Leu Phe Leu Ala Gly Asp Val Ser Trp
            500                 505                 510

Thr Pro Ala Trp Val Glu Gly Ala Val Gln Thr Ala Leu Asn Ala Val
        515                 520                 525

Trp Gly Val Met Thr His Phe Gly Gly His Thr Leu Pro Glu Asn Pro
    530                 535                 540

Gly Pro Gly Asp Leu Tyr Pro Ser Ile Gly Pro Val Thr Leu Pro Glu
545                 550                 555                 560

<210> SEQ ID NO 13
<211> LENGTH: 553
<212> TYPE: PRT
<213> ORGANISM: Pseudonocardia sp. P1

<400> SEQUENCE: 13

Met Ser Pro Asp Pro Arg Pro Val Thr Ala Phe Gly Pro Asp Phe Pro
1               5                   10                  15

Phe Pro Phe Asp Asp Trp Ile Ser His Pro Ala Gly Leu Gly Arg Val
                20                  25                  30

Pro Pro Asp Arg Leu Gly Ala Glu Val Ala Val Gly Ala Gly Ile
            35                  40                  45

Ala Gly Leu Val Ala Ala Tyr Glu Leu Met Arg Ile Gly Leu Arg Pro
    50                  55                  60

Val Val Tyr Glu Pro Ser His Leu Gly Gly Arg Leu Arg Ser Gln Pro
65                  70                  75                  80

Phe Glu Gly Ala Asp Gly Ile Val Ala Glu Leu Gly Gly Met Arg Phe
                85                  90                  95

Pro Arg Ser Ser Thr Ala Phe His His Tyr Val Asp Leu Leu Gly Leu
            100                 105                 110

Arg Thr Glu Pro Phe Pro Asn Pro Leu Thr Pro Ala Ala Gly Ser Thr
        115                 120                 125

Val Ile Asp Leu His Gly Glu Thr Phe Tyr Gly Arg Thr Leu Asp Asp
    130                 135                 140

Leu Pro Pro Phe Phe Ser Glu Val Ala Asp Ala Trp Ala Ser Ala Leu
145                 150                 155                 160

Glu Gln Gly Ala Gly Phe Gly Ala Leu Gln Glu Ala Val Arg Ala Arg
                165                 170                 175

Asp Thr Ala Thr Val Lys Arg Leu Trp Asp Ala Leu Val Pro Leu Trp
            180                 185                 190

Asp Asp Arg Thr Phe Tyr Asp Phe Val Ser Thr Ser Lys Ala Phe Ser
        195                 200                 205

Glu Leu Ser Phe Arg His Arg Glu Ala Phe Gly Gln Val Gly Phe Gly
    210                 215                 220

Thr Gly Gly Trp Asp Ser Asp Phe Pro Asn Ser Met Leu Glu Ile Leu
225                 230                 235                 240
```

```
Arg Val Val Thr Thr Ala Cys Asp Glu Asp Gln Leu Leu Val Thr Gly
            245                 250                 255

Gly Val Glu Gln Val Pro Gln Gly Leu Trp Arg Arg Ala Pro Asp Asp
        260                 265                 270

Ala Val His Trp Pro Ala Gly Thr Ser Leu Ala Ser Leu His Gly Gly
    275                 280                 285

Gly Thr Arg Pro Gly Val Ala Arg Ile His Arg Val Gly Pro Asp Thr
290                 295                 300

Ile Arg Val Thr Asp Thr Tyr Gly Gly Thr Arg Asp Phe Pro Ala Val
305                 310                 315                 320

Leu Thr Thr Cys Gln Ser Trp Leu Leu Ser Thr Gln Ile Asp Thr Asp
                325                 330                 335

Glu Ser Leu Phe Asp Gln Asp Val Trp Met Ala Leu Asp Arg Thr Arg
            340                 345                 350

Tyr Met Gln Ser Thr Lys Thr Phe Val Met Val Asp Arg Pro Phe Trp
        355                 360                 365

Arg Asp Thr Asp Pro Ala Thr Gly Arg Asp Arg Met Ser Met Thr Leu
    370                 375                 380

Thr Asp Arg Leu Thr Arg Ser Thr Tyr Leu Phe Asp His Gly Pro Asp
385                 390                 395                 400

Arg Pro Gly Val Ile Cys Leu Ser Tyr Ser Trp Met Ser Asp Ser Leu
                405                 410                 415

Lys Met Leu Pro Tyr Pro Val Glu Lys Arg Val Gly Leu Ala Leu Ala
            420                 425                 430

Ala Leu Arg Lys Ile Tyr Pro Asp Val Asp Val Ala Ala His Val Ile
        435                 440                 445

Gly Asp Pro Ile Thr Val Thr Trp Glu Ser Asp Pro His Ser Leu Gly
    450                 455                 460

Ala Phe Lys Gly Ala Leu Pro Gly His Tyr Arg Tyr Asn Arg Arg Met
465                 470                 475                 480

Tyr Cys His Phe Val Gln Asp Gly Leu Pro Pro Ala Arg Arg Gly Ile
                485                 490                 495

Phe Met Ala Gly Asp Asp Val Ser Trp Thr Pro Ala Trp Ala Glu Gly
            500                 505                 510

Ala Val Gln Thr Ala Leu Asn Ala Val Trp Gly Ile Val His His Leu
        515                 520                 525

Gly Gly Ala Cys Asp Pro Ala Asn Pro Gly Pro Gly Asp Arg Phe Asp
    530                 535                 540

Glu Leu Ala Pro Leu Ala Leu Pro Asp
545                 550

<210> SEQ ID NO 14
<211> LENGTH: 553
<212> TYPE: PRT
<213> ORGANISM: Gordonia amarae NBRC 15530

<400> SEQUENCE: 14

Met Ala Ala Asp Ala Pro Val Thr Ile Phe Gly Pro Asp Phe Pro Phe
1               5                   10                  15

Ala Tyr Asp Asp Trp Leu Arg His Pro Ala Gly Leu Gly Thr Val Pro
            20                  25                  30

Asp Glu Ala Leu Gly Ser Glu Val Ala Val Ile Gly Ala Gly Met Ala
        35                  40                  45

Gly Met Val Ala Ala Tyr Glu Leu Met Lys Leu Gly Leu Lys Pro Val
    50                  55                  60
```

```
Val Tyr Glu Ala Glu Arg Ile Gly Gly Arg Leu Arg Ser Glu Pro Phe
 65                  70                  75                  80

Ala Pro Gly Glu Pro Glu Ile Ala Glu Leu Gly Gly Met Arg Phe Pro
                 85                  90                  95

Ile Ser Ser Arg Ala Phe Phe His Tyr Val Asp Met Phe Gly Leu Asn
            100                 105                 110

Ala Gln Pro Phe Pro Asn Pro Leu Thr Pro Ala Ser Gly Ser Thr Val
        115                 120                 125

Ile Asp Ile Gly Gly Glu Thr Leu Tyr Ala Arg Thr Leu Asp Asp Leu
    130                 135                 140

Pro Glu Ile Tyr Arg Glu Ile Ala His Ala Trp Asp Ala Ala Leu Glu
145                 150                 155                 160

Arg Ile Ala Gly Phe Thr Glu Leu Gln Asp Ala Ile Arg Thr Arg Asp
                165                 170                 175

Thr Ala Ala Leu Lys Asp Arg Trp Asn Lys Leu Val Arg Glu Trp Asp
            180                 185                 190

Asp Arg Ser Phe Tyr Asp Phe Leu Ala Thr Ser Asp Glu Phe Gly Ser
        195                 200                 205

Leu Ser Tyr Arg His Arg Glu Leu Phe Gly Gln Val Gly Phe Gly Thr
    210                 215                 220

Gly Gly Trp Asp Ser Asp Phe Ala Asn Ser Met Leu Glu Ile Leu Arg
225                 230                 235                 240

Val Val Val Thr Asn Cys Asp Ser Asp Gln Phe Leu Ile Glu Gly Gly
                245                 250                 255

Ser Glu Gln Val Pro Arg Gly Leu Trp Ser His Ala Pro Glu Asn Ile
            260                 265                 270

Ala His Trp Pro Ala Gly Thr Ser Leu Ala Ser Leu His Arg Gly Val
        275                 280                 285

Pro Arg Ala Gly Val Ala Arg Ile Arg Arg Leu Gly Ala Asp Arg Ile
    290                 295                 300

Glu Val Thr Asp Arg Trp Gly Asp Ala His Val Tyr Pro Ala Val Val
305                 310                 315                 320

Ala Thr Cys Gln Ala Trp Leu Leu Ser Thr Glu Ile Asp Cys Asp Glu
                325                 330                 335

Ser Leu Phe Ser Gln Asp Met Trp Met Ala Leu Asp Arg Thr Arg Tyr
            340                 345                 350

Met Gln Ser Ser Lys Thr Phe Val Met Val Asp Arg Pro Phe Trp Lys
        355                 360                 365

Asp Val Asp Pro Asp Thr Gly Arg Asp Val Met Ser Met Thr Leu Thr
    370                 375                 380

Asp Arg Leu Thr Arg Gly Thr Tyr Phe Phe Asp Asn Gly Pro Asp Arg
385                 390                 395                 400

Pro Ala Val Ile Cys Leu Thr Tyr Ser Trp Met Ser Asp Ala Leu Lys
                405                 410                 415

Val Leu Pro His Pro Val Glu Arg Arg Val Glu Leu Ala Leu Ser Ala
            420                 425                 430

Leu Arg Lys Ile Tyr Pro Asn Val Asp Ile Glu Ser His Ile Val Gly
        435                 440                 445

Arg Pro Leu Thr Val Ser Trp Glu Asp Glu Pro His Phe Leu Gly Ala
    450                 455                 460

Phe Lys Gly Ala Leu Pro Gly His Tyr Arg Tyr Asn Thr Arg Met Tyr
465                 470                 475                 480
```

Gly His Phe His Gly Gln Glu Arg Leu Pro Asp Ala Glu Arg Gly Ile
            485                 490                 495

Phe Ile Ala Gly Asp Asp Val Ser Phe Met Pro Ala Trp Val Glu Gly
        500                 505                 510

Ala Val Gln Thr Gly Leu Asn Ala Val Trp Gly Val Leu Ser His Phe
            515                 520                 525

Gly Gly Arg Thr Ser Pro Asp Asn Pro Gly Pro Gly Asp Val Tyr Ala
        530                 535                 540

Arg Leu Gly Pro Ile Asp Ile Gly Glu
545                 550

<210> SEQ ID NO 15
<211> LENGTH: 549
<212> TYPE: PRT
<213> ORGANISM: Roseobacter denitrificans OCh 114

<400> SEQUENCE: 15

Met Lys Pro Val Thr Val Phe Gly Pro Asp Phe Pro Phe Ala Tyr Asp
1               5                   10                  15

Asp Trp Ile Ala His Pro Asp Gly Leu Ala Thr Leu Pro Ala Ala Ala
            20                  25                  30

His Gly Ala His Val Ala Ile Ile Gly Ala Gly Ala Ala Gly Val Ile
        35                  40                  45

Ala Gly Tyr Glu Leu Met Lys Leu Gly Leu Cys Pro Ile Leu Phe Glu
    50                  55                  60

Pro Gly Gln Phe Gly Gly Arg Leu Arg Ser Gln Pro Phe Glu Gly Ala
65                  70                  75                  80

Glu Gly Val Ile Ala Glu Leu Gly Gly Met Arg Phe Pro Val Ser Ser
                85                  90                  95

Thr Gly Phe Tyr His Tyr Val Asp Leu Leu Gly Ile Gln Ser Lys Pro
            100                 105                 110

Phe Pro Asn Pro Leu Thr Pro Ala Ala Gly Ser Thr Val Ile Asp Leu
        115                 120                 125

Leu Gly Lys Thr Tyr Tyr Ala Gln Thr Leu Gln Asp Leu Pro Pro Leu
    130                 135                 140

Phe His Glu Val Ala Gln Ala Tyr Asp Ala Ala Leu Glu Gln Glu Ala
145                 150                 155                 160

Asn Phe Ser Ala Leu Lys Gln Ala Ile Arg Asp Arg Asp Ile Pro Arg
                165                 170                 175

Ile Lys Glu Ile Trp Asn Pro Ile Val Thr Ala Trp Asp Glu Arg Thr
            180                 185                 190

Phe Tyr Asp Phe Val Ala Ser Ser Glu Ala Phe Lys Lys Leu Thr Phe
        195                 200                 205

His His Arg Glu Val Phe Gly Gln Val Gly Phe Gly Thr Gly Gly Trp
    210                 215                 220

Asp Ser Asp Phe Pro Asn Ser Met Leu Glu Ile Leu Arg Val Asn Val
225                 230                 235                 240

Thr Glu Cys Asp Asp His Gln Arg Tyr Met Val Gly Val Glu Gln
                245                 250                 255

Val Pro Arg Lys Leu Trp Gln His Lys Pro Asp Arg Leu Val His Trp
            260                 265                 270

Pro Ala Gly Thr Ser Leu Arg Ser Leu Asn Asp Gly Ala Thr Arg Ser
        275                 280                 285

Gly Ala Lys Arg Ile Arg Arg Leu Asp Ala Gly Gln Ile Glu Val Thr
    290                 295                 300

Asp Ala Trp Gly Arg Ala Glu Gly Phe Asp Ala Val Leu Val Thr Cys
305                 310                 315                 320

Gln Thr His Leu Leu Ser Thr Gln Ile Asp Thr Glu Glu Ser Leu Phe
            325                 330                 335

Ser Gln Asp Leu Trp Met Ala Leu Asp Arg Thr Arg Tyr Met Gln Ser
            340                 345                 350

Ala Lys Thr Phe Val Met Val Asp Arg Pro Phe Trp Lys Asp Lys His
            355                 360                 365

Pro Val Thr Gly Arg Asp Thr Met Ser Met Thr Leu Thr Asp Arg Met
370                 375                 380

Thr Arg Gly Thr Tyr Leu Phe Asp Asn Gly Pro Asp Lys Pro Ser Val
385                 390                 395                 400

Ile Cys Leu Ser Tyr Ala Trp Met Thr Asp Ala Leu Lys Val Leu Pro
                405                 410                 415

Leu Pro Val Glu Gln Arg Val Glu Leu Ala Leu Ala Ala Leu Ala Lys
            420                 425                 430

Ile Tyr Pro Asp Val Asp Ile Arg Ser His Ile Leu Gly Asp Pro Ile
            435                 440                 445

Thr Val Ser Trp Glu Ala Asp Gln Asn Phe Leu Gly Ala Phe Lys Gly
450                 455                 460

Ala Leu Pro Gly His Tyr Arg Tyr Asn His Arg Met Phe Gly His Phe
465                 470                 475                 480

Val Gln Ser Asp Met Pro Ala Arg Glu Arg Gly Ile Phe Leu Ala Gly
                485                 490                 495

Asp Gly Val Ser Trp Thr Pro Ala Trp Val Gly Ala Val Gln Thr
            500                 505                 510

Ser Leu Asn Ala Val Ala Gly Ile Ile Ala His Phe Gly Gly Thr Pro
            515                 520                 525

Ser Pro Ala Asn Pro Ser Pro Leu Glu Ala Tyr Glu Lys His Gly Pro
            530                 535                 540

Val Arg Leu Ser Ala
545

<210> SEQ ID NO 16
<211> LENGTH: 560
<212> TYPE: PRT
<213> ORGANISM: Mycobacterium abscessus ATCC 19977

<400> SEQUENCE: 16

Met Thr Ser Leu Leu Pro Gly Ala Asp Asn Ala Ile Lys Pro Val Ser
1               5                   10                  15

Ile Phe Gly Pro Asp Phe Pro Phe Glu Phe Asp Ala Trp Ile Ser His
            20                  25                  30

Pro Asp Gly Leu Gly Gln Val Pro Glu Ala Ala Phe Gly Gln Glu Val
            35                  40                  45

Ala Ile Ile Gly Ala Gly Ile Ala Gly Met Val Ala Ala Tyr Glu Leu
        50                  55                  60

Met Lys Leu Gly Leu Arg Pro Val Leu Tyr Glu Ser Ala Arg Ile Gly
65                  70                  75                  80

Gly Arg Leu Arg Ser Gln Gln Phe Asp Gly Ala Pro Glu Gly Val Ile
            85                  90                  95

Ala Glu Leu Gly Gly Met Arg Phe Pro Ser Ser Ser Phe Ser Phe Phe
            100                 105                 110

His Tyr Val Asp Met Leu Gly Leu Thr Ala Lys Pro Phe Pro Asn Pro

```
                115                 120                 125
Leu Thr Pro Ala Ala Gly Ser Thr Val Ile Asp Ile Glu Gly Val Thr
            130                 135                 140
His His Ala Arg Ala Ile Asp Glu Leu Pro Gln Ile Phe Gln Glu Val
145                 150                 155                 160
Ala Glu Ala Trp Ala Glu Ala Leu Glu Glu Val Ser Phe Thr Pro Val
                165                 170                 175
Gln Asp Ala Ile Arg Ala Arg Asp Ala Val Thr Leu Lys Ser Leu Trp
            180                 185                 190
Asn Gln Leu Val Thr Glu Trp Asp Asp Arg Thr Phe Tyr Asp Phe Val
            195                 200                 205
Ala Ser Ser Lys Ala Phe Ser Lys Leu Ser Phe His His Arg Glu Val
            210                 215                 220
Phe Gly Gln Val Gly Phe Gly Thr Gly Gly Trp Asp Ser Asp Phe Pro
225                 230                 235                 240
Asn Ser Met Leu Glu Ile Leu Arg Val Val Met Thr Asn Cys Asp Glu
                245                 250                 255
Asp Gln Gln Leu Ile Val Gly Ala Glu Gln Val Pro Arg Gly Leu
            260                 265                 270
Trp Thr Tyr Glu Pro Asp Ser Met Cys His Trp Pro Arg Gly Thr Thr
                275                 280                 285
Leu Ala Lys Leu His Arg Gly Val Pro Arg Ser Arg Val Lys Arg Ile
            290                 295                 300
Ala Arg Gly Pro His Gly Gln Leu Ser Val Thr Asp Gln Trp Gly Val
305                 310                 315                 320
Thr Arg Asp Tyr Pro Ala Val Leu Ala Thr Cys Gln Ser Trp Leu Leu
                325                 330                 335
Thr Thr Glu Ile Asp Cys Asp Glu Ser Leu Phe Ser Gln Lys Met Trp
                340                 345                 350
Thr Ala Leu Asp Arg Thr Arg Tyr Met Gln Ser Ser Lys Thr Phe Val
            355                 360                 365
Leu Val Asp Arg Pro Phe Trp Lys Asp Val Asp Pro Val Thr Gly Arg
            370                 375                 380
Asp Thr Met Ser Met Thr Leu Thr Asp Arg Met Thr Arg Gly Thr Tyr
385                 390                 395                 400
Phe Phe Asp Asn Gly Asp Asp Ala Pro Ala Val Val Cys Leu Thr Tyr
                405                 410                 415
Ser Trp Met Ser Asp Ala Met Lys Val Leu Pro Tyr Ser Ala Gln Asp
                420                 425                 430
Arg Ala Asp Met Ala Leu Asn Ala Leu Lys Arg Ile Tyr Pro Gln Val
            435                 440                 445
Asp Ile Asn Gln His Ile Val Gly Glu Pro Ile Ser Val Ser Trp Glu
            450                 455                 460
Ala Asp Arg Asn Phe Leu Gly Ala Phe Lys Gly Ala Leu Pro Gly His
465                 470                 475                 480
Tyr Arg Tyr Asn His Arg Met Tyr Ser His Phe Met Gln Asp Gln His
                485                 490                 495
Glu Ala Gly His Arg Gly Ile Phe Leu Ala Gly Asp Asp Val Ser Trp
            500                 505                 510
Thr Pro Ala Trp Ala Glu Gly Ala Val Gln Thr Ala Leu Asn Ala Val
            515                 520                 525
Trp Gly Ile Met Thr His Phe Gly Gly Gly Ser Ser Thr Arg Asn Pro
            530                 535                 540
```

Gly Pro Gly Asp Val Phe Ala Glu Ile Gly Pro Leu Lys Leu Pro Glu
545                 550                 555                 560

<210> SEQ ID NO 17
<211> LENGTH: 30
<212> TYPE: DNA
<213> ORGANISM: Artificial
<220> FEATURE:
<223> OTHER INFORMATION: Description of Artificial Sequence: Synthetic
      DNA
<220> FEATURE:
<221> NAME/KEY: misc_feature
<222> LOCATION: (9)..(9)
<223> OTHER INFORMATION: n is a, c, g or t
<220> FEATURE:
<221> NAME/KEY: misc_feature
<222> LOCATION: (12)..(12)
<223> OTHER INFORMATION: n is a, c, g or t

<400> SEQUENCE: 17
atgaacaana anaaccgcca cccsgccgac                                        30

<210> SEQ ID NO 18
<211> LENGTH: 30
<212> TYPE: DNA
<213> ORGANISM: Artificial
<220> FEATURE:
<223> OTHER INFORMATION: Description of Artificial Sequence: Synthetic
      DNA

<400> SEQUENCE: 18
tcartcygcc agggcgatyg gsccgatytc                                        30

<210> SEQ ID NO 19
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 19
agcacggtaa tcgatctgga                                                   20

<210> SEQ ID NO 20
<211> LENGTH: 20
<212> TYPE: DNA
<213> ORGANISM: Artificial
<220> FEATURE:
<223> OTHER INFORMATION: Description of Artificial Sequence: Synthetic
      DNA

<400> SEQUENCE: 20
catcgagtgc cagttgcacg                                                   20

<210> SEQ ID NO 21
<211> LENGTH: 29
<212> TYPE: DNA
<213> ORGANISM: Artificial
<220> FEATURE:
<223> OTHER INFORMATION: Description of Artificial Sequence: Synthetic
      DNA

<400> SEQUENCE: 21
tataatcata tgaacaagaa caaccgcca                                         29

<210> SEQ ID NO 22

```
<211> LENGTH: 31
<212> TYPE: DNA
<213> ORGANISM: Artificial
<220> FEATURE:
<223> OTHER INFORMATION: Description of Artificial Sequence: Synthetic
      DNA

<400> SEQUENCE: 22
tattactcga gtcagtccgc cagggcgatt g                                      31

<210> SEQ ID NO 23
<211> LENGTH: 33
<212> TYPE: DNA
<213> ORGANISM: Artificial
<220> FEATURE:
<223> OTHER INFORMATION: Description of Artificial Sequence: Synthetic
      DNA
<220> FEATURE:
<221> NAME/KEY: misc_feature
<222> LOCATION: (16)..(17)
<223> OTHER INFORMATION: n is a, c, g or t.

<400> SEQUENCE: 23
gtggtgatga ccaatnnsga cgaccaccaa cac                                    33

<210> SEQ ID NO 24
<211> LENGTH: 33
<212> TYPE: DNA
<213> ORGANISM: Artificial
<220> FEATURE:
<223> OTHER INFORMATION: Description of Artificial Sequence: Synthetic
      DNA
<220> FEATURE:
<221> NAME/KEY: misc_feature
<222> LOCATION: (16)..(17)
<223> OTHER INFORMATION: n is a, c, g or t.

<400> SEQUENCE: 24
gcggtgctga cgaccnnsca gagttggctg ctg                                    33

<210> SEQ ID NO 25
<211> LENGTH: 33
<212> TYPE: DNA
<213> ORGANISM: Artificial
<220> FEATURE:
<223> OTHER INFORMATION: Description of Artificial Sequence: Synthetic
      DNA
<220> FEATURE:
<221> NAME/KEY: misc_feature
<222> LOCATION: (16)..(17)
<223> OTHER INFORMATION: n is a, c, g or t.

<400> SEQUENCE: 25
aagccagggg tgatcnnsct gtcctacgcg tgg                                    33

<210> SEQ ID NO 26
<211> LENGTH: 33
<212> TYPE: DNA
<213> ORGANISM: Artificial
<220> FEATURE:
<223> OTHER INFORMATION: Description of Artificial Sequence: Synthetic
      DNA
<220> FEATURE:
<221> NAME/KEY: misc_feature
<222> LOCATION: (16)..(17)
<223> OTHER INFORMATION: n is a, c, g or t.

<400> SEQUENCE: 26
catgtgccag agcgtnnsgc gcactggccc gaa                                    33
```

```
<210> SEQ ID NO 27
<211> LENGTH: 33
<212> TYPE: DNA
<213> ORGANISM: Artificial
<220> FEATURE:
<223> OTHER INFORMATION: Description of Artificial Sequence: Synthetic
      DNA
<220> FEATURE:
<221> NAME/KEY: misc_feature
<222> LOCATION: (16)..(17)
<223> OTHER INFORMATION: n is a, c, g or t.

<400> SEQUENCE: 27 accaccaga tcgacnnsga agagtcgttg ttc                                  33
```